(12) United States Patent
Vigneault et al.

(10) Patent No.: US 10,928,392 B2
(45) Date of Patent: Feb. 23, 2021

(54) HIGH THROUGHPUT PROCESS FOR T CELL RECEPTOR TARGET IDENTIFICATION OF NATIVELY-PAIRED T CELL RECEPTOR SEQUENCES

(71) Applicants: ABVITRO LLC, Boston, MA (US); Francois Vigneault, Seattle, WA (US); Adrian Wrangham Briggs, Seattle, WA (US); Stephen J. Goldfless, Seattle, WA (US); Brian J. Belmont, Seattle, WA (US)

(72) Inventors: Francois Vigneault, Yarrow Point, WA (US); Adrian Wrangham Briggs, Seattle, WA (US); Stephen J. Goldfless, Seattle, WA (US); Brian J. Belmont, Seattle, WA (US)

(73) Assignee: AbVitro LLC, Seattle, WA (US)

(*) Notice: Subject to any disclaimer, the term of this patent is extended or adjusted under 35 U.S.C. 154(b) by 0 days.

(21) Appl. No.: 15/762,450

(22) PCT Filed: Sep. 23, 2016

(86) PCT No.: PCT/US2016/053595
§ 371 (c)(1),
(2) Date: Mar. 22, 2018

(87) PCT Pub. No.: WO2017/053902
PCT Pub. Date: Mar. 30, 2017

(65) Prior Publication Data
US 2019/0025299 A1    Jan. 24, 2019

Related U.S. Application Data

(60) Provisional application No. 62/232,511, filed on Sep. 25, 2015.

(51) Int. Cl.
C40B 30/04 (2006.01)
G01N 33/566 (2006.01)
C07K 14/725 (2006.01)

(52) U.S. Cl.
CPC ....... G01N 33/566 (2013.01); C07K 14/7051 (2013.01); C40B 30/04 (2013.01);
(Continued)

(58) Field of Classification Search
None
See application file for complete search history.

(56) References Cited

FOREIGN PATENT DOCUMENTS

| CN | 103249430 | 8/2013 |
| CN | 104769103 | 7/2015 |

(Continued)

OTHER PUBLICATIONS

International Search Report and Written Opinion issued in International Application No. PCT/US2016/053595, dated Apr. 1, 2017 (9 pages).

(Continued)

*Primary Examiner* — Christian C Boesen
(74) *Attorney, Agent, or Firm* — Finnegan, Henderson, Farabow, Garrett & Dunner, LLP

(57) ABSTRACT

Provided herein are methods and composition for high-throughput T-cell receptor target identification of natively paired T-cell receptor sequences.

36 Claims, 18 Drawing Sheets
Specification includes a Sequence Listing.

(52) U.S. Cl.
  CPC ............... *G01N 2333/7051* (2013.01); *G01N 2800/7028* (2013.01)

(56) References Cited

FOREIGN PATENT DOCUMENTS

| | | | |
|---|---|---|---|
| JP | 2004537314 A | 12/2004 | |
| JP | 2013541332 A | 11/2013 | |
| WO | WO 2015/014869 A1 * | 2/2015 | ............ A61K 39/00 |
| WO | WO 2015121454 | 8/2015 | |
| WO | WO 2016/100977 A1 | 6/2016 | |
| WO | WO 2016176322 | 11/2016 | |

OTHER PUBLICATIONS

Dössinger et al., "MHC Multimer-Guided and Cell Culture-Independent Isolation of Functional T Cell Receptors from Single Cells Facilitates TCR Identification for Immunotherapy," PLoS One, 2013, vol. 8, No. 4, e61384.

Simon et al., "Functional TCR Retrieval from Single Antigen-Specific Human T Cells Reveals Multiple Novel Epitopes," Cancer Immunology Research, 2014, vol. 2, No. 12, p. 1230-44.

Turchaninova et al., "Pairing of T-cell Receptor Chains via Emulsion PCR," European Journal of Immunology, 2013, vol. 43, p. 2507-15.

Aarnoudse et al., "TCR reconstitution in Jurkat reporter cells facilitates the identification of novel tumor antigens by cDNA expression cloning," International Journal of Cancer vol. 99, Mar. 12, 2002 (Mar. 12, 2002), pp. 7-13.

\* cited by examiner

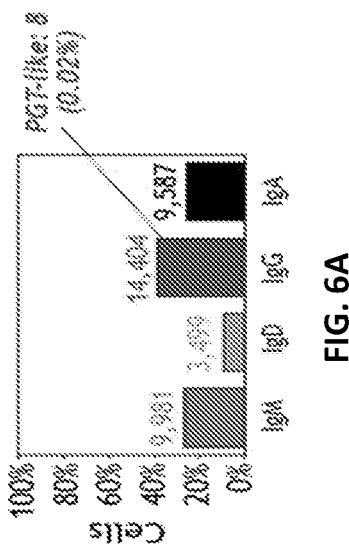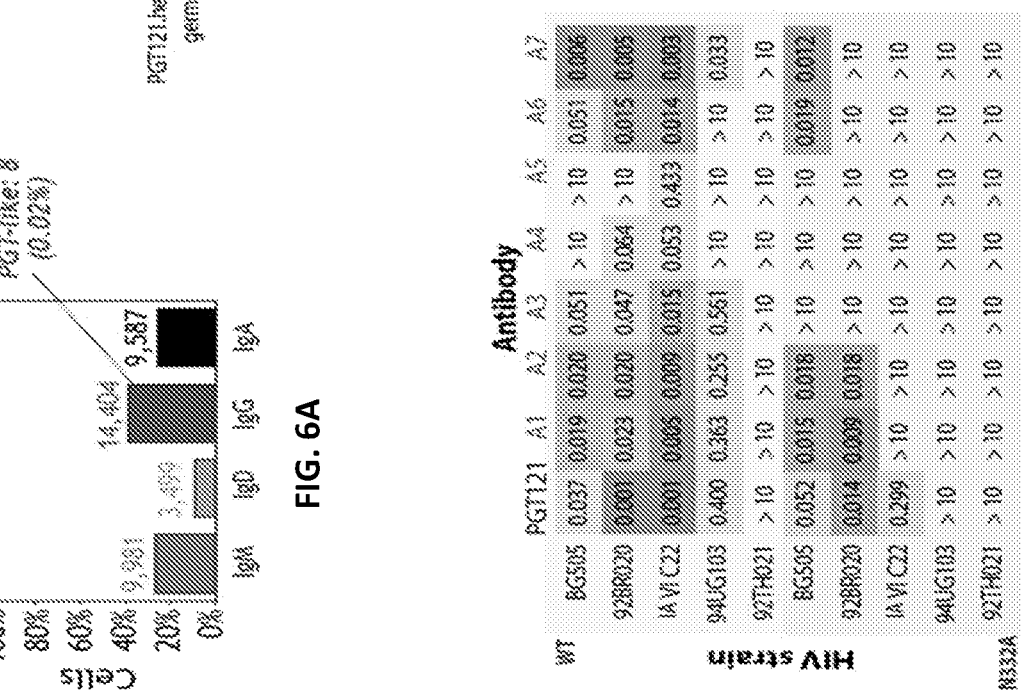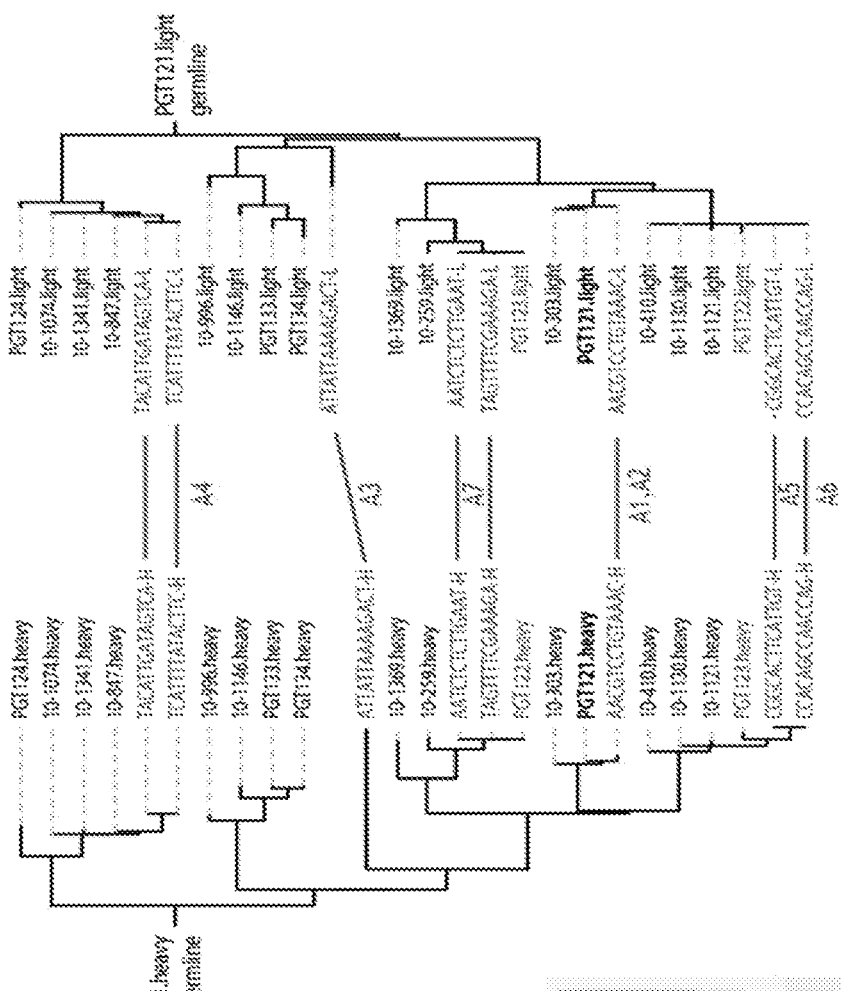
FIG. 6A
FIG. 6B
FIG. 6C

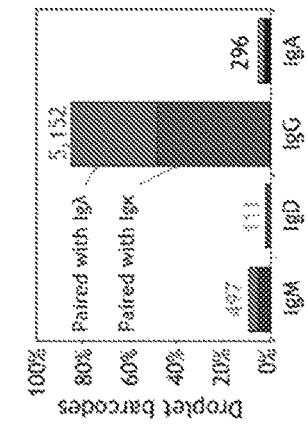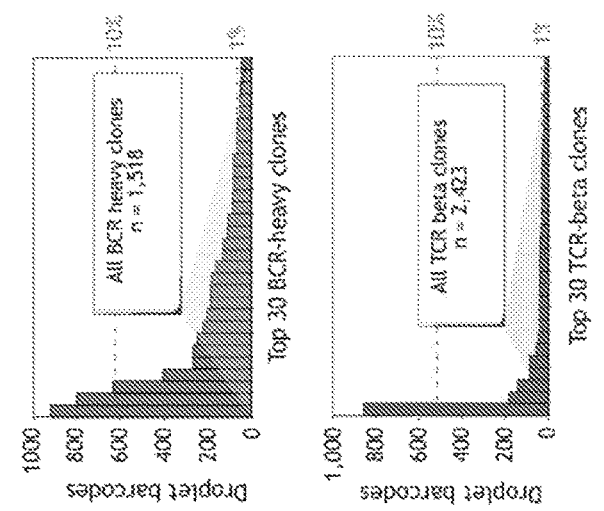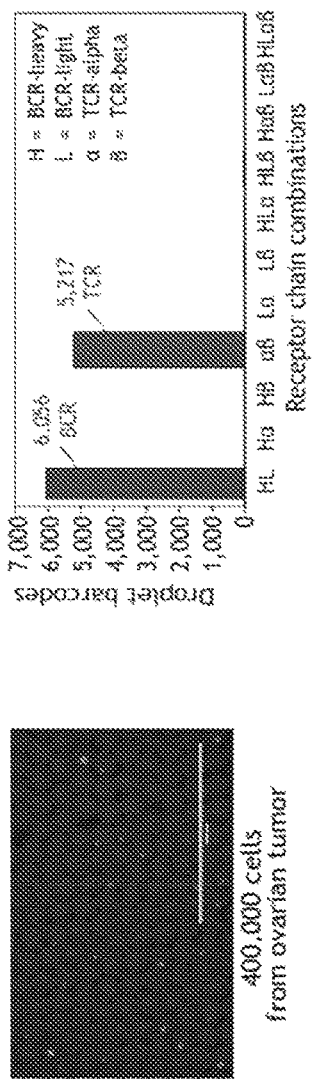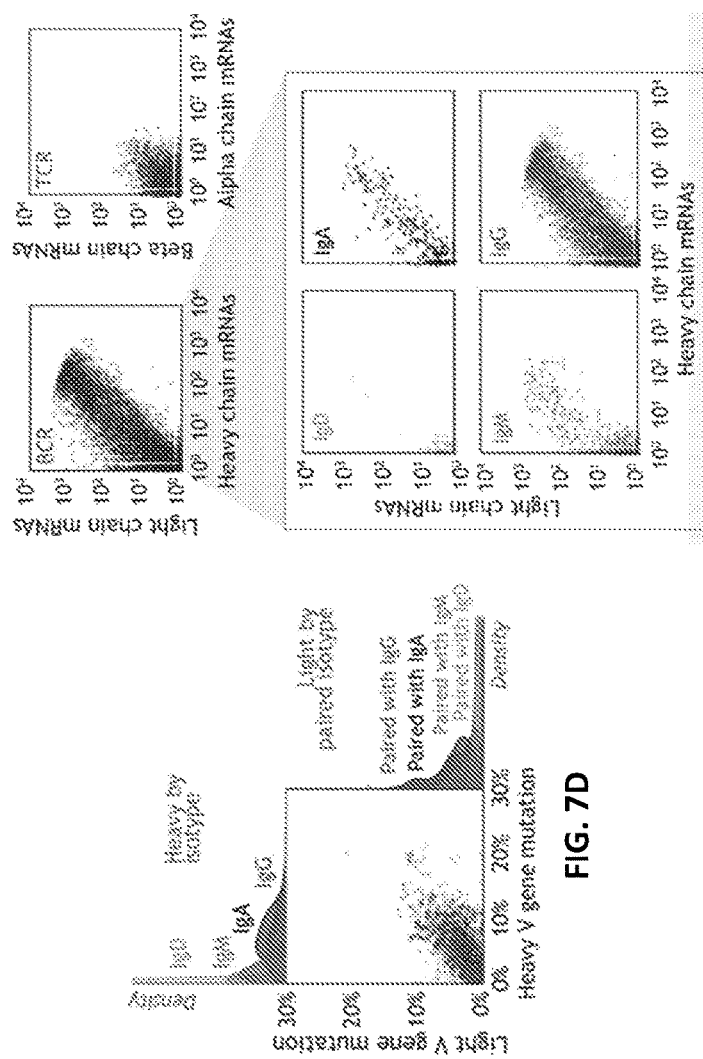
FIG. 7A FIG. 7B FIG. 7C FIG. 7D FIG. 7E FIG. 7F

|  | protein | | | |
|---|---|---|---|---|
| 3,682 TCR $V_\alpha V_\beta$ droplet barcodes / mRNA | CD4 | CD8 | undef | |
| CD4 | 33.0% | 1.4% | 0.4% | 34.8% |
| CD8 | 0.7% | 16.6% | 0.1% | 17.4% |
| undef | 30.7% | 13.5% | 3.6% | 47.8% |
| TOTAL | 64.5% | 31.5% | 4.0% | 100.0% |

FIG. 8D

SEQUENCE LISTING

```
<160> NUMBER OF SEQ ID NOS: 8

<210> SEQ ID NO 1
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
```
tacattgata gtca                                              14

<210> SEQ ID NO 2
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tcattttata cttc                                              14

<210> SEQ ID NO 3
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
attattaaaa gact                                              14

<210> SEQ ID NO 4
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
aatctctctt gaat                                              14

<210> SEQ ID NO 5
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tagttttcga aaga                                              14

<210> SEQ ID NO 6
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
aacgtcctgt aaac                                              14

<210> SEQ ID NO 7
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
cggcacttca ttgt                                              14

```
<210> SEQ ID NO 8
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ccacagccaa ccag                                                     14
```

HIGH THROUGHPUT PROCESS FOR T CELL RECEPTOR TARGET IDENTIFICATION OF NATIVELY-PAIRED T CELL RECEPTOR SEQUENCES

CROSS-REFERENCE

This application is a U.S. National Phase Application under 35 U.S.C. § 371 of International Application No. PCT/US2016/053595, filed Sep. 23, 2016, which claims priority to U.S. Provisional Application No. 62/232,511, filed Sep. 25, 2015; which are incorporated herein by reference in their entireties.

SEQUENCE LISTING

The instant application contains a Sequence Listing which has been filed electronically in ASCII format and is hereby incorporated by reference in its entirety. Said ASCII copy, created on Jan. 2, 2020, is named ABV712-SL.txt and is 2,241 bytes in size.

BACKGROUND

T lymphocytes, or T cells, are an integral component of the adaptive immune system in humans and other animals. They compose an important portion of the cell-mediated immunity within an organism. Many T cell subsets exist, including cytotoxic T cells and helper T cells. Cytotoxic T cells (also known as $CD8^+$ T cells) kill abnormal cells, for example virus-infected or tumor cells. Helper T cells (also known as $CD4^+$ T cells) aid in the activation and maturation of other immune cells.

Both cytotoxic and helper T cells carry out their function subsequent to the recognition of specific target antigens which triggers their respective responses. The antigen specificity of a T cell is defined by the T cell receptor (TCR) expressed on the surface of the T cell. T cell receptors are heterodimer proteins composed of two polypeptide chains, most commonly an alpha and beta chain, but a minority of T cells express a gamma and delta chain. The specific amino acid sequence of the TCR and the resultant three-dimensional structure defines the TCR antigen specificity and affinity. The amino acid and coding DNA sequences of the TCR chains for any individual T cell are almost always unique or at very low abundance in an organism's entire TCR repertoire, since there are a vast number of possible TCR sequences. This large sequence diversity is achieved during T cell development through a number of cellular mechanisms and is a critical aspect of the immune system's ability to respond to a huge variety of potential antigens.

TCR target antigens are peptides which are displayed by an antigen presenting cell (APC). On the cell surface of an APC, a peptide is presented to a T cell in complex with a Major Histocompatibility Complex (MHC) protein, referred to as Human Leukocyte Antigens (HLA) in humans. MHC class I proteins display peptide antigens to cytotoxic T cells and MHC class II proteins display peptide antigens to helper T cells. MHC genes are highly polymorphic, and thus the specific set of MHC proteins for any organism often differs substantially from most or all others within the species.

In order for TCR-antigen recognition to occur, a T cell interacts with an APC presenting the TCR's cognate peptide. The peptide must be in complex with an MHC molecule recognized by the TCR and is compatible with the T cell type, either MHC-I proteins with $CD8^+$ T cells or MHC-II proteins with $CD4^+$ T cells. Upon proper TCR-antigen/MHC recognition, the T cell is activated, leading to various cellular effects.

SUMMARY

Disclosed herein are methods and compositions to screen and determine the antigen specificity of large numbers of TCRs derived from high-throughput single cell analysis. In one aspect provided herein is a method comprising identifying a plurality of natively paired TCR chains from a biological sample from a subject using high-throughput parallel single-cell sequencing; expressing a TCR polypeptide in one or more engineered cells, wherein the TCR polypeptide comprises at least one pair of the natively paired TCR chains; contacting the one or more engineered cells to one or more of a plurality of engineered antigen presenting cells (APCs), wherein each engineered APC of the plurality of engineered APCs comprises a different antigen polypeptide; identifying a reactive engineered APC of the plurality of engineered APCs, wherein the reactive engineered APC has reactivity and/or exhibits a response to the engineered cell expressing the TCR polypeptide; and determining the antigen polypeptide of the selected APC, thereby determining a target antigen of the natively paired TCR chains.

In one aspect provided herein is a method comprising identifying a plurality of natively paired TCR chains from a biological sample from a subject using high-throughput parallel single-cell sequencing; expressing a TCR polypeptide in one or more engineered cells, wherein the TCR polypeptide comprises at least one pair of the natively paired TCR chains; contacting the one or more engineered cells to one or more of a plurality of engineered antigen presenting cells (APCs), wherein each engineered APC of the plurality of engineered APCs comprises a different antigen polypeptide; identifying an activating engineered APC of the plurality of engineered APCs, wherein the activating engineered APC activates the engineered cell expressing the TCR polypeptide; and determining the antigen polypeptide of the selected engineered APC, thereby determining a target antigen of the natively paired TCR chains.

In one aspect provided herein is a method comprising identifying a plurality of natively paired TCR chains from a biological sample from a subject using high-throughput parallel single-cell sequencing; expressing a TCR polypeptide in one or more engineered cells, wherein the TCR polypeptide comprises at least one pair of the natively paired TCR chains; contacting the one or more engineered cells to one or more of a plurality of engineered antigen presenting cells (APCs), wherein each engineered APC of the plurality of engineered APCs presents a different antigen polypeptide; identifying a reactive engineered APC of the plurality of engineered APCs, wherein the reactive engineered APC has reactivity and/or exhibits a response to the engineered cell expressing the TCR polypeptide; and determining the antigen polypeptide presented on the cell surface of the selected engineered APC, thereby determining a target antigen of the natively paired TCR chains.

In one aspect provided herein is a method comprising identifying a plurality of natively paired TCR chains from a biological sample from a subject using high-throughput parallel single-cell sequencing; expressing a TCR polypeptide in one or more engineered cells, wherein the TCR polypeptide comprises at least one pair of the natively paired TCR chains; contacting the one or more engineered cells to one or more of a plurality of engineered antigen presenting cells (APCs), wherein each engineered APC of the plurality of engineered APCs presents a different antigen polypeptide; identifying an activating engineered APC of the plurality of engineered APCs, wherein the activating engineered APC activates the engineered cell expressing the TCR polypeptide; and determining the antigen polypeptide presented on the cell surface of the selected engineered APC, thereby determining a target antigen of the natively paired TCR chains.

In one aspect provided herein is a method comprising identifying a plurality of natively paired TCR chains from a biological sample from a subject using high-throughput parallel single-cell sequencing; a TCR polypeptide in one or more engineered cells, wherein the TCR polypeptide comprises at least pair one of the natively paired TCR chains; contacting the one or more engineered cells to a plurality of engineered antigen presenting cells (APCs), wherein each engineered APC of the plurality of engineered APCs comprises a different antigen polypeptide; identifying a reactive engineered APC of the plurality of engineered APCs, wherein the reactive engineered APC has reactivity and/or exhibits a response to the engineered cell expressing the TCR polypeptide; and determining the antigen polypeptide of the selected APC, thereby determining a target antigen of the natively paired TCR chains.

In one aspect provided herein is a method comprising identifying a plurality of natively paired TCR chains from a biological sample from a subject using high-throughput parallel single-cell sequencing; expressing a TCR polypeptide in one or more engineered cells, wherein the TCR polypeptide comprises at least one pair of the natively paired TCR chains; contacting the one or more engineered cells to one or more of a plurality of engineered antigen presenting cells (APCs), wherein each engineered APC of the plurality of engineered APCs comprises a different antigen polypeptide; determining the antigen polypeptide of an engineered APC that has reactivity and/or exhibits a response to an engineered cell of the one or more engineered cells expressing a TCR polypeptide, determining a target antigen of the natively paired TCR chains, wherein the determined target antigen is the antigen polypeptide of the engineered APC that has reactivity and/or exhibits a response to the engineered cell of the one or more engineered cells expressing a TCR polypeptide.

In one aspect provided herein is a method comprising identifying a plurality of natively paired TCR chains from a biological sample from a subject using high-throughput parallel single-cell sequencing; expressing a TCR polypeptide in one or more engineered cells, wherein the TCR polypeptide comprises at least one pair of the identified natively paired TCR chains; contacting the one or more engineered cells to one or more of a plurality of engineered antigen presenting cells (APCs), wherein each engineered APC of the plurality of engineered APCs presents a different antigen polypeptide; determining the antigen polypeptide presented on the cell surface of an engineered APC that has reactivity and/or exhibits a response to an engineered cell of the one or more engineered cells expressing a TCR polypeptide; determining a target antigen of the natively paired TCR chains, wherein the determined target antigen is the antigen polypeptide presented on the cell surface of the engineered APC that has reactivity and/or exhibits a response to the engineered cell of the one or more engineered cells expressing a TCR polypeptide.

In one aspect provided herein is a method comprising identifying a plurality of natively paired TCR chains from a biological sample from a subject using high-throughput parallel single-cell sequencing; expressing a TCR polypeptide in one or more engineered cells, wherein the TCR polypeptide comprises at least one pair of the identified natively paired TCR chains; contacting the one or more engineered cells to one or more of a plurality of engineered antigen presenting cells (APCs), wherein each engineered APC of the plurality of engineered APCs comprises a different antigen polypeptide; determining the antigen polypeptide of an engineered APC that activates an engineered cell of the one or more engineered cells expressing a TCR polypeptide; determining a target antigen of the natively paired TCR chains, wherein the determined target antigen is the antigen polypeptide of the engineered APC that activates the engineered cell of the one or more engineered cells expressing a TCR polypeptide.

In one aspect provided herein is a method comprising identifying a plurality of natively paired TCR chains from a biological sample from a subject using high-throughput parallel single-cell sequencing; expressing a TCR polypeptide in one or more engineered cells, wherein the TCR polypeptide comprises at least one pair of the identified natively paired TCR chains; contacting the one or more engineered cells to one or more of a plurality of engineered antigen presenting cells (APCs), wherein each engineered APC of the plurality of engineered APCs presents a different antigen polypeptide; determining the antigen polypeptide presented on the cell surface of an engineered APC that activates an engineered cell of the one or more engineered cells expressing a TCR polypeptide; determining a target antigen of the natively paired TCR chains, wherein the determined target antigen is the antigen polypeptide presented on the cell surface of the engineered APC that activates the engineered cell of the one or more engineered cells expressing a TCR polypeptide.

In one aspect provided herein is a method comprising contacting one or more engineered cells to one or more of a plurality of antigen presenting cells (APCs), wherein the one or more engineered cells express a T-cell receptor (TCR) polypeptide comprising a at least one pair of natively paired TCR chains of a single immune cell from a subject; assaying for reactivity of an APC of the plurality of APCs to an engineered cell of the one or more engineered cells expressing a TCR polypeptide; selecting an APC that has reactivity to the engineered cell of the one or more engineered cells expressing a TCR polypeptide; and determining an antigen polypeptide of the selected APC, thereby determining a target antigen of the natively paired TCR chains.

In one aspect provided herein is a method comprising contacting one or more engineered cells to one or more of a plurality of antigen presenting cells (APCs), wherein the one or more engineered cells express a T-cell receptor (TCR) polypeptide comprising at least one pair of natively paired TCR chains of a single immune cell from a subject; assaying for activation of an APC of the plurality of APCs by an engineered cell of the one or more engineered cells expressing a TCR polypeptide; selecting an APC that activates the engineered cell of the one or more engineered cells expressing a TCR polypeptide; and determining an antigen polypeptide of the selected APC, thereby determining a target antigen of the natively paired TCR chains.

In one aspect provided herein is a method comprising contacting one or more engineered cells to one or more of a plurality of antigen presenting cells (APCs), wherein the one or more engineered cells express a T-cell receptor (TCR) polypeptide comprising at least one pair of natively paired TCR chains of a single immune cell from a subject; determining an antigen polypeptide presented by an APC of the plurality of APCs that has reactivity to an engineered cell of the one or more engineered cells expressing a TCR polypeptide; and determining a target antigen of the natively paired TCR chains, wherein the determined target antigen is the determined antigen polypeptide presented by the APC of the plurality of APCs that has reactivity to an engineered cell of the one or more engineered cells expressing a TCR polypeptide.

In one aspect provided herein is a method comprising contacting an one or more engineered cells to a plurality of antigen presenting cells (APCs), wherein the one or more engineered cells express a T-cell receptor (TCR) polypeptide comprising at least one pair of natively paired TCR chains of a single immune cell from a subject; determining an antigen polypeptide presented by an activated APC of the plurality of APCs that is activated by an engineered cell of the one or more engineered cells expressing a TCR polypeptide; and determining a target antigen of the native TCR chain pair, wherein the determined target antigen is the determined antigen polypeptide presented by the activated APC of the plurality of APCs that is activated by an engineered cell of the one or more engineered cells expressing a TCR polypeptide.

In one aspect provided herein is a method comprising contacting a one or more engineered cells to a plurality of engineered antigen presenting cells (APCs) that present an antigen polypeptide associated with a disease, wherein the one or more engineered cells express a T-cell receptor (TCR) polypeptide comprising at least one pair of natively paired TCR chains of a single immune cell from a subject; determining an engineered APC of the plurality of APCs that is activated by an engineered cell of the one or more engineered cells or has reactivity to an engineered cell of the one or more engineered cells; selecting the engineered APC of the plurality of APCs that is activated by an engineered cell of the one or more engineered cells or has reactivity to an engineered cell of the one or more engineered cells.

In one aspect provided herein is a method comprising contacting one or more engineered cells to a sample comprising a plurality of cells, wherein the one or more engineered cells express a T-cell receptor (TCR) polypeptide comprising at least one pair of natively paired TCR chains of a single immune cell from a subject; assaying for reactivity of a cell of the plurality of cells to an engineered cell of the one or more engineered cells expressing a TCR polypeptide to a cell in the sample comprising the plurality of cells; selecting a cell from the sample comprising the plurality of cells that has reactivity to the engineered cell of the one or more engineered cells expressing a TCR polypeptide; and determining an antigen polypeptide of the selected cell, thereby determining a target antigen of the natively paired TCR chains.

In one aspect provided herein is a method comprising contacting one or more engineered cells to a sample comprising a plurality of cells, wherein the one or more engineered cells express a T-cell receptor (TCR) comprising at least one pair of natively paired TCR chains of a single immune cell from a subject; assaying for activation of a cell of the plurality of cells by an engineered cell of the one or more engineered cells expressing a TCR polypeptide by a cell in the sample comprising the plurality of cells; selecting a cell from the sample comprising the plurality of cells that activates the engineered cell of the one or more engineered cells expressing a TCR polypeptide; and determining an antigen polypeptide of the selected cell, thereby determining a target antigen of the natively paired TCR chains.

In one aspect provided herein is a method comprising contacting one or more engineered cells to a sample comprising a plurality of cells, wherein the one or more engineered cells express a T-cell receptor (TCR) polypeptide comprising at least one pair of natively paired TCR chains of a single immune cell from a subject; determining an antigen polypeptide presented by a cell in the sample comprising the plurality of cells that has reactivity to an engineered cell of the one or more engineered cells expressing s TCR polypeptide, determining a target antigen of the natively paired TCR chains, wherein the determined target antigen is the determined antigen polypeptide presented by the cell in the sample comprising the plurality of cells that has reactivity to an engineered cell of the one or more engineered cells expressing a TCR polypeptide.

In one aspect provided herein is a method comprising contacting one or more engineered cells to a sample comprising a plurality of cells, wherein the one or more engineered cell express a T-cell receptor (TCR) polypeptide comprising at least one pair of natively paired TCR chains of a single immune cell from a subject; determining an antigen polypeptide presented by a cell in the sample comprising the plurality of cells that activates an engineered cell of the one or more engineered cells expressing a TCR polypeptide, determining a target antigen of the natively paired TCR chains, wherein the determined target antigen is the determined antigen polypeptide presented by the cell in the sample comprising the plurality of cells that activates an engineered cell of the one or more engineered cells expressing a TCR polypeptide.

In some embodiments, the plurality of natively paired TCR chains is identified simultaneously or from a single reaction.

In some embodiments, the APC is an engineered APC.

In some embodiments, the TCR polypeptide is expressed from an exogenous polynucleotide. In some embodiments, the antigen polypeptide is expressed from an exogenous polynucleotide sequence. In some embodiments, each engineered APC of the plurality of engineered APCs comprises an antigen polypeptide expressed from an exogenous polynucleotide sequence encoding a different antigen. In some embodiments, the one or more engineered cells express a TCR polypeptide from an exogenous polynucleotide sequence.

In some embodiments, the exogenous polynucleotide sequence encodes a first T-cell receptor (TCR) chain and a second TCR chain. In some embodiments, the first and second TCR chains comprise the at least one pair of natively paired TCR chains.

In some embodiments, the engineered APC that is activated by the engineered cell or that has reactivity to the engineered APC is for use as an immunotherapeutic In some embodiments, the engineered APC comprises a plurality of engineered APCs that recognize a plurality of engineered cells.

In some embodiments, the plurality of engineered APCs expresses at least one MHC type. In some embodiments, the plurality of engineered APCs expresses at least two MHC types. In some embodiments, the engineered APC that is activated by the engineered cell or has reactivity to the engineered cell expresses an MHC-type specific for the TCR polypeptide of the engineered cell. In some embodiments, the plurality of engineered cells expresses a TCR polypeptide specific for an MHC-type expressed by the engineered APC in the plurality of engineered APCs.

In some embodiments, the antigen polypeptide associated with a disease is known. In some embodiments, the one or more engineered cells comprises a first plurality of engineered cells from a first subject and a second plurality of engineered cells from a second subject, and wherein the plurality of engineered APCs comprises a first plurality of engineered APCs and a second plurality of engineered APCs. In some embodiments, the method comprises contacting the first plurality of engineered cells to the first plurality of APCs and contacting the second plurality of engineered cells to the second plurality of APCs. In some embodiments, the first plurality of engineered APCs and a second plurality of engineered APCs present the same antigen polypeptide. In some embodiments, the first plurality of engineered APCs express a first MHC-type and the second plurality of engineered APCs express a second MHC-type.

In some embodiments, the first plurality of engineered cells expresses a first TCR polypeptide specific for the first MHC-type expressed by the first plurality of engineered APCs and the second plurality of engineered cells expresses a second TCR polypeptide specific for the second MHC-type expressed by the second plurality of engineered APCs. In some aspects, a library of TCR polypeptides is provided comprising the first TCR polypeptide and the second TCR polypeptide. In some embodiments, the first TCR polypeptide is specific to a complex comprising the antigen polypeptide and an MHC of the first MHC-type, and wherein the second TCR polypeptide is specific to a complex comprising the antigen polypeptide and an MHC of the second MHC-type.

In some embodiments, the TCR polypeptide is for use as an immunotherapeutic.

In some embodiments, the method further comprises identifying a plurality of natively paired TCR chains from a biological sample from a subject using high-throughput parallel single-cell sequencing, wherein the plurality of natively paired TCR chains are identified simultaneously or from a single reaction. In some embodiments, the method further comprises generating one or more engineered cells expressing at least one of the identified natively paired TCR chains that were identified simultaneously or from a single reaction.

In some embodiments, the APC is from a diseased subject.

In some embodiments, the sample cell is from a subject. In some embodiments, the sample cell is a cell line. In some embodiments, the sample cell is from a diseased subject. In some embodiments, the antigen presenting cell is from a subject with cancer. In some embodiments, the antigen presenting cell is from a subject infected by a virus. In some embodiments, the antigen presenting cell is from the same subject as the single immune cell. In some embodiments, the antigen presenting cell is from a subject with a major histocompatibility complex (MHC) repertoire that is similar to the MHC repertoire of the subject comprising the single immune cell. In some embodiments, the antigen presenting cell is from a subject with a major histocompatibility complex (MHC) haplotype that is similar to the MHC haplotype of the subject comprising the single immune cell. In some embodiments, the antigen presenting cell is from a subject with a major histocompatibility complex (MHC) repertoire that is compatible with the subject comprising the single immune cell. In some embodiments, the engineered APC is engineered to express MHC genes matched to the subject. In some embodiments, the engineered APC is derived from a K562 cell line. In some embodiments, the engineered cell expressing the TCR polypeptide is derived from a Jurkat cell line. In some embodiments, the antigen presenting cell is a primary cell. In some embodiments, the antigen presenting cell is cell line. In some embodiments, an antigen presenting cell (APC) from a subject has reactivity to the engineered cell expressing the TCR polypeptide. In some embodiments, an antigen presenting cell (APC) from a subject is activated by the engineered cell expressing the TCR polypeptide.

In some embodiments, the method further comprises isolating the engineered APC. In some embodiments, the determining the antigen of the engineered APC comprises sequencing a sequence of the engineered APC encoding an antigen presented by the engineered APC. In some embodiments, the engineered APC is isolated by fluorescence activated cell-sorting.

In some embodiments, the method further comprises transfecting the exogenous polynucleotide sequence encoding a first T-cell receptor (TCR) chain and a second TCR chain. In some embodiments, the method further comprises transfecting the exogenous polynucleotide sequence encoding a different antigen. In some embodiments, the method further comprises adding a different antigen to the cell surface of the engineered APC.

In some embodiments, the method further comprises determining the natively paired TCR chain sequences of the single immune cell from the subject before the contacting. In some embodiments, the method further comprises determining the target antigen of each of a plurality of natively paired TCR chains. In some embodiments, the engineered cell comprises a plurality of engineered cells, each expressing a different pair of natively paired TCR chain sequences.

In some embodiments, the engineered cell is an engineered T-cell that does not express an endogenous TCR polypeptide. In some embodiments, the engineered cell is an engineered T-cell that does not transcribe an endogenous TCR gene. In some embodiments, the engineered cell is an engineered T-cell does not comprise an endogenous TCR gene. In some embodiments, the engineered cell is an engineered T-cell is a TCR knock-out cell. In some embodiments, the engineered cell is a T-cell. In some embodiments, the engineered cell expresses CD4. In some embodiments, the engineered cell expresses CD8.

In some embodiments, the antigen presenting cell comprises a plurality of antigen presenting cells, each presenting a different antigen. In some embodiments, the antigen presenting cells of the assaying are in separate vessels.

In some embodiments, the APC comprises an exogenous reporter sequence. In some embodiments, the APC comprises an exogenous reporter sequence encoding a reporter gene. In some embodiments, the reporter gene is a luciferase gene. In some embodiments, the reporter gene encodes a fluorescent protein. In some embodiments, the reporter gene encodes a cell-surface protein. In some embodiments, binding of a cell surface expressed protein ligand to a synthetic Notch (synNotch) receptor on the engineered APC causes expression of the reporter gene. In some embodiments, the cell surface expressed protein ligand is expressed by the engineered cell. In some embodiments, the cell surface expressed protein ligand is under control of an inducible promoter. In some embodiments, the inducible promoter is a NFAT promoter. In some embodiments, the synNotch receptor is cleaved and a transcriptional activator domain, such as a GAL4-VP64 domain is generated. In some embodiments, the transcriptional activator domain induces expression of the reporter gene. In some embodiments, the transcriptional activator domain induces expression of the reporter gene by binding to an activating sequence, such as a GAL4-UAS activating sequence. In some embodiments, expression of the reporter gene indicates activation of the engineered cell by the APC. In some embodiments, expression of the reporter gene indicates reactivity of the engineered APC to the engineered cell. In some embodiments, the assaying comprises assaying for expression of the reporter gene.

In some embodiments, the assaying comprises a cDNA array, mRNA detection, or protein detection.

In some embodiments, the APC comprises an exogenous reporter sequence encoding a reporter gene. In some embodiments, the reporter gene is a luciferase gene. In some embodiments, the reporter gene encodes a fluorescent protein. In some embodiments, the reporter gene encodes a cell-surface protein. In some embodiments, the reporter gene encodes IL6, IL-12, IFNα, IL-23, IL-1, TNF, or IL-10. In some embodiments, the cell-surface protein is CD80, CD86, MHC I, MHC II, CD11c, CD11b, CD8α, OX40-L, ICOS-1, or CD40. In some embodiments, the reporter gene is activated in response to CD80/CD86 on the engineered APC binding to CD28 on the engineered cell. In some embodiments, the reporter gene is activated downstream of Notch signaling activation in the APC. In some embodiments, the reporter gene is activated downstream of PI3K/AKT signaling activation in the APC. In some embodiments, the reporter gene is activated downstream of an NF-κB pathway, or a NOTCH1 signaling pathway.

In some embodiments, the reporter gene is activated downstream of a second receptor. In some embodiments, the second receptor is activated after binding a ligand secreted by the engineered cell. In some embodiments, expression of the ligand is induced after binding of a synthetic Notch (synNotch) receptor on the engineered APC.

In some embodiments, the engineered APC does not express an endogenous MHC polypeptide. In some embodiments, the engineered APC does not transcribe an endogenous MHC gene. In some embodiments, the engineered APC does not comprise an endogenous MHC gene.

In some embodiments, the first TCR chain comprises a TCR-alpha chain and the second TCR chain comprises a TCR-beta chain. In some embodiments, the first TCR chain comprises a TCR-gamma chain and the second TCR chain comprises a TCR-delta chain.

In one aspect, provided herein is a method of treatment, the method comprising administering to a subject in need thereof a therapeutic targeted against a protein comprising the antigen determined according to a method described herein. In some embodiments, the subject is a human. In some embodiments, the therapeutic is a small molecule, a peptide, a protein, an antibody or fragment thereof, a cell therapy or an immunotherapy. In some embodiments, the cell therapy comprises adoptive cell therapy. In some embodiments, the method comprises administering a T cell engineered to express one or more natively paired TCR chains of the plurality of TCR chains identified according to a method described herein. In some embodiments, the subject has a disease or condition. In some embodiments, the disease or condition is cancer.

INCORPORATION BY REFERENCE

All publications, patents, and patent applications mentioned in this specification are herein incorporated by reference in their entirety for all purposes, to the same extent as if each individual publication, patent, or patent application was specifically and individually indicated to be incorporated by reference.

BRIEF DESCRIPTION OF THE DRAWINGS

The novel features described herein are set forth with particularity in the appended claims. A better understanding of the features and advantages of the features described herein will be obtained by reference to the following detailed description that sets forth illustrative examples, in which the principles of the features described herein are utilized, and the accompanying drawings of which:

FIG. 4 exemplifies results from a method of single immune cell barcoding in an emulsion.

FIG. 5 exemplifies results from a method of BCR recovery from isolated healthy B-cells

FIG. 6 exemplifies results from a method of HIV broad neutralizing antibody (bNAb) discovery FIG. 6A is an exemplary graph of heavy chain isotype distribution of 38,620 recovered $V_H V_L$ pairs from B-cells from an HIV elite controller were entered into emulsion. A rare proportion of the IgG chains aligned well to previously known bNAbs ("PGT-like").

FIG. 6B is an exemplary depiction of phylogenetic trees of complete VDJ amino acid sequences of known bNAbs (black) plus the newly recovered ones (connected by lines, labeled with droplet barcode), with heavy (left) and light chains (right) plotted separately. Potentially mismatched antibodies are PGT122.heavy and PGT123.light, and PGT123.heavy and PGT122.light. Both the left and right columns of FIG. 6B disclose SEQ ID NOs: 1-8 (from top to bottom).

FIG. 6C is an exemplary depiction of neutralization activity ($IC_{50}$, μg/mL) of 8 newly discovered PGT-like variants against ten strains of HIV, compared to a control stock of PGT121.

FIG. 7 exemplifies results from a method of characterization of TILs from an ovarian tumor.

FIG. 7A is an exemplary depiction of droplets in which 400,000 unsorted dissociated cells from an ovarian tumor were entered into emulsion and BCR and TCR pairs were simultaneously recovered by emulsion barcoding.

FIG. 7B is an exemplary graph of droplet barcodes vs. receptor chain combinations showing the numbers of all $V_H/V_L$ and Vα/Vβ combinations observed within droplet barcodes after filtering.

FIG. 7C is an exemplary graph of droplet barcode percentage vs. heavy chain isotype distribution of recovered BCR pairs.

FIG. 7D is an exemplary graph of $V_H$ vs $V_L$ mutation correlation for BCR pairs and density distributions within each isotype.

FIG. 7E depicts exemplary graphs of the numbers of captured mRNAs for TCR pairs and BCR pairs overall (top) and for different isotypes (bottom).

FIG. 7F depicts exemplary graphs of clonal analysis showing the rank abundance of the 30 most frequent BCR heavy chain clones (top) and the 30 most frequent TCR beta chain clones in each of six independent emulsion fractions. 1% and 10% overall frequency levels are shown.

FIG. 8D depicts an exemplary table of simultaneous mRNA and protein detection of CD4 and CD8 from unsorted T-cells in emulsion. From 30,000 input T-cells, 3,682 TCR pairs were recovered. Frequencies of TCR pairs called as $CD4^+$ or $CD8^+$ by mRNA vs protein (based on molecular counting, majority rule) are shown in a matrix.

FIG. 10 exemplifies a method of immunophenotyping using antibody-oligonucleotide conjugates.

DETAILED DESCRIPTION

Figure 1:
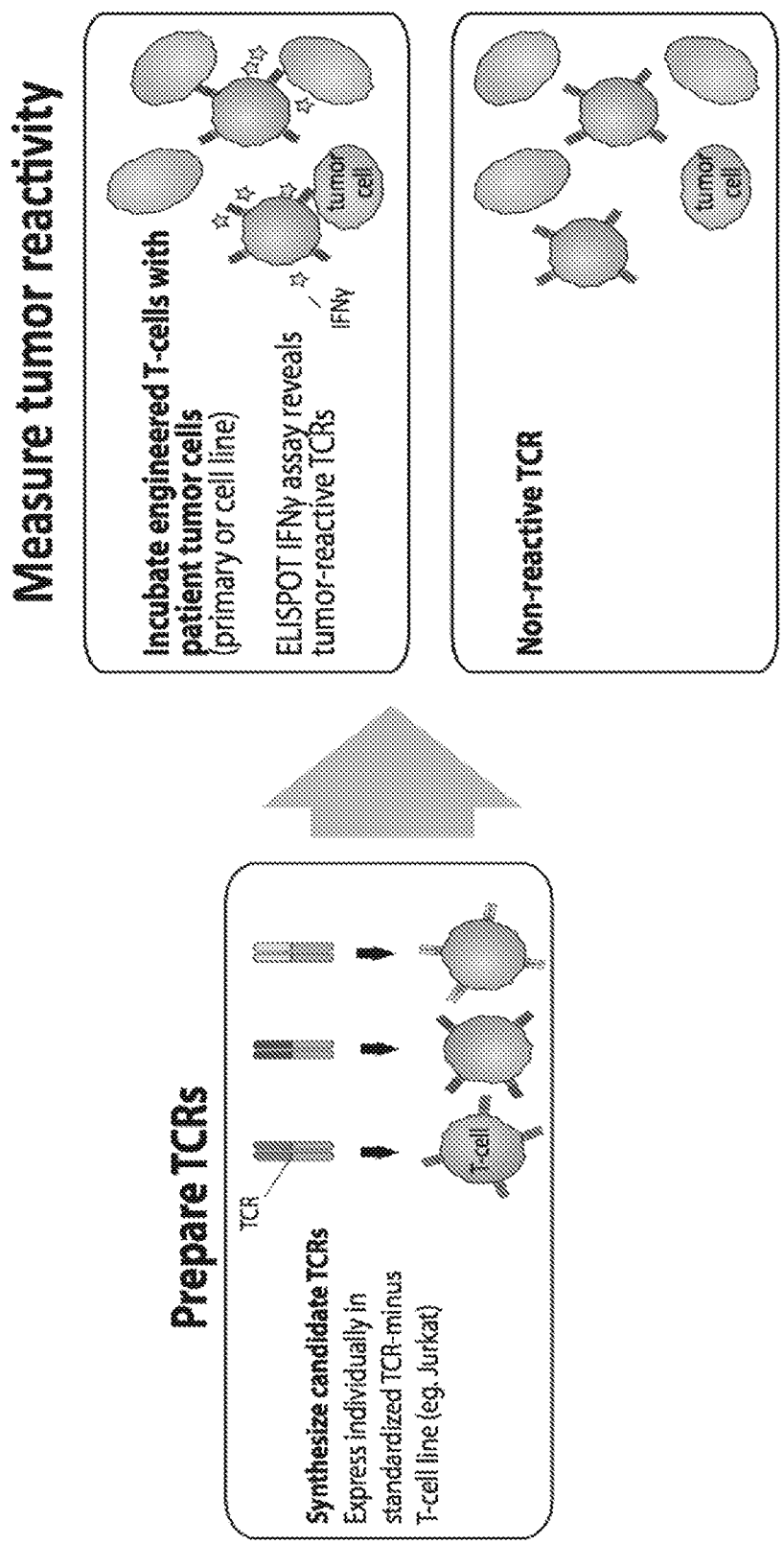
FIG. 1 depicts an exemplary flow chart for a screening method of initial tumor reactivity for patient-derived TCRs.

Several aspects are described below with reference to example applications for illustration. It should be understood that numerous specific details, relationships, and methods are set forth to provide a full understanding of the features described herein. One having ordinary skill in the relevant art, however, will readily recognize that the features described herein can be practiced without one or more of the specific details or with other methods. The features described herein are not limited by the illustrated ordering of acts or events, as some acts can occur in different orders and/or concurrently with other acts or events. Furthermore, not all illustrated acts or events are required to implement a methodology in accordance with the features described herein.

The terminology used herein is for the purpose of describing particular cases only and is not intended to be limiting. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising".

The term "about" or "approximately" can mean within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, within 5-fold, and more preferably within 2-fold, of a value. Where particular values are described in the application and claims, unless otherwise stated the term "about" meaning within an acceptable error range for the particular value should be assumed.

It is an object of the invention to provide methods and compositions for phenotyping single cells (e.g., immune cells using antibody-oligonucleotide conjugates (e.g., in emulsions).

TCR specificity is determined by the amino acid sequences of both of its TCR chains (alpha and beta or gamma and delta). To recapitulate a TCR, for further characterization, both chain sequences are desired to be determined. These polypeptide chains are expressed independently from unique genetic loci within the T cell. TCR sequencing approaches using a bulk T cell population yield many chain sequences, but it determining the native pairing of TCR chains derived from the same original cell has remained difficult. Thus, in order to determine the complete, properly paired TCR chain sequences from an individual T cell, a single cell analysis method is important.

While single-cell TCR sequencing methods have existed for years, they historically have very low throughput (1-100 cells per experiment). Recently, researchers have invented new ways to profile the paired TCR repertoire of vast numbers of single T cells, yielding thousands to millions of natively paired TCR sequences. Unfortunately, there exist no straightforward and efficient methods to determine the antigen specificity of a large number of TCRs.

In one aspect, a method comprises determining which TCRs are reactive to a specific tissue type of interest (e.g. tumor cells or virus-infected cells) (FIG. 1). After initial sequence determination, paired TCR chains can be cloned into a suitable expression vector or a lentiviral vector and coexpressed within an appropriate T cell line. A T cell line (e.g. Jurkat) can be engineered to express no endogenous TCRs and expresses the CD4 or CD8 co-receptor, depending of the experimental objective. Thus, the antigen specificity of these T cells can be determined by the introduced TCR. Additionally, these T cells can contain a reporter DNA construct that expresses a reporter gene (e.g. luciferase or fluorescent protein) upon TCR-antigen recognition and subsequent T cell activation. This can involve, for example, an NFAT protein-responsive promoter which is upregulated upon T cell activation.

These engineered, TCR-expressing T cells can be incubated with APCs of interest, either primary cells or a cell line. These APC cells can be derived from an original host that yielded the TCR or another host with a similar MHC repertoire. This can ensure that the MHC alleles can be recognized by the TCR under investigation.

T cell activation/TCR reactivity can be determined by either the engineered reporter gene expression or secretion of an immune-relevant cytokine (e.g. IFN-gamma).

Figure 2:
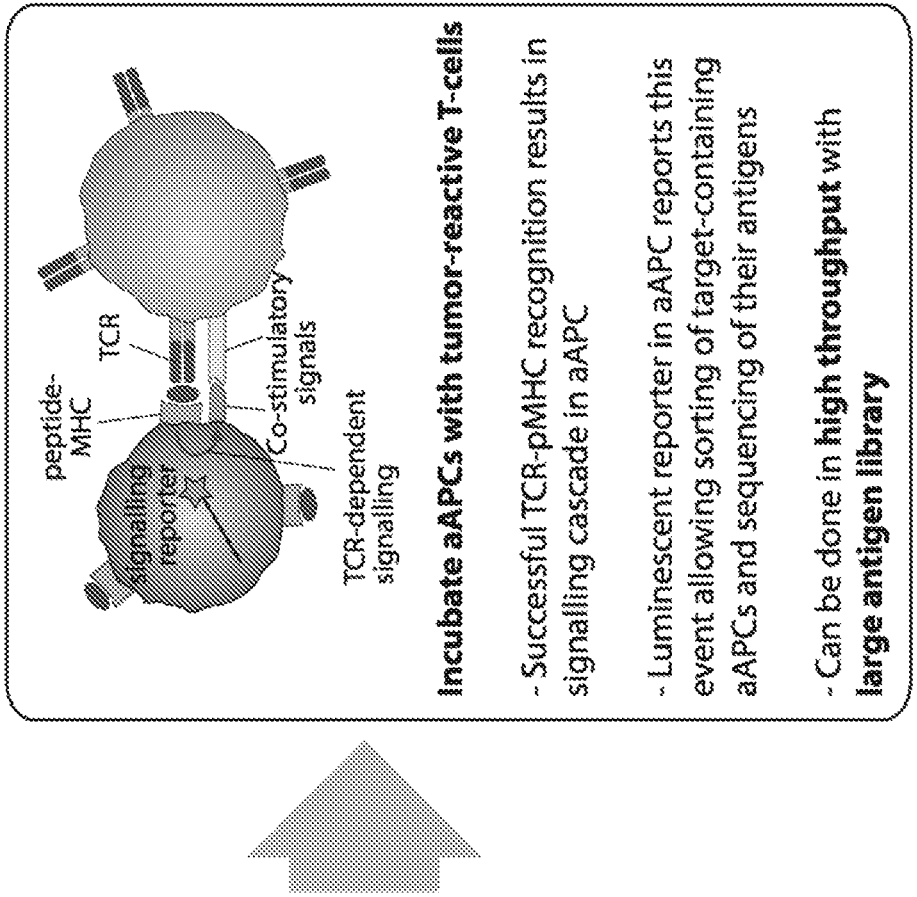
FIG. 2 depicts an exemplary flow chart for a method of target identification of patient-derived TCRs.
Figure 2:

In one aspect, a method further comprises identifying the antigen of candidate TCR hits (FIG. 2). In some embodiments, TCR expression vectors are transfected into a similar T cell line as above. In some embodiments, TCR expression vectors are transfected into a similar T cell line as above, but without the activation reporter.

In some embodiments, T cells are mixed with cell-based artificial or engineeredAPCs (aAPCs or eAPCs, respectively). In some embodiments, the aAPC cell lines (e.g. based on the K562 cell line) do not express endogenous MHC proteins. In some embodiments, the aAPC cells are transfected with MHC gene(s) matched to those of the source organism of the TCR under investigation. MHC is also referred to herein as human leukocyte antigen (HLA) in humans. In some embodiments, aAPCs also are engineered to contain a reporter construct which will express a reporter gene (e.g. luciferase, fluorescent protein, surface protein) upon antigen recognition by a T cell.

In some embodiments, a library of antigen-expressing vectors is transfected into aAPCs. An antigen coding sequence can be for the peptide of interest, a minigene construct or an entire cDNA coding sequence which can be processed appropriately into peptides prior to MHC-I binding and surface display. Peptides can also be directly added to the aAPCs for MHC loading. The antigen library can be composed of an unbiased set of protein coding regions from the target cell of interest or can be more narrowly defined (e.g. neoantigens determined by exome sequencing, virus-derived genes).

In some embodiments, TCR-expressing T cells are incubated with the antigen-presenting aAPCs. Successful TCR-antigen/MHC recognition leads to the activation of the T cell and causes the aAPC reporter gene to express. In some embodiments, TCR-expressing T-cells are incubated with non-engineered and/or non-artificial APCs expressing endogenous MHC. In some embodiments, endogenous APCs are pulsed with a library of target antigens.

An advantage of this method is that a T cell population expressing a single TCR can be interrogated against a large library of potential antigens. aAPCs displaying the target antigen of T cell TCR can express the reporter gene. The expression of the reporter gene can permit isolation of the aAPC. For example, expression of the reporter gene can permit isolation of the aAPC by fluorescence activated cell sorting or surface marker-based methods. The coding sequence of the antigen expressed in each isolated aAPC can be determined, which will uncover the identity of the presented antigen and, therefore, the target of the TCR. This, ultimately, allows for the robust determination of the specificity of many TCRs against a large library of potential antigens.

The methods and compositions described herein enable the discovery of therapeutically-relevant TCRs against disease targets. In some embodiments, TCR sequences from a representative human population are obtained. In some embodiments, a library of these is transfected or transduced into T cells. In some embodiments, the T cells are incubated with different sets of aAPCs which express a specific MHC and target antigen. In some embodiments, the T cell contains a reporter gene construct that is expressed upon antigen recognition and T cell activation. In some embodiments, the reporter allows for the isolation of activated cells from the population through fluorescence or surface marker-based sorting. In some embodiments, such TCRs reactive against disease-relevant targets may be useful and may be applicable in the treatment of disease. Due to the diversity in MHC sequences within the human population, it is advantageous to discover multiple TCRs reactive against the same antigen, but compatible with a specific, relatively common MHC.

Several million unstimulated naïve and resting memory B-cells from peripheral blood and hundreds of thousands of dissociated tumor cells were evaluated, yielding repertoire-level datasets of full-length, paired BCRs from the blood sample and both BCRs and TCRs from TILs in the tumor. While T-cells have traditionally been the primary focus of TIL research, the roles of B-cells in tumors are receiving increasing attention. Renewed interest in TILs from the broad scientific community can be attributed to groundbreaking development in cell transfer immunotherapies, development of CAR-T against solid tumors, and the discovery of checkpoint inhibitors and their impact on tumor growth. These fields of research all require an understanding of the TILs involved, either to monitor TIL fluctuation and evolution in responding versus non-responding patients, or for the discovery of novel tumor antigens using TIL receptors as a tool. A major barrier to advancing this field of research is that only a small percentage of TILs in a tumor may be antigen specific, with a large background of non-specific immune cells present due to general inflammation.

Therefore it is critical to sample sufficient numbers of TCRs and BCRs to identify those specifically enriched in the tumor environment, a task likely to require many thousands of cells rather than the small numbers afforded by plate-based TIL analysis. In addition, since TILs have been reported to show non-canonical surface phenotypes, marker-based sorting may miss important TIL populations.

Several recent studies have reported compelling progress in scale-up of single cell transcriptome analysis although to date these have not demonstrated the read length or throughput of several hundred thousand cells per sample necessary for meaningful V(D)J capture of immune repertoires from heterogeneous samples. In particular, the methods of Klein et al. (InDrop) and Macosko et al. (Dropseq) allowed emulsion-based whole-transcriptome sequencing from several thousand cells. However, capture of full-length immune receptor genes presents a substantially different challenge, as well as requiring tens to hundreds of times more cells per experiment for adequate immune repertoire characterization than shown in those reports. The methods described herein are well suited to this application due to its higher throughput afforded by the use of emulsion droplets 15-75 times smaller than those of Dropseq and InDrop, and the generation of clonal droplet barcodes within the emulsion by PCR that removes the need for prior synthesis of barcoded beads by split-pool synthesis. In addition, since the method presented here involves both reverse transcription and PCR in the original emulsion droplets, a greater range of target types can be aimed at allowing mRNA, labeled protein and potentially genomic DNA to be captured simultaneously from single cells, while also minimizing the risk of post-emulsion cross-contamination between barcodes.

To date, all methods for targeted BCR or TCR sequencing suffer from at least one of the following limitations: unpaired receptor chains, low throughput of paired chains ($<10^4$ per experiment), or partial sequence recovery. In contrast the emulsion method presented here overcomes these limitations and displays a number of additional advantages. Firstly, linking the chains with short sequence barcodes, rather than physically splicing into long amplicons as performed by Dekosky et al. allows sequencing of the complete V(D)J variable region, ensuring comprehensive analysis of somatic mutations and allowing fully accurate functional reconstruction. Secondly, by dual barcoding both the mRNAs themselves and all products from a single cell, PCR and sequencing errors can be minimized and in particular the number of cells in each clonal lineage can be deconvoluted from the expression level within cells of that clone. This feature, applied here for the first time to immune repertoire analysis, overcomes the limitations of immune sequencing from bulk mRNA, which measures overall expression but not clonal abundance, as well as from genomic DNA, which reveals clonal abundance but nothing about expression. Third, this barcoding approach can be extended to additional genes of phenotypic value at both the mRNA and protein level, adding important information about the sub-types of T- and B-cells expressing each receptor sequence. The methods presented herein represent the first demonstration of simultaneous RNA sequencing with protein measurements from single cells in emulsion. This approach combines the type of information collected by flow cytometry with the digital resolution of immune sequencing, allowing direct linking of each cell's phenotype to its full-length receptor sequence. The method therefore promises to be a powerful addition to tumor receptor profiling, by revealing which T- and B-cell lineages represent particular cell sub-types and states such as immune suppression or "exhaustion", often a key indicator of anti-tumor reactivity. The approach could also be applied to discovery of antibodies specific for a desired antigen, by incubating B-cells with a DNA-barcoded target antigen prior to emulsion isolation and analysis.

In summary, natively paired BCRs and TCRs were recovered from thousands of TILs in a dissociated tumor sample, leading to identification of dozens of clonally expanded receptor lineages that are mutated, class-switched and highly expressed by the cells, strongly suggesting the specific recruitment of functionally active B and T cells to the tumor site. Taken alongside complementary approaches to identify the targets of TIL receptors found in this and other tumors, the technology described here should enable the discovery of novel tumor antigens, further our basic understanding of tumor immuno-biology, and provide a powerful tool to investigate the immune effects of emerging immunotherapies Determination of Natively Paired T-Cell Receptor Chains T cell receptor chain pairs and antibody immunoglobulin chain pairs are both types of immune receptors and are related evolutionarily. It is an object of the invention to generate polynucleotide libraries for high-throughput sequencing and diagnostics. It is also an object of the invention to develop human derived library panels for antibody and/or TCR discovery from patient or cohorts with specific common attributes. Starting material can be peripheral blood or from a tissue biopsy, from which immune cells are globally isolated or sub-sorted for naïve, memory and ASC if desired. The disclosed invention can be applied to multiple different types of paired variable sequences, e.g., T-cell receptor chain pairs and antibody immunoglobulin chain pairs.

Isolated cells, such as immune cells, can be encapsulated in vessels, such as water in oil emulsions (droplets), in such a way to create individual picoliter compartments containing a single immune cell or less per droplet. Millions of cells can be processed for each sample, such as a biological sample from a subject, allowing high throughput in single cell sequencing technology. The use of a solid support, such as a bead, can be avoided using the methods described herein. The need to generate two separate populations of vessels can also be avoided using the methods described herein. For example, libraries of sequences can be generated in a same or a single reaction, or in a single plurality or population of vessels. Polynucleotides complementary to cell polynucleotides, such as $V_H$ and $V_L$ antibody chains and/or $V\alpha/V\beta$ and $V\gamma/V\delta$ T-cell receptor (TCR) chains, are introduced during formation of the vessels. A polynucleotide harboring a vessel barcode can also be introduced during formation of the vessels. These vessel barcoded polynucleotides can carry degenerate barcodes such that each cell polynucleotide containing a vessel barcode contains a unique identity code corresponding to the vessel they are in. A plurality of polynucleotides harboring a molecular barcode can also be introduced during formation of the vessels. These molecular barcoded polynucleotides can carry degenerate barcodes such that each cell polynucleotide molecule containing a molecular barcode contains a unique identity code corresponding to a single cell polynucleotide molecule from which they came. The millions of single immune cells can be lysed inside the emulsion and cell transcripts, such as $V_H$ and $V_L$ and/or $V\alpha/V\beta$ and/or $V\gamma/V\delta$ chain transcripts, can be reverse transcribed or copied using primers, followed by tagging with a vessel barcode and a molecular barcode, and PCR amplification of the barcoded polynucleotides. Each $V_H$ and $V_L$ and/or $V\alpha/V\beta$ and/or $V\gamma/V\delta$ chain stemming from a single immune cell (e.g., a B-cell or T-cell) can be virtually linked to each other with the same vessel barcode identity.

The $V_H$ and $V_L$ and/or $V\alpha/V\beta$ and/or $V\gamma/V\delta$ chains can then be recovered from the vessels and PCR enriched in order to add next-generation sequencing (NGS) tags. The library can be sequenced using a high throughput sequencing platform followed by analysis of repertoire diversity, antibody frequency, CDR3 characterization, somatic hypermutation phylogeny analysis, etc. A database of correctly matched $V_H$ and $V_L$ and/or $V\alpha/V\beta$ and/or $V\gamma/V\delta$ pairs can be generated by deconvoluting the vessel and molecular barcode sequences. Because each single immune cell are isolated in their respective vessel, for each vessel barcode observed twice, the transcripts sequenced originated from the same emulsion droplets and therefore from a unique single cell. For each different molecular barcode observed, for sequences containing the same vessel barcode, the transcripts sequenced originated from a different transcript molecule from a single cell. For each same molecular barcode observed, for sequences containing the same vessel barcode, the transcripts sequenced originated from a same transcript molecule from a single cell (e.g., PCR duplicates).

In parallel to the sequencing, a library of $V_H$ and $V_L$ and/or $V\alpha/V\beta$ and/or $V\gamma/V\delta$ chains recovered from the vessels can be cloned into antibody expression vectors and co-transfected for yeast display screening. Cloning this identical library pool is the preferred method compared to splitting a biological sample at the beginning, as some rare immune cells would only be captured in one, or the other assay. The library of human derived $V_H$ and $V_L$ and/or $V\alpha$ and $V\beta$ and/or $V\gamma$ and $V\delta$ chains can be expressed regardless of correct or incorrect pair matching as with classic display assays. Yeast display can then be performed against one or more antigen targets to enrich for potential antibody candidates.

Positive candidate antibodies emerging from display technologies, such as a yeast display, can be sequenced and queried against the barcode database of matched pairs. Each yeast displayed $V_H$ and/or $V\alpha$ and/or $V\gamma$ chain can be matched back to its respective $V_L$ or $V\beta$ or $V\delta$ chain, respectively, and each yeast displayed $V_L$ and/or $V\beta$ and/or $V\delta$ chain can be matched back to its respective $V_H$ or $V\alpha$ or $V\gamma$ chain, respectively. These correctly paired candidates can be gene synthesized and expressed in mammalian cell lines and functionally validated against the target of interest. These candidates can be fully human antibodies and/or TCRs.

The term "antibody" herein thus is used in the broadest sense and includes polyclonal and monoclonal antibodies, including intact antibodies and functional (antigen-binding) antibody fragments thereof, including fragment antigen binding (Fab) fragments, F(ab')2 fragments, Fab' fragments, Fv fragments, recombinant IgG (rIgG) fragments, single chain antibody fragments, including single chain variable fragments (scFv), and single domain antibodies (e.g., sdAb, sdFv, nanobody) fragments. The term encompasses genetically engineered and/or otherwise modified forms of immunoglobulins, such as intrabodies, peptibodies, chimeric antibodies, fully human antibodies, humanized antibodies, and heteroconjugate antibodies, multispecific, e.g., bispecific, antibodies, diabodies, triabodies, and tetrabodies, tandem di-scFv, tandem tri-scFv. Unless otherwise stated, the term "antibody" should be understood to encompass functional antibody fragments thereof. The term also encompasses intact or full-length antibodies, including antibodies of any class or sub-class, including IgG and sub-classes thereof, IgM, IgE, IgA, and IgD.

The terms "complementarity determining region," and "CDR," synonymous with "hypervariable region" or "HVR," are known in the art to refer to non-contiguous sequences of amino acids within antibody variable regions, which confer antigen specificity and/or binding affinity. In general, there are three CDRs in each heavy chain variable region (CDR-H1, CDR-H2, CDR-H3) and three CDRs in each light chain variable region (CDR-L1, CDR-L2, CDR-L3). "Framework regions" and "FR" are known in the art to refer to the non-CDR portions of the variable regions of the heavy and light chains. In general, there are four FRs in each full-length heavy chain variable region (FR-H1, FR-H2, FR-H3, and FR-H4), and four FRs in each full-length light chain variable region (FR-L1, FR-L2, FR-L3, and FR-L4).

The precise amino acid sequence boundaries of a given CDR or FR can be readily determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme), Al-Lazikani et al., (1997) JMB 273,927-948 ("Chothia" numbering scheme), MacCallum et al., J. Mol. Biol. 262: 732-745 (1996), "Antibody-antigen interactions: Contact analysis and binding site topography," J. Mol. Biol. 262, 732-745." ("Contact" numbering scheme), Lefranc M P et al., "IMGT unique numbering for immunoglobulin and T cell receptor variable domains and Ig superfamily V-like domains," Dev Comp Immunol, 2003 January; 27(1):55-77 ("IMGT" numbering scheme), and Honegger A and Plückthun A, "Yet another numbering scheme for immunoglobulin variable domains: an automatic modeling and analysis tool," J Mol Biol, 2001 Jun. 8; 309(3):657-70, ("Aho" numbering scheme).

The boundaries of a given CDR or FR may vary depending on the scheme used for identification. For example, the Kabat scheme is based structural alignments, while the Chothia scheme is based on structural information. Numbering for both the Kabat and Chothia schemes is based upon the most common antibody region sequence lengths, with insertions accommodated by insertion letters, for example, "30a," and deletions appearing in some antibodies. The two schemes place certain insertions and deletions ("indels") at different positions, resulting in differential numbering. The Contact scheme is based on analysis of complex crystal structures and is similar in many respects to the Chothia numbering scheme.

Table A, below, lists exemplary position boundaries of CDR-L1, CDR-L2, CDR-L3 and CDR-H1, CDR-H2, CDR-H3 as identified by Kabat, Chothia, and Contact schemes, respectively (See, Kabat et al. (1991), Sequences of Proteins of Immunological Interest, 5th Ed. Public Health Service, National Institutes of Health, Bethesda, Md.; and A1-Lazikani et al., (1997) JMB 273,927-948). For CDR-H1, residue numbering is listed using both the Kabat and Chothia numbering schemes. FRs are located between CDRs, for example, with FR-L1 located between CDR-L1 and CDR-L2, and so forth. It is noted that because the shown Kabat numbering scheme places insertions at H35A and H35B, the end of the Chothia CDR-H1 loop when numbered using the shown Kabat numbering convention varies between H32 and H34, depending on the length of the loop.

TABLE A

| CDR | Kabat | Chothia | Contact |
| --- | --- | --- | --- |
| CDR-L1 | L24--L34 | L24--L34 | L30--L36 |
| CDR-L2 | L50--L56 | L50--L56 | L46--L55 |
| CDR-L3 | L89--L97 | L89--L97 | L89--L96 |
| CDR-H1 (Kabat Numbering[1]) | H31--H35B | H26--H32..34 | H30--H35B |
| CDR-H1 (Chothia Numbering[2]) | H31--H35 | H26--H32 | H30--H35 |
| CDR-H2 | H50--H65 | H52--H56 | H47--H58 |
| CDR-H3 | H95--H102 | H95--H102 | H93--H101 |

Thus, unless otherwise specified, a "CDR" or "complementary determining region," or individual specified CDRs (e.g., "CDR-H1, CDR-H2), of a given antibody or region thereof, such as a variable region thereof, should be understood to encompass a (or the specific) complementary determining region as defined by any of the aforementioned schemes. For example, where it is stated that a particular CDR (e.g., a CDR-H3) contains the amino acid sequence of a corresponding CDR in a given VH or VL amino acid sequence, it is understood that such a CDR has a sequence of the corresponding CDR (e.g., CDR-H3) within the variable region, as defined by any of the aforementioned schemes. In some embodiments, specified CDR sequences are specified.

Likewise, unless otherwise specified, a FR or individual specified FR(s) (e.g., FR-H1, FR-H2), of a given antibody or region thereof, such as a variable region thereof, should be understood to encompass a (or the specific) framework region as defined by any of the known schemes. In some instances, the scheme for identification of a particular CDR, FR, or FRs or CDRs is specified, such as the CDR as defined by the Kabat, Chothia, or Contact method. In other cases, the particular amino acid sequence of a CDR or FR is given.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three CDRs. (See, e.g., Kindt et al. Kuby Immunology, 6th ed., W.H. Freeman and Co., page 91 (2007). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., J. Immunol. 150: 880-887 (1993); Clarkson et al., Nature 352:624-628 (1991).

Among the provided antibodies are antibody fragments. An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments. In particular embodiments, the antibodies are single-chain antibody fragments comprising a variable heavy chain region and/or a variable light chain region, such as scFvs.

Unless otherwise stated, the term "TCR" should be understood to encompass full TCRs as well as antigen-binding portions or antigen-binding fragments (also called MHC-peptide binding fragments) thereof. In some embodiments, the TCR is an intact or full-length TCR. In some embodiments, the TCR is an antigen-binding portion that is less than a full-length TCR but that binds to a specific antigenic peptide bound to (i.e., in the context of) an MHC molecule, i.e., an MHC-peptide complex. In some cases, an antigen-binding portion or fragment of a TCR can contain only a portion of the structural domains of a full-length or intact TCR, but yet is able to bind the epitope (e.g., MHC-peptide complex) to which the full TCR binds. In some cases, an antigen-binding portion or fragment of a TCR contains the variable domains of a TCR, such as variable α chain and variable β chain of a TCR, sufficient to form a binding site for binding to a specific MHC-peptide complex, such as generally where each chain contains three complementarity determining regions. Polypeptides or proteins having a binding domain which is an antigen-binding domain or is homologous to an antigen-binding domain are included. Complementarity determining region (CDR) grafted antibodies and TCRs and other humanized antibodies and TCRs (including CDR modifications and framework region modifications) are also contemplated by these terms. It should be noted that while reference may be made only to immunoglobulin chains (e.g., heavy chains and lights chains), the disclosed invention can be applied to multiple other different types of paired sequences, e.g., T-cell receptor chain pairs (TCRα and TCRβ chains and TCRγ and TCRδ chains), and is not limited to immunoglobulins.

The ability of T-cells to recognize antigens associated with various cancers or infectious organisms is conferred by its TCR, which is made up of both an alpha (α) chain and a beta (β) chain or a gamma (γ) and a delta (δ) chain. The proteins which make up these chains are encoded by DNA, which employs a unique mechanism for generating the tremendous diversity of the TCR. This multi-subunit immune recognition receptor associates with the CD3 complex and binds peptides presented by the MHC class I and II proteins on the surface of antigen-presenting cells (APCs). Binding of a TCR to the antigenic peptide on the APC is a central event in T-cell activation, which occurs at an immunological synapse at the point of contact between the T-cell and the APC.

In some embodiments, the TCR, or other MHC-peptide binding molecule, recognizes or potentially recognizes the T cell epitope in the context of an MHC class I molecule. MHC class I proteins are expressed in all nucleated cells of higher vertebrates. The MHC class I molecule is a heterodimer composed of a 46-kDa heavy chain which is non-covalently associated with the 12-kDa light chain β-2 microglobulin. In humans, there are several MHC alleles, such as, for example, HLA-A2, HLA-A1, HLA-A3, HLA-A24, HLA-A28, HLA-A31, HLA-A33, HLA-A34, HLA-B7, HLA-B45 and HLA-Cw8. The sequences of MHC alleles are known and can be found, for example, at the IMGT/HLA database available at www.ebi.ac.uk/ipd/imgt/hla. In some embodiments, the MHC class I allele is an HLA-A2 allele, which in some populations is expressed by approximately 50% of the population. In some embodiments, the HLA-A2 allele can be an HLA-A*0201, *0202, *0203, *0206, or *0207 gene product. In some cases, there can be differences in the frequency of subtypes between different populations. For example, in some embodiments, more than 95% of the HLA-A2 positive Caucasian population is HLA-A*0201, whereas in the Chinese population the frequency has been reported to be approximately 23% HLA-A*0201, 45% HLA-A*0207, 8% HLA-A*0206 and 23% HLA-A*0203.

In some embodiments, the TCR, or other MHC-peptide binding molecule, recognizes or potentially recognizes the T cell epitope in the context of an MHC class II molecule. MHC class II proteins are expressed in a subset of nucleated vertebrate cells, generally called antigen presenting cells (APCs). In humans, there are several MHC class II alleles, such as, for example, DR1, DR3, DR4, DR7, DR52, DQ1, DQ2, DQ4, DQ8 and DP1. In some embodiments, the MHC class II allele that is HLA-DRB1*0101, an HLA-DRB*0301, HLA-DRB*0701, HLA-DRB*0401 an HLA-DQB1*0201. The sequences of MHC alleles are known and can be found, for example, at the IMGT/HLA database available at www.ebi.ac.uk/ipd/imgt/hla.

Each TCR comprises variable complementarity determining regions (CDRs), as well as framework regions (FRs). The amino acid sequence of the third complementarity-determining region (CDR3) loops of the α and β chain variable domains largely determines the sequence diversity of αβ T-cells arising from recombination between variable (Vβ), diversity (Dβ), and joining (Jβ) gene segments in the β chain locus, and between analogous Vα and Jα gene segments in the α chain locus, respectively. The existence of multiple such gene segments in the TCR α and β chain loci allows for a large number of distinct CDR3 sequences to be encoded. Independent addition and deletion of nucleotides at the Vβ-Dβ, Dβ-Jβ, and Vα-Jα junctions during the process of TCR gene rearrangement further increases CDR3 sequence diversity. In this respect, immunocompetence is reflected in the diversity of TCRs.

Immunoglobulins (Igs) expressed by B-cells are in some aspects proteins consisting of four polypeptide chains, two heavy chains (IgHs) and two light chains (IgLs), forming an $H_2L_2$ structure. Each pair of IgH and IgL chains contains a hypervariable domain, consisting of a $V_L$ and a $V_H$ region, and a constant domain. The IgH chains of Igs are of several types, μ, δ, γ, α, and β. The diversity of Igs within an individual is mainly determined by the hypervariable domain. Similar to the TCR, the V domain of IgH chains is created by the combinatorial joining of the $V_H$, $D_H$, and $J_H$ gene segments. Independent addition and deletion of nucleotides at the $V_H$-$D_H$, $D_H$-$J_H$, and $V_H$-$J_H$ junctions during the process of Ig gene rearrangement further increases hypervariable domain sequence diversity. Here, immunocompetence is reflected in the diversity of Igs.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three CDRs. (See, e.g., Kindt et al. Kuby Immunology, 6th ed., W.H. Freeman and Co., page 91 (2007). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., J. Immunol. 150: 880-887 (1993); Clarkson et al., Nature 352:624-628 (1991).

An "affinity portion" refers to the portion of the affinity-oligonucleotide conjugate that interacts with a target antigen. Exemplary affinity portions include antibodies, peptides, proteins, aptamers, small molecules, drugs, cells, and others.

A "hypervariable region" refers to the amino acid residues of an antibody or TCR which are responsible for antigen-binding. The hypervariable region comprises amino acid residues from a complementarity determining region or CDR. Framework or FR residues are those variable domain residues other than the hypervariable region residues as herein defined.

Among the provided antibodies are antibody fragments. An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, $F(ab')_2$; diabodies; linear antibodies; single-chain antibody molecules (e.g. scFv); and multispecific antibodies formed from antibody fragments. In particular embodiments, the antibodies are single-chain antibody fragments comprising a variable heavy chain region and/or a variable light chain region, such as scFvs.

Single-domain antibodies are antibody fragments comprising all or a portion of the heavy chain variable domain or all or a portion of the light chain variable domain of an antibody. In certain embodiments, a single-domain antibody is a human single-domain antibody.

Antibody fragments can be made by various techniques, including but not limited to proteolytic digestion of an intact antibody as well as production by recombinant host cells. In some embodiments, the antibodies are recombinantly-produced fragments, such as fragments comprising arrangements that do not occur naturally, such as those with two or more antibody regions or chains joined by synthetic linkers, e.g., peptide linkers, and/or that are may not be produced by enzyme digestion of a naturally-occurring intact antibody. In some aspects, the antibody fragments are scFvs.

Also provided are TCR fragments, including antigen-binding fragments. In some embodiments, the TCR is an antigen-binding portion thereof, such as a variant of a full-length TCR not containing the transmembrane and/or cytoplasmic region(s) thereof, which may be referred to as a full soluble TCR. In some embodiments, the TCR is a dimeric TCR (dTCR). In some embodiments, the TCR is a single-chain TCR (scTCR), such as a scTCR having a structure as described in PCT patent publication numbers WO 03/020763, WO 04/033685, or WO 2011/044186. In certain embodiments, the TCR is a single-chain TCR fragment comprising an alpha chain variable region linked to a beta chain variable region, such as a scTv. In some embodiments, an scTv is also referred to as an scFv.

A single-chain Fv or scFv refers in some aspects to antibody or TCR fragments that comprise the variable heavy chain ($V_H$) and variable light chain ($V_L$) domains of an antibody or the variable alpha or gamma chain (Vα or Vγ) and variable beta or delta chain (Vβ or Vδ) domains of a TCR, wherein these domains are present in a single polypeptide chain. Generally, the Fv polypeptide further comprises a polypeptide linker between the $V_H$ and $V_L$ domains or Vα and Vβ domains or Vγ and Vδ domains which enables the sFv to form the desired structure for antigen binding.

A diabody refers in some aspects to small antibody and/or TCR fragments with two antigen-binding sites, which fragments comprise a $V_H$ connected to a $V_L$ in the same polypeptide chain ($V_H$—$V_L$) or a Vα connected to a Vβ in the same polypeptide chain (Vα-Vβ) or a Vγ connected to a Vδ in the same polypeptide chain (Vγ-Vδ). By using a linker that is too short to allow pairing between the two domains on the same chain, the domains are forced to pair with the complementary domains of another chain and create two antigen-binding sites. Exemplary diabodies are described more fully in, for example, EP404097 and WO93111161.

A bispecific antibody or bispecific TCR refers in some aspects to an antibody or TCR that shows specificities to two different types of antigens. The terms as used herein specifically include, without limitation, antibodies and TCRs which show binding specificity for a target antigen and to another target that facilitates delivery to a particular tissue. Similarly, multi-specific antibodies and TCRs have two or more binding specificities.

A linear antibody or linear TCR refers in some aspects to a pair of tandem Fd segments (e.g., $V_H$—$C_{H1}$-$V_H$-$C_{H1}$ or Vα-Cα$_1$-Vα-Cα$_1$) which form a pair of antigen binding regions. Linear antibodies and TCRs can be bispecific or monospecific, for example, as described by Zapata et al., Protein Eng. 8(10):1057-1062 (1995).

An antigen-binding domain refers in some aspects to one or more fragments of an antibody or TCR that retain the ability to specifically bind to an antigen. Non-limiting examples of antibody fragments included within such terms include, but are not limited to, (i) a Fab fragment, a monovalent fragment consisting of the $V_L$, $V_H$, $C_L$ and $C_{H1}$ domains; (ii) a F(ab')$_2$ fragment, a bivalent fragment containing two Fab fragments linked by a disulfide bridge at the hinge region; (iii) a Fd fragment consisting of the $V_H$ and $C_{H1}$ domains; (iv) a Fv fragment containing the $V_L$ and $V_H$ domains of a single arm of an antibody, including scFvs, (v) a dAb fragment (Ward et al., (1989) Nature 341:544 546), which containing a $V_H$ domain; and (vi) an isolated CDR. Additionally included in this definition are antibodies comprising a single heavy chain and a single light chain or TCRs with a single alpha chain or a single beta chain.

"F(ab')$_2$" and "Fab'" moieties can be produced by treating an Ig with a protease such as pepsin and papain, and include antibody fragments generated by digesting immunoglobulin near the disulfide bonds existing between the hinge regions in each of the two heavy chains. For example, papain cleaves IgG upstream of the disulfide bonds existing between the hinge regions in each of the two heavy chains to generate two homologous antibody fragments in which a light chain composed of $V_L$ and $C_L$, and a heavy chain fragment composed of $V_H$ and $C_{H\gamma 1}$ (γ1 region in the constant region of the heavy chain) are connected at their C terminal regions through a disulfide bond. Each of these two homologous antibody fragments is called 'Fab'. Pepsin also cleaves IgG downstream of the disulfide bonds existing between the hinge regions in each of the two heavy chains to generate an antibody fragment slightly larger than the fragment in which the two above-mentioned 'Fab' are connected at the hinge region. This antibody fragment is called F('ab')$_2$. The Fab fragment also contains the constant domain of the light chain and the first constant domain ($C_H$1) of the heavy chain. 'Fab' fragments differ from Fab fragments by the addition of a few residues at the carboxyl terminus of the heavy chain $C_H$1 domain including one or more cysteine(s) from the antibody hinge region. Fab'-SH is the designation herein for Fab' in which the cysteine residue(s) of the constant domains bear a free thiol group. F(ab')$_2$ antibody fragments originally are produced as pairs of Fab' fragments which have hinge cysteines between them.

Fv refers in some aspects to an antibody or TCR fragment which contains a complete antigen-recognition and antigen-binding site. This region consists of a dimer of one heavy chain and one light chain variable domain or one TCRα chain and one TCRβ chain or one TCRγ chain and one TCRδ chain in tight, non-covalent association. It is in this configuration that the three CDRs of each variable domain interact to define an antigen-binding site on the surface of the $V_H$-$V_L$ dimer or Vα-Vβ dimer or Vγ-Vδ dimer. Collectively, a combination of one or more of the CDRs from each of the $V_H$ and $V_L$ chains or Vα-Vβ chains or Vγ-Vδ chains confers antigen-binding specificity to the antibody or TCR. For example, it would be understood that, for example, the CDRH3 and CDRL3 could be sufficient to confer antigen-binding specificity to an antibody or TCR when transferred to $V_H$ and $V_L$ chains or Vα and Vβ chains or Vγ-Vδ chains of a recipient selected antibody, TCR, or antigen-binding fragment thereof and this combination of CDRs can be tested for binding, affinity, etc. Even a single variable domain (or half of an Fv comprising only three CDRs specific for an antigen) has the ability to recognize and bind antigen, although likely at a lower affinity than when combined with a second variable domain. Furthermore, although the two domains of a Fv fragment ($V_L$ and $V_H$ or Vα and Vβ or Vγ and Vδ), are coded for by separate genes, they can be joined using recombinant methods by a synthetic linker that enables them to be made as a single protein chain in which the $V_L$ and $V_H$ or Vα and Vβ or Vγ and Vδ chain regions pair to form monovalent molecules (known as single chain Fv (scFv); Bird et al. (1988) Science 242:423-426; Huston et al. (1988) Proc. Natl. Acad. Sci. USA 85:5879-5883; and Osbourn et al. (1998) Nat. Biotechnol. 16:778). Such scFvs are also intended to be encompassed within the term "antigen-binding portion" of an antibody. Any $V_H$ and $V_L$ sequences of specific scFv can be linked to an Fc region cDNA or genomic sequences, in order to generate expression vectors encoding complete Ig (e.g., IgG) molecules or other isotypes. $V_H$ and $V_L$ can also be used in the generation of Fab, Fv or other fragments of Igs using either protein chemistry or recombinant DNA technology.

Antigen-binding polypeptides also include heavy chain dimers such as, for example, antibodies from camelids and sharks. Camelid and shark antibodies comprise a homodimeric pair of two chains of V-like and C-like domains (neither has a light chain). Since the $V_H$ region of a heavy chain dimer IgG in a camelid does not have to make hydrophobic interactions with a light chain, the region in the heavy chain that normally contacts a light chain is changed to hydrophilic amino acid residues in a camelid. $V_H$ domains of heavy-chain dimer IgGs are called $V_{HH}$ domains. Shark Ig-NARs comprise a homodimer of one variable domain (termed a V-NAR domain) and five C-like constant domains (C-NAR domains). In camelids, the diversity of antibody repertoire is determined by the CDRs 1, 2, and 3 in the $V_H$ or $V_{HH}$ regions. The CDR3 in the camel $V_{HH}$ region is characterized by its relatively long length, averaging 16 amino acids (Muyldermans et al., 1994, Protein Engineering 7(9): 1129).

A "humanized" antibody is an antibody in which all or substantially all CDR amino acid residues are derived from non-human CDRs and all or substantially all FR amino acid residues are derived from human FRs. A humanized antibody optionally may include at least a portion of an antibody constant region derived from a human antibody. A "humanized form" of a non-human antibody, refers to a variant of the non-human antibody that has undergone humanization, typically to reduce immunogenicity to humans, while retaining the specificity and affinity of the parental non-human antibody. In some embodiments, some FR residues in a humanized antibody are substituted with corresponding residues from a non-human antibody (e.g., the antibody from which the CDR residues are derived), e.g., to restore or improve antibody specificity or affinity.

Among the provided antibodies are human antibodies. A "human antibody" is an antibody with an amino acid sequence corresponding to that of an antibody produced by a human or a human cell, or non-human source that utilizes human antibody repertoires or other human antibody-encoding sequences, including human antibody libraries. The term excludes humanized forms of non-human antibodies comprising non-human antigen-binding regions, such as those in which all or substantially all CDRs are non-human.

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic animals, the endogenous immunoglobulin loci have generally been inactivated. Human antibodies also may be derived from human antibody libraries, including phage display and cell-free libraries, containing antibody-encoding sequences derived from a human repertoire.

Among the provided antibodies are monoclonal antibodies, including monoclonal antibody fragments. The term "monoclonal antibody" as used herein refers to an antibody obtained from or within a population of substantially homogeneous antibodies, i.e., the individual antibodies comprising the population are identical, except for possible variants containing naturally occurring mutations or arising during production of a monoclonal antibody preparation, such variants generally being present in minor amounts. In contrast to polyclonal antibody preparations, which typically include different antibodies directed against different epitopes, each monoclonal antibody of a monoclonal antibody preparation is directed against a single epitope on an antigen. The term is not to be construed as requiring production of the antibody by any particular method. A monoclonal antibody may be made by a variety of techniques, including but not limited to generation from a hybridoma, recombinant DNA methods, phage-display and other antibody display methods.

The terms "polypeptide" and "protein" are used interchangeably to refer to a polymer of amino acid residues, and are not limited to a minimum length. Polypeptides, including the provided antibodies and antibody chains and other peptides, e.g., linkers and binding peptides, may include amino acid residues including natural and/or non-natural amino acid residues. The terms also include post-expression modifications of the polypeptide, for example, glycosylation, sialylation, acetylation, phosphorylation, and the like. In some aspects, the polypeptides may contain modifications with respect to a native or natural sequence, as long as the protein maintains the desired activity. These modifications may be deliberate, as through site-directed mutagenesis, or may be accidental, such as through mutations of hosts which produce the proteins or errors due to PCR amplification.

A "germline sequence" refers to a genetic sequence from the germline (the haploid gametes and those diploid cells from which they are formed). Germline DNA contains multiple gene segments that encode a single Ig heavy or light chain, or a single TCRα or TCRβ chain, or a single TCRγ or TCRδ chain. These gene segments are carried in the germ cells but cannot be transcribed and translated until they are arranged into functional genes. During B-cell and T-cell differentiation in the bone marrow, these gene segments are randomly shuffled by a dynamic genetic system capable of generating more than $10^8$ specificities. Most of these gene segments are published and collected by the germline database.

Affinity refers to the equilibrium constant for the reversible binding of two agents and is expressed as $K_D$. Affinity of a binding protein to a ligand such as affinity of an antibody for an epitope can be, for example, from about 100 nanomolar (nM) to about 0.1 nM, from about 100 nM to about 1 picomolar (pM), or from about 100 nM to about 1 femtomolar (fM). The term "avidity" refers to the resistance of a complex of two or more agents to dissociation after dilution.

An epitope refers in some aspects to a portion of an antigen or other macromolecule capable of forming a binding interaction with the variable region binding pocket of an antibody or TCR. Such binding interactions can be manifested as an intermolecular contact with one or more amino acid residues of one or more CDRs. Antigen binding can involve, for example, a CDR3, a CDR3 pair, or in some instances, interactions of up to all six CDRs of the $V_H$ and $V_L$ chains. An epitope can be a linear peptide sequence (i.e., "continuous") or can be composed of noncontiguous amino acid sequences (i.e., "conformational" or "discontinuous"). An antibody or TCR can recognize one or more amino acid sequences; therefore an epitope can define more than one distinct amino acid sequence. In some aspects, a TCR can recognize one or more amino acid sequences or epitopes in the context of an MHC. Epitopes recognized by antibodies and TCRs can be determined by peptide mapping and sequence analysis techniques well known to one of skill in the art. Binding interactions are manifested as intermolecular contacts with one or more amino acid residues of a CDR.

In some embodiments, reference to an antibody or TCR with specific binding refers to a situation in which an antibody or TCR will not show any significant binding to molecules other than the antigen containing the epitope recognized by the antibody or TCR. The term is also applicable where for example, an antigen binding domain is specific for a particular epitope which is carried by a number of antigens, in which case the selected antibody, TCR, or antigen-binding fragment thereof carrying the antigen binding domain will be able to bind to the various antigens carrying the epitope. The terms "preferentially binds" or "specifically binds" mean that the antibodies, TCRs, or fragments thereof bind to an epitope with greater affinity than it binds unrelated amino acid sequences, and, if cross-reactive to other polypeptides containing the epitope, are not toxic at the levels at which they are formulated for administration to human use. In one aspect, such affinity is at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1000-fold greater than the affinity of the antibody, TCR, or fragment thereof for unrelated amino acid sequences. The term "binding" refers to a direct association between two molecules, due to, for example, covalent, electrostatic, hydrophobic, and ionic and/or hydrogen-bond interactions under physiological conditions, and includes interactions such as salt bridges and water bridges, as well as any other conventional means of binding.

Pharmaceutically acceptable refers to molecular entities and compositions that are physiologically tolerable and do not typically produce an allergic or similar untoward reaction, such as gastric upset, dizziness and the like, when administered to a human.

A unit dose when used in reference to a therapeutic composition refers to physically discrete units suitable as unitary dosage for humans, each unit containing a predetermined quantity of active material calculated to produce the desired therapeutic effect in association with the required diluent; i.e., carrier, or vehicle.

A packaging material refers to a physical structure housing the components of the kit. The packaging material can maintain the components sterilely and can be made of material commonly used for such purposes (e.g., paper, corrugated fiber, glass, plastic, foil, ampules, etc.). The label or packaging insert can include appropriate written instructions. Kits, therefore, can additionally include labels or instructions for using the kit components in any method of the invention. A kit can include a compound in a pack, or dispenser together with instructions for administering the compound in a method described herein.

Prevention refers to prophylaxis, prevention of onset of symptoms, prevention of progression of a disease or disorder associated with excess levels of protein or correlated with protein activity.

Inhibition, "treatment" and "treating" are used interchangeably and refer to, for example, stasis of symptoms, prolongation of survival, partial or full amelioration of symptoms, and partial or full eradication of a condition, disease or disorder associated with excess levels of protein or correlated with protein activity. For example, treatment of cancer includes, but is not limited to, stasis, partial or total elimination of a cancerous growth or tumor. Treatment or partial elimination includes, for example, a fold reduction in growth or tumor size and/or volume such as about 2-fold, about 3-fold, about 4-fold, about 5-fold, about 10-fold, about 20-fold, about 50-fold, or any fold reduction in between. Similarly, treatment or partial elimination can include a percent reduction in growth or tumor size and/or volume of about 1%, 2%, 3%, 4%, 5%, 10%, 20%, 30%, 40%, 50%, 60%, 70%, 80%, 90%, 95% or any percentage reduction in between.

A neutralizing antibody or neutralizing TCR refers in some aspects to any antibody or TCR that inhibits replication of a pathogen, such as a virus or bacteria, regardless of the mechanism by which neutralization is achieved.

An antibody repertoire or TCR repertoire refers to a collection of antibodies, TCR, or fragments thereof. An antibody repertoire can, for example, be used to select a particular antibody or screen for a particular property, such as binding ability, binding specificity, ability of gastrointestinal transport, stability, affinity, and the like. The term specifically includes antibody and TCR libraries, including all forms of combinatorial libraries, such as, for example, antibody phage display libraries, including, without limitation, single-chain Fv (scFv) and Fab antibody phage display libraries from any source, including naïve, synthetic and semi-synthetic libraries.

A "target nucleic acid molecule," "target molecule," "target polynucleotide," "target polynucleotide molecule," refers to any nucleic acid of interest.

A polymerase chain reaction (PCR) refers to an in vitro amplification reaction of polynucleotide sequences by the simultaneous primer extension of complementary strands of a double stranded polynucleotide. PCR reactions produce copies of a template polynucleotide flanked by primer binding sites. The result, with two primers, is an exponential increase in template polynucleotide copy number of both strands with each cycle, because with each cycle both strands are replicated. The polynucleotide duplex has termini corresponding to the ends of primers used. PCR can comprise one or more repetitions of denaturing a template polynucleotide, annealing primers to primer binding sites, and extending the primers by a DNA or RNA polymerase in the presence of nucleotides. Particular temperatures, durations at each step, and rates of change between steps depend on many factors well-known to those of ordinary skill in the art. (McPherson et al., IRL Press, Oxford (1991 and 1995)). For example, in a conventional PCR using Taq DNA polymerase, a double stranded template polynucleotide can be denatured at a temperature >90° C., primers can be annealed at a temperature in the range 50-75° C., and primers can be extended at a temperature in the range 72-78° C. In some embodiments, PCR comprises Reverse transcription PCR (RT-PCR), real-time PCR, nested PCR, quantitative PCR, multiplexed PCR, or the like. In some embodiments, PCR does not comprise RT-PCR. (U.S. Pat. Nos. 5,168,038, 5,210,015, 6,174,670, 6,569,627, and 5,925,517; Mackay et al., Nucleic Acids Research, 30: 1292-1305 (2002)). RT-PCR comprises a PCR reaction preceded by a reverse transcription reaction and a resulting cDNA is amplified, Nested PCR comprises a two-stage PCR wherein an amplicon of a first PCR reaction using a first set of primers becomes the sample for a second PCR reaction using a second primer set, at least one of which binds to an interior location of an amplicon of a first PCR reaction. Multiplexed PCR comprises a PCR reaction, wherein a plurality of polynucleotide sequences is subjected to PCR in the same reaction mixture simultaneously. PCR reaction volumes can be anywhere from 0.2 pL-1000 µL. Quantitative PCR comprises a PCR reaction designed to measure an absolute or relative amount, abundance, or concentration of one or more sequences in a sample. Quantitative measurements can include comparing one or more reference sequences or standards to a polynucleotide sequence of interest. (Freeman et al., Biotechniques, 26: 112-126 (1999); Becker-Andre et al., Nucleic Acids Research, 17: 9437-9447 (1989); Zimmerman et al., Biotechniques, 21: 268-279 (1996); Diviacco et al., Gene, 122: 3013-3020 (1992); Becker-Andre et al., Nucleic Acids Research, 17: 9437-9446 (1989)).

In other embodiments, the methods, kits, and compositions disclosed herein may comprise a support. In some embodiments, the methods, kits, and compositions disclosed herein do not comprise a support. Typically, a solid support comprises one or more materials comprising one or more rigid or semi-rigid surfaces. In some embodiments, the support is a non-solid support. The support or substrate may comprise a membrane, paper, plastic, coated surface, flat surface, glass, slide, chip, or any combination thereof. In some embodiments, one or more surfaces of a support are substantially flat, although in some embodiments it may be desirable to physically separate synthesis regions for different compounds with, for example, wells, raised regions, pins, etched trenches, or the like. In some embodiments, solid supports comprise beads, resins, gels, microspheres, or other geometric configurations. Alternatively, solid supports can comprises silica chips, microparticles, nanoparticles, plates, and arrays. The solid support can comprise the use of beads that self-assemble in microwells. For example, the solid support comprises Illumina's BeadArray Technology. Alternatively, the solid support comprises Abbott Molecular's Bead Array technology, and Applied Microarray's FlexiPlex™ system. In other instances, the solid support is a plate. Examples of plates include, but are not limited to, MSD multi-array plates, MSD Multi-Spot® plates, microplate, ProteOn microplate, AlphaPlate, DELFIA plate, IsoPlate, and LumaPlate. In some embodiments, a support can comprise a plurality of beads. In some embodiments, a support can comprise an array. In some embodiments, a support can comprise a glass slide. Methods, substrates, and techniques applicable to polymers (U.S. Pat. Nos. 5,744,305, 5,143,854, 5,242,974, 5,252,743, 5,324,633, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846 and 6,428,752; US Patent Pub. Nos. 20090149340, 20080038559, 20050074787; and in PCT Publication Nos. WO 00/58516, WO 99/36760, and WO 01/58593). The attachment of the polynucleotides to a support may comprise amine-thiol crosslinking, maleimide crosslinking, N-hydroxysuccinimide or N-hydroxysulfosuccinimide, Zenon or SiteClick. Attaching the labeled nucleic acids to the support may comprise attaching biotin to the plurality of polynucleotides and coating the one or more beads with streptavidin. In some embodiments, the solid support is a bead. Examples of beads include, but are not limited to, streptavidin beads, agarose beads, magnetic beads, Dynabeads®, MACS® microbeads, antibody conjugated beads (e.g., anti-immunoglobulin microbead), protein A conjugated beads, protein G conjugated beads, protein A/G conjugated beads, protein L conjugated beads, polynucleotide dT conjugated beads, silica beads, silica-like beads, anti-biotin microbead, anti-fluorochrome microbead, and BcMag™ Carboxy-Terminated Magnetic Beads. The diameter of the beads may be about 5 mm, 10 µm, 20 µm, 25 µm, 30 µm, 35 µm, 40 µm, 45 µm or 50 µm. The solid support may be an array or microarray. The solid support may comprise discrete regions. The solid support may be an array, e.g., an addressable array.

"Nucleotide," "nucleoside," "nucleotide residue," and "nucleoside residue," as used herein, can mean a deoxyribonucleotide or ribonucleotide residue, or other similar nucleoside analogue capable of serving as a component of a primer suitable for use in an amplification reaction (e.g., PCR reaction). Such nucleosides and derivatives thereof can be used as the building blocks of the primers described herein, except where indicated otherwise. Nothing in this application is meant to preclude the utilization of nucleoside derivatives or bases that have been chemical modified to enhance their stability or usefulness in an amplification reaction, provided that the chemical modification does not interfere with their recognition by a polymerase as deoxyguanine, deoxycytosine, deoxythymidine, or deoxyadenine, as appropriate. In some embodiments, nucleotide analogs can stabilize hybrid formation. In some embodiments, nucleotide analogs can destabilize hybrid formation. In some embodiments, nucleotide analogs can enhance hybridization specificity. In some embodiments, nucleotide analogs can reduce hybridization specificity.

A "nucleic acid", or grammatical equivalents, refers to either a single nucleotide or at least two nucleotides covalently linked together.

A "polynucleotide" or "polynucleotide" or "polynucleotide" or grammatical equivalents refers to at least two nucleotides covalently linked together. A polynucleotide comprises a molecule containing two or more nucleotides. A polynucleotide comprises polymeric form of nucleotides of any length, either ribonucleotides, deoxyribonucleotides or peptide nucleic acids (PNAs), that comprise purine and pyrimidine bases, or other natural, chemically or biochemically modified, non-natural, or derivatives of nucleotide bases. The backbone of the polynucleotide can comprise sugars and phosphate groups, or modified or substituted sugar or phosphate groups. A polynucleotide may comprise modified nucleotides, such as methylated nucleotides and nucleotide analogs. The sequence of nucleotides may be interrupted by non-nucleotide components. A polynucleotide can include other molecules, such as another hybridized polynucleotide. Polynucleotides include sequences of deoxyribonucleic acid (DNA), ribonucleic acid (RNA), or both. Non-limiting examples of polynucleotides include a gene, a gene fragment, an exon, an intron, intergenic DNA (including, without limitation, heterochromatic DNA), messenger RNA (mRNA), transfer RNA, ribosomal RNA, ribozymes, small interfering RNA (siRNA), cDNA, recombinant polynucleotides, branched polynucleotides, plasmids, vectors, isolated DNA of a sequence, isolated RNA of a sequence, nucleic acid probes, and primers. Polynucleotides can be isolated from natural sources, recombinant, or artificially synthesized.

Polynucleotides can include nonstandard nucleotides, such as nucleotide analogs or modified nucleotides. In some embodiments, nonstandard nucleotides can stabilize hybrid formation. In some embodiments, nonstandard nucleotides can destabilize hybrid formation. In some embodiments, nonstandard nucleotides can enhance hybridization specificity. In some embodiments, nonstandard nucleotides can reduce hybridization specificity. Examples of nonstandard nucleotide modifications include 2' O-Me, 2' O-allyl, 2' O-propargyl, 2' O-alkyl, 2' fluoro, 2' arabino, 2' xylo, 2' fluoro arabino, phosphorothioate, phosphorodithioate, phosphoroamidates, 2' Amino, 5-alkyl-substituted pyrimidine, 3' deoxyguanosine, 5-halo-substituted pyrimidine, alkyl-substituted purine, halo-substituted purine, bicyclic nucleotides, 2'MOE, PNA molecules, LNA-molecules, LNA-like molecules, diaminopurine, S2T, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N⁶-adenine, 7-methyl guanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxy acetic acid (v), 5-methyl-2-thiouracil, 3-(3-amino-3-N-2-carboxypropyl) uracil, (acp3)w, 2,6-diaminopurine, and derivatives thereof.

A "subject", "individual", "host" or "patient" refers to a living organisms such as mammals. Examples of subjects and hosts include, but are not limited to, horses, cows, camels, sheep, pigs, goats, dogs, cats, rabbits, guinea pigs, rats, mice (e.g., humanized mice), gerbils, non-human primates (e.g., macaques), humans and the like, non-mammals, including, e.g., non-mammalian vertebrates, such as birds (e.g., chickens or ducks) fish (e.g., sharks) or frogs (e.g., *Xenopus*), and non-mammalian invertebrates, as well as transgenic species thereof. In certain aspects, a subject refers to a single organism (e.g., human). In certain aspects, or a group of individuals composing a small cohort having either a common immune factor to study and/or disease, and/or a cohort of individuals without the disease (e.g., negative/ normal control) are provided. A subject from whom samples are obtained can either be inflicted with a disease and/or disorder (e.g., one or more allergies, infections, cancers or autoimmune disorders or the like) and can be compared against a negative control subject which is not affected by the disease.

A "kit" refers to a delivery system for delivering materials or reagents for carrying out a method disclosed herein. In some embodiments, kits include systems that allow for the storage, transport, or delivery of reaction reagents (e.g., probes, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. Such contents may be delivered to the intended recipient together or separately. For example, a first container may contain an enzyme for use in an assay, while a second container contains a plurality of primers.

A polypeptide refers in some aspects to a molecule comprising at least two amino acids. In some embodiments, the polypeptide consists of a single peptide. In some embodiments, a polypeptide comprises two or more peptides. For example, a polypeptide can comprise at least about 2, 3, 4, 5, 6, 7, 8, 9, 10, 11, 12, 13, 14, 15, 16, 17, 18, 19, 20, 30, 40, 50, 60, 70, 80, 90, 100, 200, 300, 400, 500, 600, 700, 800, 900, or 1000 peptides or amino acids. Examples of polypeptides include, but are not limited to, amino acid chains, proteins, peptides, hormones, polypeptide saccharides, lipids, glycolipids, phospholipids, antibodies, enzymes, kinases, receptors, transcription factors, and ligands.

A sample refers in some aspects to a biological, environmental, medical, subject, or patient sample or a sample containing a polynucleotide, such as a target polynucleotide. Samples Any biological sample containing polynucleotides can be used in the methods described herein. For example, a sample can be a biological sample from a subject containing RNA or DNA. The polynucleotides can be extracted from the biological sample, or the sample can be directly subjected to the methods without extraction or purification of the polynucleotides. The sample can be extracted or isolated DNA or RNA. A sample can also be total RNA or DNA extracted from a biological specimen, a cDNA library, viral, or genomic DNA. In one embodiment, polynucleotides are isolated from a biological sample containing a variety of other components, such as proteins, lipids and non-template nucleic acids. Nucleic acid template molecules can be obtained from any cellular material, obtained from an animal, plant, bacterium, fungus, or any other cellular organism. In certain embodiments, the polynucleotides are obtained from a single cell. Polynucleotides can be obtained directly from an organism or from a biological sample obtained from an organism. Any tissue or body fluid specimen may be used as a source for nucleic acid for use in the invention. Polynucleotides can also be isolated from cultured cells, such as a primary cell culture or a cell line. The cells or tissues from which template nucleic acids are obtained can be infected with a virus or other intracellular pathogen.

In certain embodiments, antibody or TCR-producing immune cells can be isolated from the blood or other biological samples of a subject or host, such as a human or other animal, such as a human or other animal that has been immunized or that is suffering from an infection, cancer, an autoimmune condition, or any other diseases to identify a pathogen-, tumor-, and/or disease specific antibody or TCR of potential clinical significance. For example, the human may be diagnosed with a disease, be exhibiting symptoms of a disease, not be diagnosed with a disease, or not be exhibiting symptoms of a disease. For example, the human may be one that was exposed to and/or who can make useful antibodies or TCRs against an infectious agent (e.g., viruses, bacteria, parasites, prions, etc), antigen, or disease. For example, the animal may be one that was exposed to and/or who can make useful antibodies or TCRs against an infectious agent (e.g., viruses, bacteria, parasites, prions, etc), antigen, or disease. Certain immune cells from immunized hosts make antibodies or TCRs to one or more target antigens in question and/or one or more unknown antigens. In the present invention the lymphocyte pool can be enriched for the desired immune cells by any suitable method, such as screening and sorting the cells using fluorescence-activated cell sorting (FACS), magnetic activated cell sorting (MACS), panning or other screening method to generate a plurality of immune cells from a sample, such as an immune cell library, before antibody chains are sequenced, antibodies are made, or an expression library is/are made. In contrast to prior art enrichment methods, which provide only a few subsets of immune cells expressing different antibodies, and therefore only a few naturally occurring combinations of variable domains, the immune cell library of the present invention contains at least 2 subsets of or individual immune cells expressing different antibodies or TCRs. For example, the immune cell library of the present invention can contain at least 5, 10, 100, 250, 500, 750, 1000, 2500, 5000, 10000, 25000, 50000, 75000, 10000, 250000, 500000, 750000, 1000000, 2500000, 5000000, 7500000, or 10000000 subsets of or individual immune cells expressing different antibodies or TCRs. The methods of the present invention maximize immune cell recovery, and afford very high diversity.

In some embodiments, immune cells from non-immunized human or non-human donors are utilized. The naive repertoire of an animal (the repertoire before antigen challenge) provides the animal with antibodies or TCRs that can bind with moderate affinity ($K_A$ of about $1\times10^{-6}$ to $1\times10^{-7}$M) to essentially any non-self molecule. The sequence diversity of antibody or TCR binding sites is not encoded directly in the germline but is assembled in a combinatorial manner from V gene segments. Immunizations trigger any immune cell making a $V_H$-$V_L$ or Vα-Vβ or Vγ-Vδ combination that binds the immunogen to proliferate (clonal expansion) and to secrete the corresponding antibody as noted above. However, the use of spleen cells and/or immune cells or other peripheral blood lymphocytes (PBLs) from an unimmunized subject can provide a better representation of the possible antibody or TCR repertoire, and also permits the construction of a subsequent B-cell or T-cell antibody or TCR library using any animal species.

In some cases, in order to obtain sufficient nucleic acid for testing, a blood volume of at least 0.001, 0.005, 0.01, 0.05, 0.1, 0.5, 1, 2, 3, 4, 5, 10, 20, 25, 30, 35, 40, 45, or 50 mL is drawn.

In some cases, the starting material is peripheral blood. The peripheral blood cells can be enriched for a particular cell type (e.g., mononuclear cells; red blood cells; CD4$^+$ cells; CD8$^+$ cells; immune cells; T cells, NK cells, or the like). The peripheral blood cells can also be selectively depleted of a particular cell type (e.g., mononuclear cells; red blood cells; CD4$^+$ cells; CD8$^+$ cells; immune cells; T cells, NK cells, or the like).

In some cases, the starting material can be a tissue sample comprising a solid tissue, with non-limiting examples including brain, liver, lung, kidney, prostate, ovary, spleen, lymph node (including tonsil), thyroid, pancreas, heart, skeletal muscle, intestine, larynx, esophagus, and stomach. In other cases, the starting material can be cells containing nucleic acids, immune cells, and in particular B-cells or T-cells. In some cases, the starting material can be a sample containing nucleic acids, from any organism, from which genetic material can be obtained. In some cases, a sample is a fluid, e.g., blood, saliva, lymph, or urine.

A sample can be taken from a subject with a condition. In some cases, the subject from whom a sample is taken can be a patient, for example, a cancer patient or a patient suspected of having cancer. The subject can be a mammal, e.g., a human, and can be male or female. In some cases, the female is pregnant. The sample can be a tumor biopsy. The biopsy can be performed by, for example, a health care provider, including a physician, physician assistant, nurse, veterinarian, dentist, chiropractor, paramedic, dermatologist, oncologist, gastroenterologist, or surgeon.

In some cases, non-nucleic acid materials can be removed from the starting material using enzymatic treatments (such as protease digestion).

In some cases, blood can be collected into an apparatus containing a magnesium chelator including but not limited to EDTA, and is stored at 4° C. Optionally, a calcium chelator, including but not limited to EGTA, can be added. In another case, a cell lysis inhibitor is added to the blood including but not limited to formaldehyde, formaldehyde derivatives, formalin, glutaraldehyde, glutaraldehyde derivatives, a protein cross-linker, a nucleic acid cross-linker, a protein and nucleic acid cross-linker, primary amine reactive crosslinkers, sulfhydryl reactive crosslinkers, sulfhydryl addition or disulfide reduction, carbohydrate reactive crosslinkers, carboxyl reactive crosslinkers, photoreactive crosslinkers, or cleavable crosslinkers.

In some cases when the extracted material comprises single-stranded RNA, double-stranded RNA, or DNA-RNA hybrid, these molecules can be converted to double-stranded DNA using techniques known in the field. For example, reverse transcriptase can be employed to synthesize DNA from RNA molecules. In some cases, conversion of RNA to DNA can require a prior ligation step, to ligate a linker fragment to the RNA, thereby permitting use of universal primers to initiate reverse transcription. In other cases, the poly-A tail of an mRNA molecule, for example, can be used to initiate reverse transcription. Following conversion to DNA, the methods detailed herein can be used, in some cases, to further capture, select, tag, or isolate a desired sequence.

Nucleic acid molecules include deoxyribonucleic acid (DNA) and/or ribonucleic acid (RNA). Nucleic acid molecules can be synthetic or derived from naturally occurring sources. In one embodiment, nucleic acid molecules are isolated from a biological sample containing a variety of other components, such as proteins, lipids and non-template nucleic acids. Nucleic acid template molecules can be obtained from any cellular material, obtained from an animal, plant, bacterium, fungus, or any other cellular organism. In certain embodiments, the nucleic acid molecules are obtained from a single cell. Biological samples for use in the present invention include viral particles or preparations. Nucleic acid molecules can be obtained directly from an organism or from a biological sample obtained from an organism, e.g., from blood, urine, cerebrospinal fluid, seminal fluid, saliva, sputum, stool and tissue. Any tissue or body fluid specimen may be used as a source for nucleic acid for use in the invention. Nucleic acid molecules can also be isolated from cultured cells, such as a primary cell culture or a cell line. The cells or tissues from which template nucleic acids are obtained can be infected with a virus or other intracellular pathogen.

A sample can also be total RNA extracted from a biological specimen, a cDNA library, viral, or genomic DNA. In certain embodiments, the nucleic acid molecules are bound as to other target molecules such as proteins, enzymes, substrates, antibodies, binding agents, beads, small molecules, peptides, or any other molecule Generally, nucleic acid can be extracted from a biological sample by a variety of techniques such as those described by Sambrook and Russell, Molecular Cloning: A Laboratory Manual, Third Edition, Cold Spring Harbor, N.Y. (2001). Nucleic acid molecules may be single-stranded, double-stranded, or double-stranded with single-stranded regions (for example, stem- and loop-structures).

Methods of DNA extraction are well-known in the art. A classical DNA isolation protocol is based on extraction using organic solvents such as a mixture of phenol and chloroform, followed by precipitation with ethanol (J. Sambrook et al., "Molecular Cloning: A Laboratory Manual," 1989, 2nd Ed., Cold Spring Harbour Laboratory Press: New York, N.Y.). Other methods include: salting out DNA extraction (P. Sunnucks et al., Genetics, 1996, 144: 747-756; S. M. Aljanabi et al., Nucl. Acids Res. 1997, 25: 4692-4693), trimethylammonium bromide salts DNA extraction (S. Gustincich et al., BioTechniques, 1991, 11: 298-302) and guanidinium thiocyanate DNA extraction (J. B. W. Hammond et al., Biochemistry, 1996, 240: 298-300). A variety of kits are commercially available for extracting DNA from biological samples (e.g., BD Biosciences Clontech (Palo Alto, Calif.): Epicentre Technologies (Madison, Wis.); Gentra Systems, Inc. (Minneapolis, Minn.); MicroProbe Corp. (Bothell, Wash.); Organon Teknika (Durham, N.C.); and Qiagen Inc. (Valencia, Calif.)).

Methods of RNA extraction are also well known in the art (e.g., J. Sambrook et al., "Molecular Cloning: A Laboratory Manual" 1989, 211d Ed., Cold Spring Harbour Laboratory Press: New York) and kits for RNA extraction from bodily fluids are commercially available (e.g., Ambion, Inc. (Austin, Tex.); Amersham Biosciences (Piscataway, N.J.); BD Biosciences Clontech (Palo Alto, Calif.); BioRad Laboratories (Hercules, Calif.); Dynal Biotech Inc. (Lake Success, N.Y.); Epicentre Technologies (Madison, Wis.); Gentra Systems, Inc. (Minneapolis, Minn.); GIBCO BRL (Gaithersburg, Md.); Invitrogen Life Technologies (Carlsbad, Calif.); MicroProbe Corp. (Bothell, Wash.); Organon Teknika (Durham, N.C.); Promega, Inc. (Madison, Wis.); and Qiagen Inc. (Valencia, Calif.)).

One or more samples can be from one or more sources. One or more of samples may be from two or more sources. One or more of samples may be from one or more subjects. One or more of samples may be from two or more subjects. One or more of samples may be from the same subject. One or more subjects may be from the same species. One or more subjects may be from different species. The one or more subjects may be healthy. The one or more subjects may be affected by a disease, disorder or condition.

In some embodiments, a sample is a fluid, such as blood, saliva, lymph, urine, cerebrospinal fluid, seminal fluid, sputum, stool, or tissue homogenates.

A sample can be taken from a subject with a condition. In some embodiments, the subject from whom a sample is taken can be a patient, for example, a cancer patient or a patient suspected of having cancer. The subject can be a mammal, e.g., a human, and can be male or female. In some embodiments, the female is pregnant. The sample can be a tumor biopsy. The biopsy can be performed by, for example, a health care provider, including a physician, physician assistant, nurse, veterinarian, dentist, chiropractor, paramedic, dermatologist, oncologist, gastroenterologist, or surgeon.

In some embodiments, the polynucleotides are bound to other target molecules such as proteins, enzymes, substrates, antibodies, binding agents, beads, small molecules, peptides, or any other molecule. In some embodiments, the polynucleotides are not bound to a solid support. Nucleic acids can be extracted from a biological sample by a variety of techniques (Sambrook et al., Molecular Cloning: A Laboratory Manual, Third Edition, Cold Spring Harbor, N.Y. (2001)).

In some embodiments, the sample is saliva. In some embodiments, the sample is whole blood. In some embodiments, in order to obtain sufficient amount of polynucleotides for testing, a blood volume of at least about 0.001, 0.005, 0.01, 0.05, 0.1, 0.5, 1, 2, 3, 4, 5, 10, 20, 25, 30, 35, 40, 45, or 50 mL is drawn. In some embodiments, blood can be collected into an apparatus containing a magnesium chelator including but not limited to EDTA, and is stored at 4° C. Optionally, a calcium chelator, including but not limited to EGTA, can be added.

In some embodiments, a cell lysis inhibitor is added to the blood including but not limited to formaldehyde, formaldehyde derivatives, formalin, glutaraldehyde, glutaraldehyde derivatives, a protein cross-linker, a nucleic acid cross-linker, a protein and nucleic acid cross-linker, primary amine reactive crosslinkers, sulfhydryl reactive crosslinkers, sulfhydryl addition or disulfide reduction, carbohydrate reactive crosslinkers, carboxyl reactive crosslinkers, photoreactive crosslinkers, or cleavable crosslinkers. In some embodiments, non-nucleic acid materials can be removed from the starting material using enzymatic treatments (such as protease digestion).

A plurality of samples may comprise at least 2, 3, 4, 5, 10, 20, 30, 40, 50, 60, 70, 80, 90 or 100 or more samples. The plurality of samples may comprise at least about 100, 200, 300, 400, 500, 600, 700, 800, 900 or 1000 or more samples. The plurality of samples may comprise at least about 1000, 2000, 3000, 4000, 5000, 6000, 7000, 8000 samples, 9000, or 10,000 samples, or 100,000 samples, or 1,000,000 or more samples. The plurality of samples may comprise at least about 10,000 samples.

The one or more polynucleotides in a first sample may be different from one or more polynucleotides in a second sample. The one or more polynucleotides in a first sample may be different from one or more polynucleotides in a plurality of samples. One or more polynucleotides in a sample can comprise at least about 80%, 85%, 90%, 95%, 96%, 97%, 98%, 99%, or 100% sequence identity. In some embodiments, one or more polynucleotides in a sample can differ by less than about 100, 90, 80, 70, 60, 50, 40, 30, 25, 20, 25, 10, 9, 8, 7, 6, 5, 4, 3, 2, or 1 nucleotide or base pair. A plurality of polynucleotides in one or more samples of the plurality of samples can comprise two or more identical sequences. At least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, 98%, 99% or 100% of the total polynucleotides in one or more of the plurality of samples can comprise the same sequence. A plurality of polynucleotides in one or more samples of the plurality of samples may comprise at least two different sequences. At least about 5%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% of the total polynucleotides in one or more of the plurality of samples may comprise at least two different sequences. In some embodiments, one or more polynucleotides are variants of each other. For example, one or more polynucleotides may contain single nucleotide polymorphisms or other types of mutations. In another example, one or more polynucleotides are splice variants.

A first sample may comprise one or more cells and the second sample may comprise one or more cells. The one or more cells of the first sample may be of the same cell type as the one or more cells of the second sample. The one or more cells of the first sample may be of a different cell type as one or more different cells of the plurality of samples.

The plurality of samples may be obtained concurrently. A plurality of samples can be obtained at the same time. The plurality of samples can be obtained sequentially. A plurality of samples can be obtained over a course of years, e.g., 100 years, 10 years, 5 years, 4 years, 3 years, 2 years or 1 year of obtaining one or more different samples. One or more samples can be obtained within about one year of obtaining one or more different samples. One or more samples can be obtained within 12 months, 11 months, 10 months, 9 months, 8 months, 7 months, 6 months, 4 months, 3 months, 2 months or 1 month of obtaining one or more different samples. One or more samples can be obtained within 30 days, 28 days, 26 days, 24 days, 21 days, 20 days, 18 days, 17 days, 16 days, 15 days, 14 days, 13 days, 12 days, 11 days, 10 days, 9 days, 8 days, 7 days, 6 days, 5 days, 4 days, 3 days, 2 days or 1 day of obtaining one or more different samples. One or more samples can be obtained within about 24 hours, 22 hours, 20 hours, 18 hours, 16 hours, 14 hours, 12 hours, 10 hours, 8 hours, 6 hours, 4 hours, 2 hours or 1 hour of obtaining one or more different samples. One or more samples can be obtained within about 60 seconds, 45 seconds, 30 seconds, 20 seconds, 10 seconds, 5 seconds, 2 seconds or 1 second of obtaining one or more different samples. One or more samples can be obtained within less than one second of obtaining one or more different samples.

The different polynucleotides of a sample can be present in the sample at different concentrations or amounts (e.g., different number of molecules). For example, the concentration or amount of one polynucleotide can be greater than the concentration or amount of another polynucleotide in the sample. In some embodiments, the concentration or amount of at least one polynucleotide in the sample is at least about 1.5, 2, 3, 4, 5, 6, 7, 8, 9, 10, 11, 12, 13, 14, 15, 20, 25, 30, 35, 40, 45, 50, 60, 70, 80, 90, 100, 200, 300, 400, 500, 600, 700, 800, 900, 1000, or more times greater than the concentration or amount of at least one other polynucleotide in the sample. In another example, the concentration or amount of one polynucleotide is less than the concentration or amount of another polynucleotide in the sample. The concentration or amount of at least one polynucleotide in the sample may be at least about 1.5, 2, 3, 4, 5, 6, 7, 8, 9, 10, 11, 12, 13, 14, 15, 20, 25, 30, 35, 40, 45, 50, 60, 70, 80, 90, 100, 200, 300, 400, 500, 600, 700, 800, 900, 1000, or more times less than the concentration or amount of at least one other polynucleotide in the sample.

In some embodiments, two or more samples may contain different amounts or concentrations of the polynucleotides. In some embodiments, the concentration or amount of one polynucleotide in one sample may be greater than the concentration or amount of the same polynucleotide in a different sample. For example, a blood sample might contain a higher amount of a particular polynucleotide than a urine sample. Alternatively, a single sample can divided into two or more subsamples. The subsamples may contain different amounts or concentrations of the same polynucleotide. The concentration or amount of at least one polynucleotide in one sample may be at least about 1.5, 2, 3, 4, 5, 6, 7, 8, 9, 10, 11, 12, 13, 14, 15, 20, 25, 30, 35, 40, 45, 50, 60, 70, 80, 90, 100, 200, 300, 400, 500, 600, 700, 800, 900, 1000, or more times greater than the concentration or amount of the same polynucleotide in another sample. Alternatively, the concentration or amount of one polynucleotide in one sample may be less than the concentration or amount of the same polynucleotide in a different sample. For example, the concentration or amount of at least one polynucleotide in one sample may be at least about 1.5, 2, 3, 4, 5, 6, 7, 8, 9, 10, 11, 12, 13, 14, 15, 20, 25, 30, 35, 40, 45, 50, 60, 70, 80, 90, 100, 200, 300, 400, 500, 600, 700, 800, 900, 1000, or more times less than the concentration or amount of the same polynucleotide in another sample.

Target Polynucleotides

In some cases, methods provided herein are directed to amplification and sequencing of a target polynucleotide molecule, such as a polynucleotide molecule from a cell. In some cases, methods provided herein are directed to amplification and sequencing of two or more regions of a target polynucleotide molecule. In some cases, methods provided herein are directed to amplification and sequencing of two or more target polynucleotide molecules. In one aspect, target polynucleotides are RNA. In one aspect, target polynucleotides are genomic nucleic acids. DNA derived from the genetic material in the chromosomes of a particular organism can be genomic DNA. In preferred embodiments, target polynucleotides include sequences comprising variable regions of an antibody or TCR produced by an immune cell. In some embodiments, target polynucleotides include sequences comprising a variable region of a heavy chain of an antibody produced by an immune cell. In some embodiments, target polynucleotides include sequences comprising a variable region of a light chain of an antibody produced by an immune cell. In some embodiments, target polynucleotides include sequences comprising a variable region of an alpha chain of a TCR produced by an immune cell. In some embodiments, target polynucleotides include sequences comprising a variable region of a beta chain of a TCR produced by an immune cell. In some embodiments, target polynucleotides include sequences comprising a variable region of a gamma chain of a TCR produced by an immune cell. In some embodiments, target polynucleotides include sequences comprising a variable region of a delta chain of a TCR produced by an immune cell.

Target polynucleotides can be obtained from virtually any source and can be prepared using methods known in the art. For example, target polynucleotides can be directly isolated without amplification using methods known in the art, including without limitation extracting a fragment of genomic DNA or mRNA from an organism or a cell (e.g., an immune cell) to obtain target polynucleotides. A target polynucleotide can also encompass cDNA generated from RNA (such as mRNA) through reverse transcription-PCR. In some cases, a target polynucleotide is an RNA molecule. In some cases, a target polynucleotide is an mRNA molecule, or a cDNA produced from the mRNA molecule. In some cases, a target polynucleotide is an mRNA molecule, or cDNA molecule produced from the mRNA molecule, from a single immune cell. In some cases, target polynucleotides are mRNA molecules, or cDNA molecules produced from the mRNA molecules, from individual immune cells. In some cases, target polynucleotides are mRNA molecules encoding an antibody sequence from a single immune cell. In some cases, target polynucleotides are mRNA molecules encoding heavy chain antibody sequences from individual immune cells. In some cases, target polynucleotides are mRNA molecules encoding a heavy chain antibody sequence from a single immune cell. In some cases, target polynucleotides are mRNA molecules encoding light chain antibody sequences from individual immune cells. In some cases, target polynucleotides are mRNA molecules encoding a light chain antibody sequence from a single immune cell. In some cases, target polynucleotides are mRNA molecules encoding antibody variable sequences from individual immune cells. In some cases, target polynucleotides are mRNA molecules encoding a variable antibody sequence from a single immune cell. In some cases, target polynucleotides are mRNA molecules encoding variable light chain antibody sequences from individual immune cells. In some cases, target polynucleotides are mRNA molecules encoding a variable light chain antibody sequence from a single immune cell. In some cases, target polynucleotides are mRNA molecules encoding variable heavy chain antibody sequences from individual immune cells. In some cases, target polynucleotides are mRNA molecules encoding a variable heavy chain antibody sequence from a single immune cell. In some cases, a target polynucleotide can be a cell-free nucleic acid, e.g., DNA or RNA. In some cases, target polynucleotides are mRNA molecules encoding variable alpha, beta, gamma, and/or delta chain TCR sequences from individual immune cells.

The methods described herein can be used to generate a library of polynucleotides from one or more target polynucleotides for sequencing. Target polynucleotides include any polynucleotides of interest that are not products of an amplification reaction. For example, a target polynucleotide can include a polynucleotide in a biological sample. For example, target polynucleotides do not include products of a PCR reaction. For example, target polynucleotides may include a polynucleotide template used to generate products of an amplification reaction, but do not include the amplification products themselves. For example, target polynucleotides may include a polynucleotide template used to generate products of a reverse transcription reaction or primer extension reaction, and also include the reverse transcription reaction or primer extension reaction products themselves. For example, target polynucleotides include polynucleotides of interest that can be subjected to a reverse transcription reaction or a primer extension reaction. For example, target polynucleotides include RNA or DNA. For example, target polynucleotides include cDNA. In some embodiments, target RNA polynucleotides are mRNA. In some embodiments, target RNA polynucleotides are polyadenylated. In some embodiments, the RNA polynucleotides are not polyadenylated. In some embodiments, the target polynucleotides are DNA polynucleotides. The DNA polynucleotides may be genomic DNA. The DNA polynucleotides may comprise exons, introns, untranslated regions, or any combination thereof.

In some embodiments, libraries can be generated from two or more regions of a target polynucleotide. In some embodiments, methods libraries can be generated from two or more target polynucleotides. In some embodiments, target polynucleotides are genomic nucleic acids or DNA derived from chromosomes. In some embodiments, target polynucleotides include sequences comprising a variant, such as a polymorphism or mutation. In some embodiments, target polynucleotides include DNA and not RNA. In some embodiments, target polynucleotides include RNA and not DNA. In some embodiments, target polynucleotides include DNA and RNA. In some embodiments, a target polynucleotide is an mRNA molecule. In some embodiments, a target polynucleotide is a DNA molecule. In some embodiments, a target polynucleotide is a single stranded polynucleotide. In some embodiments, a target polynucleotide is a double stranded polynucleotide. In some embodiments, a target polynucleotide is a single strand of a double stranded polynucleotide.

Target polynucleotides can be obtained from any biological sample and prepared using methods known in the art. In some embodiments, target polynucleotides are directly isolated without amplification. Methods for direct isolation are known in the art. Non-limiting examples include extracting genomic DNA or mRNA from a biological sample, organism or, cell.

In some embodiments, one or more target polynucleotides are purified from a biological sample. In some embodiments, a target polynucleotide is not purified from the biological sample in which it is contained. In some embodiments, a target polynucleotide is isolated from a biological sample. In some embodiments, a target polynucleotide is not isolated from the biological sample in which it is contained. In some embodiments, a target polynucleotide can be a cell-free nucleic acid. In some embodiments, a target polynucleotide can be a fragmented nucleic acid. In some embodiments, a target polynucleotide can be a transcribed nucleic acid. In some embodiments, a target polynucleotide is a modified polynucleotide. In some embodiments, a target polynucleotide is a non-modified polynucleotide.

In some embodiments, a target polynucleotide is polynucleotide from a single cell. In some embodiments, target polynucleotides are from individual cells. In some embodiments, a target polynucleotide is polynucleotide from a sample containing a plurality of cells.

In some embodiments, a target polynucleotide encodes a biomarker sequence. In some embodiments, a target polynucleotide encodes two or more biomarker sequences. In some embodiments, a plurality of target polynucleotides encodes a biomarker sequence. In some embodiments, a plurality of target polynucleotides encodes two or more biomarker sequences. In some embodiments, a plurality of target polynucleotides encodes 3, 4, 5, 6, 7, 8, 9, 10, 20, 30, 40, 50, 60, 70, 80, 90, or 100 or more biomarker sequences.

In some embodiments, a plurality of target polynucleotides comprises a panel of immunoglobulin sequences. In some embodiments, a plurality of target polynucleotides comprises a panel of TCR sequences. For example, a panel of immunoglobulin sequences can be $V_H$ and/or $V_L$ sequences. In some embodiments, a panel of immunoglobulin or TCR sequences contains 1, 2, 3, 4, 5, 6, 7, 8, 9, or 10 immunoglobulin or TCR sequences. In some embodiments, a panel of immunoglobulin or TCR sequences contains at least about 10, 20, 30, 40, 50, 60, 70, 80, 90, 100, 150, 200, 250, 300, 350, 400, 450, 500, 550, 600, 650, 700, 750, 800, 850, 900, 1000, 1500, 2000, 3000, 4000, 5000, 6000, 7000, 8000, 9000, 10,000, 11,000, 12,000, 13,000, 14,000, 15,000, 16,000, 17,000, 18,000, 19,000, 20,000, 25,000, 30,000, 35,000, 40,000, 45,000, 50,000, 60,000, 70,000, 80,000, 90,000, 100,000, 200,000, 300,000, 400,000, 500,000, 600,000, 700,000, 800,000, 900,000, $1 \times 10^6$, $2 \times 10^6$, $3 \times 10^6$, $4 \times 10^6$, $5 \times 10^6$, $6 \times 10^6$, $7 \times 10^6$, $8 \times 10^6$, $9 \times 10^6$, $1 \times 10^7$, $2 \times 10^7$, $3 \times 10^7$, $4 \times 10^7$, $5 \times 10^7$, $6 \times 10^7$, $7 \times 10^7$, $8 \times 10^7$, $9 \times 10^7$, $1 \times 10^8$, $2 \times 10^8$, $3 \times 10^8$, $4 \times 10^8$, $5 \times 10^8$, $6 \times 10^8$, $7 \times 10^8$, $8 \times 10^8$, $9 \times 10^8$, $1 \times 10^9$, $2 \times 10^9$, $3 \times 10^9$, $4 \times 10^9$, $5 \times 10^9$, $6 \times 10^9$, $7 \times 10^9$, $8 \times 10^9$, $9 \times 10^9$, $1 \times 10^{10}$, $2 \times 10^{10}$, $3 \times 10^{10}$, $4 \times 10^{10}$, $5 \times 10^{10}$, $6 \times 10^{10}$, $7 \times 10^{10}$, $8 \times 10^{10}$, $9 \times 10^{10}$, $1 \times 10^{11}$, $2 \times 10^{11}$, $3 \times 10^{11}$, $4 \times 10^{11}$, $5 \times 10^{11}$, $6 \times 10^{11}$, $7 \times 10^{11}$, $8 \times 10^{11}$, $9 \times 10^{11}$, $1 \times 10^{12}$, $2 \times 10^{12}$, $3 \times 10^{12}$, $4 \times 10^{12}$, $5 \times 10^{12}$, $6 \times 10^{12}$, $7 \times 10^{12}$, $8 \times 10^{12}$, or $9 \times 10^{12}$ immunoglobulin or TCR sequences. In some embodiments, a panel of immunoglobulin or TCR sequences contains at most about 10, 20, 30, 40, 50, 60, 70, 80, 90, 100, 150, 200, 250, 300, 350, 400, 450, 500, 550, 600, 650, 700, 750, 800, 850, 900, 1000, 1500, 2000, 3000, 4000, 5000, 6000, 7000, 8000, 9000, 10,000, 11,000, 12,000, 13,000, 14,000, 15,000, 16,000, 17,000, 18,000, 19,000, 20,000, 25,000, 30,000, 35,000, 40,000, 45,000, 50,000, 60,000, 70,000, 80,000, 90,000, 100,000, 200,000, 300,000, 400,000, 500,000, 600,000, 700,000, 800,000, 900,000, $1 \times 10^6$, $2 \times 10^6$, $3 \times 10^6$, $4 \times 10^6$, $5 \times 10^6$, $6 \times 10^6$, $7 \times 10^6$, $8 \times 10^6$, $9 \times 10^6$, $1 \times 10^7$, $2 \times 10^7$, $3 \times 10^7$, $4 \times 10^7$, $5 \times 10^7$, $6 \times 10^7$, $7 \times 10^7$, $8 \times 10^7$, $9 \times 10^7$, $1 \times 10^8$, $2 \times 10^8$, $3 \times 10^8$, $4 \times 10^8$, $5 \times 10^8$, $6 \times 10^8$, $7 \times 10^8$, $8 \times 10^8$, $9 \times 10^8$, $1 \times 10^9$, $2 \times 10^9$, $3 \times 10^9$, $4 \times 10^9$, $5 \times 10^9$, $6 \times 10^9$, $7 \times 10^9$, $8 \times 10^9$, $9 \times 10^9$, $1 \times 10^{10}$, $2 \times 10^{10}$, $3 \times 10^{10}$, $4 \times 10^{10}$, $5 \times 10^{10}$, $6 \times 10^{10}$, $7 \times 10^{10}$, $8 \times 10^{10}$, $9 \times 10^{10}$, $1 \times 10^{11}$, $2 \times 10^{11}$, $3 \times 10^{11}$, $4 \times 10^{11}$, $5 \times 10^{11}$, $6 \times 10^{11}$, $7 \times 10^{11}$, $8 \times 10^{11}$, $9 \times 10^{11}$, $1 \times 10^{12}$, $2 \times 10^{12}$, $3 \times 10^{12}$, $4 \times 10^{12}$, $5 \times 10^{12}$, $6 \times 10^{12}$, $7 \times 10^{12}$, $8 \times 10^{12}$, or $9 \times 10^{12}$ immunoglobulin or TCR sequences. In some embodiments, a panel of immunoglobulin or TCR sequences contains from about 10-20, 10-30, 10-40, 10-30, 10-40, 10-50, 10-60, 10-70, 10-80, 10-90, 10-100, 50-60, 50-70, 50-80, 50-90, 50-100, 100-200, 100-300, 100-400, 100-300, 100-400, 100-500, 100-600, 100-700, 100-800, 100-900, 100-1000, 500-600, 500-700, 500-800, 500-900, 500-1000, 1000-2000, 1000-3000, 1000-4000, 1000-3000, 1000-4000, 1000-5000, 1000-6000, 1000-7000, 1000-8000, 1000-9000, 1000-10000, 5000-6000, 5000-7000, 5000-8000, 5000-9000, 5000-10000, $1-1 \times 10^5$, $1-2 \times 10^5$, $1-3 \times 10^5$, $1-4 \times 10^5$, $1-5 \times 10^5$, $1-6 \times 10^5$, $1-7 \times 10^5$, $1-8 \times 10^5$, $9 \times 10^5$, $1-1 \times 10^6$, $1-2 \times 10^6$, $1-3 \times 10^6$, $1-4 \times 10^6$, $1-5 \times 10^6$, $1-6 \times 10^6$, $1-7 \times 10^6$, $1-8 \times 10^6$, $9 \times 10^9$, $1 \times 10^7$, $1-2 \times 10^7$, $1-3 \times 10^7$, $1-4 \times 10^7$, $1-5 \times 10^7$, $1-6 \times 10^7$, $1-7 \times 10^7$, $1-8 \times 10^7$, $1-9 \times 10^7$, $1-1 \times 10^8$, $1-2 \times 10^8$, $1-3 \times 10^8$, $1-4 \times 10^8$, $1-5 \times 10^8$, $1-6 \times 10^8$, $1-7 \times 10^8$, $1-8 \times 10^8$, $1-9 \times 10^8$, $1-1 \times 10^9$, $1-2 \times 10^9$, $1-3 \times 10^9$, $1-4 \times 10^9$, $1-5 \times 10^9$, $1-6 \times 10^9$, $1-7 \times 10^9$, $1-8 \times 10^9$, $1-9 \times 10^9$, $1-1 \times 10^{10}$, $1-2 \times 10^{10}$, $1-3 \times 10^{10}$, $1-4 \times 10^{10}$, $1-5 \times 10^{10}$, $1-6 \times 10^{10}$, $1-7 \times 10^{10}$, $1-8 \times 10^{10}$, $1-9 \times 10^{10}$, $1-1 \times 10^{11}$, $1-2 \times 10^{11}$, $1-3 \times 10^{11}$, $1-4 \times 10^{11}$, $1-5 \times 10^{11}$, $1-6 \times 10^{11}$, $1-7 \times 10^{11}$, $1-8 \times 10^{11}$, $1-9 \times 10^{11}$, $1-1 \times 10^{12}$, $1-2 \times 10^{12}$, $1-3 \times$ $10^{12}$, $1\text{-}4\times10^{12}$, $1\text{-}5\times10^{12}$, $1\text{-}6\times10^{12}$, $1\text{-}7\times10^{12}$, $1\text{-}8\times10^{12}$, or $1\text{-}9\times10^{12}$ immunoglobulin or TCR sequences.

In some embodiments, a target polynucleotide is about 10, 20, 30, 40, 50, 60, 70, 80, 90, 100, 150, 200, 250, 300, 350, 400, 450, 500, 550, 600, 650, 700, 750, 800, 850, 900, 1000, 1500, 2000, 3000, 4000, 5000, 6000, 7000, 8000, 9000, 10,000, 11,000, 12,000, 13,000, 14,000, 15,000, 16,000, 17,000, 18,000, 19,000, or 20,000 bases or base-pairs in length. In some embodiments, a target polynucleotide is at least about 10, 20, 30, 40, 50, 60, 70, 80, 90, 100, 150, 200, 250, 300, 350, 400, 450, 500, 550, 600, 650, 700, 750, 800, 850, 900, 1000, 1500, 2000, 3000, 4000, 5000, 6000, 7000, 8000, 9000, 10,000, 11,000, 12,000, 13,000, 14,000, 15,000, 16,000, 17,000, 18,000, 19,000, or 20,000 bases or base-pairs in length. In some embodiments, a target polynucleotide is at most about 10, 20, 30, 40, 50, 60, 70, 80, 90, 100, 150, 200, 250, 300, 350, 400, 450, 500, 550, 600, 650, 700, 750, 800, 850, 900, 1000, 1500, 2000, 3000, 4000, 5000, 6000, 7000, 8000, 9000, 10,000, 11,000, 12,000, 13,000, 14,000, 15,000, 16,000, 17,000, 18,000, 19,000, or 20,000 bases or base-pairs in length. In some embodiments, a target polynucleotide is from about 10-20, 10-30, 10-40, 10-30, 10-40, 10-50, 10-60, 10-70, 10-80, 10-90, 10-100, 50-60, 50-70, 50-80, 50-90, 50-100, 100-200, 100-300, 100-400, 100-300, 100-400, 100-500, 100-600, 100-700, 100-800, 100-900, 100-1000, 500-600, 500-700, 500-800, 500-900, 500-1000, 1000-2000, 1000-3000, 1000-4000, 1000-3000, 1000-4000, 1000-5000, 1000-6000, 1000-7000, 1000-8000, 1000-9000, 1000-10000, 5000-6000, 5000-7000, 5000-8000, 5000-9000, or 5000-10000 bases or base-pairs in length. In some embodiments, the average length of the target polynucleotides, or fragments thereof, can be less than about 100, 200, 300, 400, 500, or 800 base pairs, or less than about 5, 10, 20, 30, 40, 50, 60, 70, 80, 90, 100, 110, 120, 130, 140, 150, 160, 170, 180, 190, or 200 nucleotides, or less than about 1, 2, 5, 10, 20, 30, 40, 50, 60, 70, 80, 90, 100 kilobases. In some embodiments, a target sequence from a relative short template, such as a sample containing a target polynucleotide, is about 40, 45, 50, 55, 60, 65, 70, 75, 80, 85, 90, 95, or 100 bases. In certain embodiments, sequencing data are aligned against known or expected sequences using a database containing sequences or immunoglobulin or TCR sequences associated with a disease or condition.

Cloning and Expression of B-Cell Library Genetic Material

In some aspects, "antibody expression library" or "TCR expression library" or "expression library" as used herein can refer to a collection of molecules (i.e. two or more molecules) at either the nucleic acid or protein level. Thus, in some embodiments, this term can refer to a collection of expression vectors which encode a plurality of antibody or TCR molecules (i.e. at the nucleic acid level) and/or can refer to a collection of antibody or TCR molecules after they have been expressed in an appropriate expression system (i.e. at the protein level). Alternatively the expression vectors/expression library may be contained in suitable host cells in which they can be expressed. The antibody molecules which are encoded or expressed in the expression libraries of the invention can be in any appropriate format, e.g., may be whole antibody or TCR molecules or may be antibody or TCR fragments, e.g., single chain antibodies (e.g. scFv antibodies), Fv antibodies, Fab' antibodies, (Fab')$_2$ fragments, diabodies, etc. The terms "encoding" and "coding for" as is nucleic acid sequence "encoding"/"coding for" or a DNA coding sequence of or a nucleotide sequence "encoding"/"coding for" a particular enzyme, as well as other synonymous terms, refer to a DNA sequence which is transcribed and translated into an enzyme when placed under the control of appropriate regulatory sequences. A "promotor sequence" is a DNA regulatory region capable of binding RNA polymerase in a cell and initiating transcription of a downstream (3' direction) coding sequence. The promoter is part of the DNA sequence. This sequence region has a start codon at its 3' terminus. The promoter sequence includes the minimum number of bases with elements necessary to initiate transcription at levels detectable above background. However, after the RNA polymerase binds the sequence and transcription is initiated at the start codon (3' terminus with a promoter), transcription proceeds downstream in the 3' direction. Within the promotor sequence will be found a transcription initiation site (conveniently defined by mapping with nuclease S1) as well as protein binding domains (consensus sequences) responsible for the binding of RNA polymerase.

Antibody or TCR molecules identified by, derived from, selected from, or obtainable from the antibody or TCR expression libraries of the invention form a yet further aspect of the invention. Again these antibody or TCR molecules may be proteins or nucleic acids encoding antibody or TCR molecules, which nucleic acids may in turn be incorporated into an appropriate expression vector and/or be contained in a suitable host cell.

The cDNA pool can be subjected to a PCR reaction with polynucleotides that hybridize to a constant region of the heavy chain of antibody genes and polynucleotides that hybridize to the 5' end of the $V_H$ or Vα or Vγ chain region of antibody or TCR genes. The cDNA pool can be subjected to a PCR reaction with polynucleotides that hybridize to a constant region of the heavy chain or alpha or gamma chain of antibody or TCR genes and polynucleotides that hybridize to region 5' to the 5' end of the $V_H$ or Vα or Vγ chain region of a barcoded polynucleotide comprising an antibody or TCR sequence. A PCR reaction is can also set up for the amplification of the $V_L$ or Vβ or Vδ chain pool of e.g., kappa and lambda classes. The cDNA pool can be subjected to a PCR reaction with polynucleotides that hybridize to a constant region of the light chain of antibody genes and polynucleotides that hybridize to the 5' end of the $V_L$ or Vβ or Vδ chain region of antibody or TCR genes. The cDNA pool can be subjected to a PCR reaction with polynucleotides that hybridize to a constant region of the light chain of antibody genes and polynucleotides that hybridize to region 5' to the 5' end of the $V_L$ or Vβ or Vδ chain region of a barcoded polynucleotide comprising an antibody or TCR sequence. Such oligonucleotides or primers may be designed based on known and publicly available immunoglobulin or TCR gene sequence database information.

In some embodiments, $V_H$ and $V_L$ or Vα and Vβ or Vγ and Vδ sequences can be conveniently obtained from a library of $V_H$ and $V_L$ or Vα and Vβ or Vγ and Vδ sequences produced by PCR amplification using one or more primers that are not specific for heavy or light chain genes and, in particular, for one or both the terminal regions of the $V_H$ and $V_L$ or Vα and Vβ or Vγ and Vδ polynucleotides. In some embodiments, $V_H$ and $V_L$ sequences can be conveniently obtained from a library of $V_H$ and $V_L$ or Vα and Vβ or Vγ and Vδ sequences produced by PCR amplification using primers specific to a region of the vessel barcoded polynucleotide. In some embodiments, $V_H$ and $V_L$ sequences can be conveniently obtained from a library of $V_H$ and $V_L$ or Vα and Vβ or Vγ and Vδ sequences produced by PCR amplification using C-gene family-specific primers or C-gene-specific primers. In some embodiments, $V_H$ and $V_L$ sequences can be conveniently obtained from a library of $V_H$ and $V_L$ or Vα and Vβ or Vγ and Vδ sequences produced by PCR amplification using a primer set with a first primer specific to a region of the vessel barcoded polynucleotide and a second primer or plurality of second primers that are C-gene family-specific primers or C-gene-specific primers. In some embodiments, $V_H$ and $V_L$ or $V\alpha$ and $V\beta$ or $V\gamma$ and $V\delta$ sequences can be conveniently obtained from a library of $V_H$ and $V_L$ or $V\alpha$ and $V\beta$ or $V\gamma$ and $V\delta$ sequences produced by PCR amplification using a primer set with a first primer specific to a region of the vessel barcoded polynucleotide and a second primer specific to a universal sequence.

In some embodiments, upon reverse transcription, the resulting cDNA sequences may be amplified by PCR using one or more primers specific for immunoglobulin genes and, in particular, for one or both the terminal regions of the $V_H$ and $V_L$ or $V\alpha$ and $V\beta$ or $V\gamma$ and $V\delta$ polynucleotides. In some embodiments, $V_H$ and $V_L$ sequences can be obtained from a library of $V_H$ and $V_L$ or $V\alpha$ and $V\beta$ or $V\gamma$ and $V\delta$ sequences produced by PCR amplification using V-gene family-specific primers or V-gene-specific primers (Nicholls et al., J. Immunol. Meth., 1993, 165:81; WO93/12227) or are designed according to standard art-known methods based on available sequence information. (The $V_H$ and $V_L$ or $V\alpha$ and $V\beta$ or $V\gamma$ and $V\delta$ sequences can be ligated, usually with an intervening spacer sequence (e.g., encoding an in-frame flexible peptide spacer), forming a cassette encoding a single-chain antibody). V region sequences can be conveniently cloned as cDNAs or PCR amplification products for immunoglobulin-express sing cells. The $V_H$ and $V_L$ or $V\alpha$ and $V\beta$ or $V\gamma$ and $V\delta$ regions are sequenced, optionally, in the methods described herein and particularly after certain steps as noted (e.g., after single cell PCR; after mammalian or other cell surface display, after FACS screening, and the like). Sequencing can be used, among other reasons, to verify that the level of diversity is at an acceptable level. Sequencing can include high-throughput sequencing, deep sequencing (in which the same gene is sequenced from a plurality of individual samples to identify differences in the sequences), or combinations of the two.

In some embodiments, it is unnecessary to physically link the natural $V_H$ and $V_L$ or $V\alpha$ and $V\beta$ or $V\gamma$ and $V\delta$ combinations using the methods described herein. In some embodiments, cDNAs, barcoded polynucleotides, or PCR amplified barcoded cDNAs are not physically linked. In some embodiments, cDNAs, barcoded polynucleotides, or PCR amplified barcoded cDNAs are not physically linked in the same reaction or vessel.

In some embodiments, the natural $V_H$ and $V_L$ or $V\alpha$ and $V\beta$ or $V\gamma$ and $V\delta$ combinations are physically linked, using, in addition to the cDNA primers, one primer or plurality of primers for the 5' end of the $V_H$ or $V\alpha$ or $V\gamma$ gene and another primer or plurality of primers for the 5' end of the $V_L$ or $V\beta$ or $V\delta$ gene. These primers also contain complementary tails of extra sequence, to allow the self-assembly of the $V_H$ and $V_L$ or $V\alpha$ and $V\beta$ or $V\gamma$ and $V\delta$ genes. After PCR amplification and linking, the chance of getting mixed products, in other words, mixed variable regions, is minimal because the amplification and linking reactions were performed within each cell. The risk of mixing can be further decreased by utilizing bulky reagents such as digoxigenin labeled nucleotides to further ensure that V region cDNA pairs do not leave the cellular compartment and intermix, but remain within the cell for PCR amplification and linking. The amplified sequences are linked by hybridization of complementary terminal sequences. After linking, sequences may be recovered from cells for use in further method steps described herein. For example, the recovered DNA can be PCR amplified using terminal primers, if necessary, and cloned into vectors which may be plasmids, phages, cosmids, phagemids, viral vectors or combinations thereof as detailed below. Convenient restriction enzyme sites may be incorporated into the hybridized sequences to facilitate cloning. These vectors may also be saved as a library of linked variable regions for later use.

In some embodiments in which it is desired to provide additional $V_H$ and $V_L$ or $V\alpha$ and $V\beta$ or $V\gamma$ and $V\delta$ combinations, an expression system is chosen to facilitate this. For example, bacteriophage expression systems allow for the random recombination of heavy- and light-chain sequences. Other suitable expression systems are known to those skilled in the art.

It should be noted that in the case of $V_H$ and $V_L$ or $V\alpha$ and $V\beta$ or $V\gamma$ and $V\delta$ sequences derived from nonhumans, in some embodiments, it can be preferable to chimerize these sequences with a fully human Fc. As used herein "chimerized" refers to an immunoglobulin or TCR, wherein the heavy and light chain variable regions or $V\alpha$ and $V\beta$ or $V\gamma$ and $V\delta$ regions are not of human origin and wherein the constant regions of the heavy and light chains or $V\alpha$ and $V\beta$ or $V\gamma$ and $V\delta$ chains are of human origin. This is affected by amplifying and cloning the variable domains into a human Fc. The human Fc can be part of the vector, or in a separate molecule, and library of Fc's could also be used. In a preferred embodiment the chimerized molecules grown in mammalian cells such as CHO cells, screened with FACS twice to enrich the cell population for cells expressing the antibody of interest. The chimerized antibodies or TCRs are characterized, by either sequencing followed by functional characterization, or direct functional characterization or kinetics. Growth, screening and characterization are described in detail below.

It is important to note that the above described PCR reactions are described for cloning the antibodies in the IgG form. These are preferred as they are generally associated with a more mature immune response and generally exhibit higher affinity than IgM antibodies, thereby making them more desirable for certain therapeutic and diagnostic applications. Clearly, however, polynucleotides can be designed which will allow the cloning of one or more of the other forms of immunoglobulin molecules, e.g., IgM, IgA, IgE and IgD if desired or appropriate.

Once an antibody or TCR has been identified and the appropriate population of said cells have been isolated at an appropriate time and optionally enriched as described above, the antibody or TCR expression libraries need not be generated immediately, providing the genetic material contained in the cells can be kept intact thereby enabling the library to be made at a later date. Thus, for example the cells, a cell lysate, or nucleic acid, e.g., RNA or DNA derived therefrom, can be stored until a later date by appropriate methods, e.g., by freezing, and the expression libraries generated at a later date when desired.

Once the library of expression vectors has been generated, the encoded antibody molecules can then be expressed in an appropriate expression system and screened using appropriate techniques which are well known and documented in the art. Thus the above defined method of the invention may comprise the further steps of expressing the library of expression vectors in an appropriate expression system and screening the expressed library for antibodies with desired properties, as explained in further detail below.

As indicated herein, polynucleotides prepared by the methods of the disclosure which comprise a polynucleotide encoding antibody or TCR sequences can include, but are not limited to, those encoding the amino acid sequence of an antibody or TCR fragment, by itself, the noncoding sequence for the entire antibody or TCR or a portion thereof, the coding sequence for an antibody or TCR, fragment or portion, as well as additional sequences, such as the coding sequence of at least one signal leader or fusion peptide, with or without the aforementioned additional coding sequences, such as at least one intron, together with additional, non-coding sequences, including but not limited to, non-coding 5' and 3' sequences, such as the transcribed, nontranslated sequences that play a role in transcription, mRNA processing, including splicing and polyadenylation signals (for example—ribosome binding and stability of mRNA); an additional coding sequence that codes for additional amino acids, such as those that provide additional functionalities. Thus, the sequence encoding an antibody can be fused to a marker sequence, such as a sequence encoding a peptide that facilitates purification of the fused antibody or TCR comprising an antibody or TCR fragment or portion.

The primary PCR products can then optionally be subjected to a secondary PCR reaction with new polynucleotide sets that hybridize to the 5' and 3' ends of the antibody or TCR variable domains $V_H$, $V_L$ kappa and $V_L$ lambda or Vα and Vβ or Vγ and Vδ (as appropriate depending on whether the primary PCR reaction with which the new polynucleotide sets are used was designed to amplify portions of the heavy or light chain antibody genes or Vα or Vβ TCR genes or Vγ or Vδ TCR genes). These polynucleotides advantageously include DNA sequences specific for a defined set of restriction enzymes (i.e. restriction enzyme sites) for subsequent cloning. The selected restriction enzymes must be selected so as not to cut within human antibody or TCR V-gene segments. Such polynucleotides may be designed based on known and publicly available immunoglobulin or TCR gene sequence and restriction enzyme database information. However, preferred restriction enzyme sites to be included are NcoI, Hind III, MluI and NotI. The products of such secondary PCR reactions are repertoires of various V-heavy, V-light kappa and V-light lambda antibody fragments/domains. This type of secondary PCR reaction is therefore generally carried out when the expression library format of interest is a scFv or Fv format, wherein only the $V_H$ and $V_L$ or Vα and Vβ or Vγ and Vδ domains of an antibody or TCR are present. PCR products can also be subjected to a PCR reaction with new primer sets that hybridize to the 5' and 3' ends of the barcoded polynucleotides. These polynucleotides can advantageously include DNA sequences specific for a defined set of restriction enzymes (i.e. restriction enzyme sites) for subsequent cloning. The selected restriction enzymes must be selected so as not to cut within human antibody or TCR V-gene segments. Such polynucleotides may be designed based on known and publicly available immunoglobulin or TCR gene sequence and restriction enzyme database information. However, preferred restriction enzyme sites to be included are NcoI, Hind III, MluI and NotI. The products of such secondary PCR reactions are repertoires of various $V_H$, $V_L$ kappa and $V_L$ lambda antibody fragments/domains or Vα and Vβ or Vγ and Vδ TCR fragments/domains.

One of skill in the art will recognize that heavy or light chain or Vα or Vβ chain or Vγ or Vδ chain Fv or Fab fragments, or single-chain antibodies or TCRs may also be used with this system. A heavy or light chain or Vα or Vβ chain or Vγ or Vδ chain can be mutagenized followed by the addition of the complementary chain to the solution. The two chains are then allowed to combine and form a functional antibody fragment. Addition of random non-specific light or heavy chain or Vα or Vβ chain or Vγ or Vδ chain sequences allows for the production of a combinatorial system to generate a library of diverse members.

Libraries of such repertoires of cloned fragments comprising the variable heavy chain or Vα chain or Vγ chain regions, or fragments thereof, and/or variable light chain or Vβ chain or Vδ chain regions, or fragments thereof, of antibody or TCR genes derived from the B or T lymphocytes of immuno-challenged hosts as defined herein form further aspects of the invention. These libraries comprising cloned variable regions may optionally be inserted into expression vectors to form expression libraries.

In some embodiments, the PCR reactions can be set up so as to retain all or part of the constant regions of the various antibody or TCR chains contained in the isolated immune cell population. This is desirable when the expression library format is a Fab format, wherein the heavy or alpha or gamma chain component comprises $V_H$ or Vα or Vγ and $C_H$ or Cα or Cγ domains and the light chain or Vβ chain or Vδ chain component comprises $V_L$ or Vβ or Vδ chain and $C_L$ or Cβ or Cδ domains. Again, libraries of such cloned fragments comprising all or part of the constant regions of antibody or TCR chains form further aspects of the invention.

These nucleic acids can conveniently comprise sequences in addition to a polynucleotide of the present invention. For example, a multi-cloning site comprising one or more endonuclease restriction sites can be inserted into the nucleic acid to aid in isolation of the polynucleotide. Also, translatable sequences can be inserted to aid in the isolation of the translated polynucleotide of the present invention. For example, a hexa-histidine marker sequence provides a convenient means to purify the proteins of the present invention. The nucleic acid of the present invention, excluding the coding sequence, is optionally a vector, adapter, or linker for cloning and/or expression of a polynucleotide of the present invention.

Additional sequences can be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known in the art. (See, e.g., Ausubel, supra; or Sambrook, supra).

The libraries disclosed herein may be used in a variety of applications. As used herein, a library comprises a plurality of molecules. In some embodiments, a library comprises a plurality of polynucleotides. In some embodiments, a library comprises a plurality of primers. In some embodiments, a library comprises a plurality of sequence reads from one or more polynucleotides, amplicons, or amplicon sets. A library can be stored and used multiple times to generate samples for analysis. Some applications include, for example, genotyping polymorphisms, studying RNA processing, and selecting clonal representatives to do sequencing according to the methods provided herein. Libraries comprising a plurality of polynucleotides, such as primers or libraries for sequencing or amplification, can be generated, wherein a plurality of polynucleotides comprises at least about 2, 3, 4, 5, 6, 7, 8, 9, 10, 11, 12, 13, 14, 15, 20, 25, 30, 35, 40, 45, 50, 60, 70, 80, 90, 100, 200, 300, 400, 500, 600, 700, 800, 900, 1000, 1500, 2000, 3000, 4000, 5000, 6000, 7000, 8000, 9000, 10,000, 11,000, 12,000, 13,000, 14,000, 15,000, 16,000, 17,000, 18,000, 19,000, 20,000, 30,000, 40,000, 50,000, 60,000, 70,000, 80,000, 90,000, 100,000, 200,000, 300,000, 400,000, 500,000, 600,000, 700,000, 800,000, 900, 000, 1,000,000, 50,000,000, 100,000,000 or more molecular barcodes or vessel barcodes. In some embodiments, libraries of polynucleotides comprise a plurality of at least about 2, 3, 4, 5, 6, 7, 8, 9, 10, 11, 12, 13, 14, 15, 20, 25, 30, 35, 40, 45, 50, 60, 70, 80, 90, 100, 200, 300, 400, 500, 600, 700, 800, 900, 1000, 1500, 2000, 3000, 4000, 5000, 6000, 7000, 8000, 9000, 10,000, 11,000, 12,000, 13,000, 14,000, 15,000, 16,000, 17,000, 18,000, 19,000, 20,000, 30,000, 40,000, 50,000, 60,000, 70,000, 80,000, 90,000, 100,000, 200,000, 300,000, 400,000, 500,000, 600,000, 700,000, 800,000, 900,000, 1,000,000, 50,000,000, 100,000,000 or more unique polynucleotides, wherein each unique polynucleotide comprises one or more molecular barcodes and vessel barcodes.

Barcodes

A barcode can be a molecular barcode or a vessel barcode. In some embodiments, a barcode, such as a molecular barcode or a vessel barcode, can each have a length within a range of from 2 to 36 nucleotides, 4 to 36 nucleotides, or from 6 to 30 nucleotides, or from 8 to 20 nucleotides, 2 to 20 nucleotides, 4 to 20 nucleotides, or from 6 to 20 nucleotides. In certain aspects, the melting temperatures of barcodes within a set are within 10° C. of one another, within 5° C. of one another, or within 2° C. of one another. In certain aspects, the melting temperatures of barcodes within a set are not within 10° C. of one another, within 5° C. of one another, or within 2° C. of one another. In other aspects, barcodes are members of a minimally cross-hybridizing set. For example, the nucleotide sequence of each member of such a set can be sufficiently different from that of every other member of the set that no member can form a stable duplex with the complement of any other member under stringent hybridization conditions. In some embodiments, the nucleotide sequence of each member of a minimally cross-hybridizing set differs from those of every other member by at least two nucleotides. Barcode technologies are described in Winzeler et al. (1999) Science 285:901; Brenner (2000) Genome Biol. 1:1 Kumar et al. (2001) Nature Rev. 2:302; Giaever et al. (2004) Proc. Natl. Acad. Sci. USA 101:793; Eason et al. (2004) Proc. Natl. Acad. Sci. USA 101:11046; and Brenner (2004) Genome Biol. 5:240.

As used herein, a molecular barcode comprises information that is unique to a single molecule from a single cell or from a single vessel, or two or more molecules of a plurality or library of molecules from two or more single cells or from two or more single vessels. As used herein, a vessel barcode comprises information that is unique to polynucleotides from a single cell or from a single vessel, compared to polynucleotides from a different single cell or from a different single vessel. In some embodiments the unique information comprises a unique sequence of nucleotides. For example, the sequence of the molecular barcode or a vessel barcode can be determined by determining the identity and order of the unique or random sequence of nucleotides comprising the molecular barcode or a vessel barcode. In some embodiments the unique information cannot be used to identify the sequence of a target polynucleotide. For example, a molecular barcode may be attached to one target polynucleotide, but the molecular barcode cannot be used to determine the target polynucleotide to which it is attached. In some embodiments the unique information is not a known sequence linked to the identity of the sequence of a target polynucleotide. For example, a vessel barcode may be attached to one or more target polynucleotides, but the vessel barcode cannot be used to determine which of the one or more target polynucleotides to which it is attached. In some embodiments, the unique information comprises a random sequence of nucleotides. In some embodiments the unique information comprises one or more unique sequences of nucleotides on a polynucleotide. In some embodiments the unique information comprises a degenerate nucleotide sequence or degenerate barcode. A degenerate barcode can comprise a variable nucleotide base composition or sequence. For example, a degenerate bar code can be a random sequence. In some embodiments, a complement sequence of a molecular barcode or a vessel barcode is also a molecular barcode or a vessel barcode sequence.

A molecular barcode or vessel barcode can comprise any length of nucleotides. For example a molecular barcode or a vessel barcode can comprise at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 500, or 1000 nucleotides. For example a molecular barcode or a vessel barcode can comprise at most about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 500, or 1000 nucleotides. In some embodiments, a molecular barcode or a vessel barcode has a particular length of nucleotides. For example, a molecular barcode or a vessel barcode can be about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 500, or 1000 nucleotides in length.

In some embodiments, each molecular barcode or a vessel barcode in a plurality of molecular barcodes or vessel barcodes has at least about 2 nucleotides. For example, each molecular barcode or a vessel barcode in a plurality of molecular barcodes or vessel barcodes can be at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 500, or 1000 nucleotides in length. In some embodiments, each molecular barcode or a vessel barcode in a plurality of molecular barcodes or vessel barcodes has at most about 1000 nucleotides. For example, each molecular barcode or a vessel barcode in a plurality of molecular barcodes or vessel barcodes can be at most about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 500, or 1000 nucleotides in length. In some embodiments, each molecular barcode or a vessel barcode in a plurality of molecular barcodes or vessel barcodes has the same length of nucleotides. For example, each molecular barcode or a vessel barcode in a plurality of molecular barcodes or vessel barcodes can be 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 500, or 1000 nucleotides in length. In some embodiments, one or more molecular barcodes or vessel barcodes in a plurality of molecular barcodes or vessel barcodes have a different length of nucleotides. For example one or more first molecular barcodes or vessel barcodes in a plurality of molecular barcodes or vessel barcodes can have about, or at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 500, or 1000 nucleotides and one or more second molecular barcodes or vessel barcodes in a plurality of molecular barcodes or vessel barcodes can have about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 500, or 1000 nucleotides, wherein the number of nucleotides of the one or more first molecular barcodes or vessel barcodes is different than the one or more second molecular barcodes or vessel barcodes.

The number of molecular barcodes can be in excess of the total number of molecules to be labeled in a plurality of vessels. The number of vessel barcodes can be in excess of the total number of molecules to be labeled in a plurality of vessels. For example, the number of molecular barcodes or vessel barcodes can be at least about 2, 3, 4, 5, 6, 7, 8, 9, 10, 15, 20, 30, 40, 50, 60, 70, 80, 90, or 100 times greater than the total number of molecules to be labeled in a plurality of vessels.

The number of different molecular barcodes can be in excess of the total number of molecules to be labeled in a plurality of vessels. In some embodiments, the number of different molecular barcodes is at least about 1, 1.5, 2, 2.5, 3, 3.5, 4, 4.5, 5, 6, 7, 8, 9, 10, 15, 20, 30, 40, 50, 60, 70, 80, 90, or 100 times greater than the total number of molecules to be labeled in a plurality of vessels.

The number of different molecular barcodes in a single vessel can be in excess of the number of different molecules to be labeled in the single vessel. In some embodiments, the number of different molecular barcodes in a single vessel is at least about 1, 1.5, 2, 2.5, 3, 3.5, 4, 4.5, 5, 6, 7, 8, 9, 10, 15, 20, 30, 40, 50, 60, 70, 80, 90, or 100 times greater than the number of different molecules to be labeled in the single vessel.

The number of different vessel barcodes can be less than the total number of molecules to be labeled in a plurality of vessels. In some embodiments, the number of different vessel barcodes is at least about 1, 1.5, 2, 2.5, 3, 3.5, 4, 4.5, 5, 6, 7, 8, 9, 10, 15, 20, 30, 40, 50, 60, 70, 80, 90, or 100 times less than the total number of molecules to be labeled in a plurality of vessels.

The number of amplified product molecules from a vessel barcoded polynucleotide molecule in a single vessel can be in excess of the number of different molecules to be labeled in the single vessel. In some embodiments, the number of amplified product molecules from a vessel barcoded polynucleotide molecule in a single vessel is at least about 1, 1.5, 2, 2.5, 3, 3.5, 4, 4.5, 5, 6, 7, 8, 9, 10, 15, 20, 30, 40, 50, 60, 70, 80, 90, or 100 times greater than the number of different molecules to be labeled in the single vessel.

The number of vessel barcoded polynucleotide molecules in a single vessel can be less than the number of different molecules to be labeled in the single vessel. In some embodiments, the number of vessel barcoded polynucleotide molecules in a single vessel is at least about 1, 1.5, 2, 2.5, 3, 3.5, 4, 4.5, 5, 6, 7, 8, 9, 10, 15, 20, 30, 40, 50, 60, 70, 80, 90, or 100 times less than the number of different molecules to be labeled in the single vessel.

The number of vessel barcoded polynucleotide molecules in a single vessel can be one molecule. The number of unamplified vessel barcoded polynucleotide molecules in a single vessel can be one molecule.

In some embodiments, at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, or 100% of the different molecular barcodes have the same concentration. In some embodiments, at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, or 100% of the different vessel barcodes have the same concentration.

In some embodiments, at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, or 100% of the different molecular barcodes have a different concentration. In some embodiments, at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, or 100% of the different vessel barcodes have a different concentration.

The molecular barcodes or vessel barcodes in a population of molecular barcodes or vessel barcodes can have at least 10, 15, 20, 25, 30, 35, 40, 45, 50, 60, 70, 80, 90, 100, 200, 300, 400, 500, 600, 700, 800, 900, 1000 or more different sequences. For example, the molecular barcodes or vessel barcodes in a population can have at least 2,000, 3,000, 4,000, 5,000, 6,000, 7,000, 8,000, 9,000, 10,000, 15,000, 20,000, 25,000, 30,000, 35,000, 40,000, 45,000, 50,000, 60,000, 70,000, 80,000, 90,000, 100,000, 200,000, 300,000, 400,000, 500,000, 600,000, 700,000, 800,000, 900,000, 1,000,000 or more different sequences. Thus, a plurality of molecular barcodes or vessel barcodes can be used to generate at least 10, 15, 20, 25, 30, 35, 40, 45, 50, 60, 70, 80, 90, 100, 200, 300, 400, 500, 600, 700, 800, 900, 1000 or more different sequences from one or more polynucleotides, such as target polynucleotides. For example, a plurality of molecular barcodes or vessel barcodes can be used to generate at least 2,000, 3,000, 4,000, 5,000, 6,000, 7,000, 8,000, 9,000, 10,000, 15,000, 20,000, 25,000, 30,000, 35,000, 40,000, 45,000, 50,000, 60,000, 70,000, 80,000, 90,000, 100,000, 200,000, 300,000, 400,000, 500,000, 600,000, 700,000, 800,000, 900,000, $1 \times 10^6$, $2 \times 10^6$, $3 \times 10^6$, $4 \times 10^6$, $5 \times 10^6$, $6 \times 10^6$, $7 \times 10^6$, $8 \times 10^6$, $9 \times 10^6$, $1 \times 10^7$, $2 \times 10^7$, $3 \times 10^7$, $4 \times 10^7$, $5 \times 10^7$, $6 \times 10^7$, $7 \times 10^7$, $8 \times 10^7$, $9 \times 10^7$, $1 \times 10^8$, $2 \times 10^8$, $3 \times 10^8$, $4 \times 10^8$, $5 \times 10^8$, $6 \times 10^8$, $7 \times 10^8$, $8 \times 10^8$, $9 \times 10^8$, $1 \times 10^9$, $2 \times 10^9$, $3 \times 10^9$, $4 \times 10^9$, $5 \times 10^9$, $6 \times 10^9$, $7 \times 10^9$, $8 \times 10^9$, $9 \times 10^9$, $1 \times 10^{10}$, $2 \times 10^{10}$, $3 \times 10^{10}$, $4 \times 10^{10}$, $5 \times 10^{10}$, $6 \times 10^{10}$, $7 \times 10^{10}$, $8 \times 10^{10}$, $9 \times 10^{10}$, $1 \times 10^{11}$, $2 \times 10^{11}$, $3 \times 10^{11}$, $4 \times 10^{11}$, $5 \times 10^{11}$, $6 \times 10^{11}$, $7 \times 10^{11}$, $8 \times 10^{11}$, $9 \times 10^{11}$, $1 \times 10^{12}$, $2 \times 10^{12}$, $3 \times 10^{12}$, $4 \times 10^{12}$, $5 \times 10^{12}$, $6 \times 10^{12}$, $7 \times 10^{12}$, $8 \times 10^{12}$, $9 \times 10^{12}$ or more different sequences from one or more polynucleotides, such as target polynucleotides. For example, a plurality of molecular barcodes or vessel barcodes can be used to generate at least about 10, 15, 20, 25, 30, 35, 40, 45, 50, 60, 70, 80, 90, 100, 200, 300, 400, 500, 600, 700, 800, 900, 1000, 2000, 3000, 4000, 5000, 6000, 7000, 8000, 9000, 10,000, 15,000, 20,000, 25,000, 30,000, 35,000, 40,000, 45,000, 50,000, 60,000, 70,000, 80,000, 90,000, 100,000, 200,000, 300,000, 400,000, 500,000, 600,000, 700,000, 800,000, 900,000, $1 \times 10^6$, $2 \times 10^6$, $3 \times 10^6$, $4 \times 10^6$, $5 \times 10^6$, $6 \times 10^6$, $7 \times 10^6$, $8 \times 10^6$, $9 \times 10^6$, $1 \times 10^7$, $2 \times 10^7$, $3 \times 10^7$, $4 \times 10^7$, $5 \times 10^7$, $6 \times 10^7$, $7 \times 10^7$, $8 \times 10^7$, $9 \times 10^7$, $1 \times 10^8$, $2 \times 10^8$, $3 \times 10^8$, $4 \times 10^8$, $5 \times 10^8$, $6 \times 10^8$, $7 \times 10^8$, $8 \times 10^8$, $9 \times 10^8$, $1 \times 10^9$, $2 \times 10^9$, $3 \times 10^9$, $4 \times 10^9$, $5 \times 10^9$, $6 \times 10^9$, $7 \times 10^9$, $8 \times 10^9$, $9 \times 10^9$, $1 \times 10^{10}$, $2 \times 10^{10}$, $3 \times 10^{10}$, $4 \times 10^{10}$, $5 \times 10^{10}$, $6 \times 10^{10}$, $7 \times 10^{10}$, $8 \times 10^{10}$, $9 \times 10^{10}$, $1 \times 10^{11}$, $2 \times 10^{11}$, $3 \times 10^{11}$, $4 \times 10^{11}$, $5 \times 10^{11}$, $6 \times 10^{11}$, $7 \times 10^{11}$, $8 \times 10^{11}$, $9 \times 10^{11}$, $1 \times 10^{12}$, $2 \times 10^{12}$, $3 \times 10^{12}$, $4 \times 10^{12}$, $5 \times 10^{12}$, $6 \times 10^{12}$, $7 \times 10^{12}$, $8 \times 10^{12}$, $9 \times 10^{12}$ or more target polynucleotides.

In some embodiments, one or more molecular barcodes are used to group or bin sequences. In some embodiments, one or more molecular barcodes are used to group or bin sequences, wherein the sequences in each bin contain the same molecular barcode. In some embodiments, one or more molecular barcodes or vessel barcodes are used to group or bin sequences, wherein the sequences in each bin comprise an amplicon set. In some embodiments, one or more molecular barcodes are used to group or bin sequences, wherein the sequences in each bin comprise a plurality of sequences wherein the polynucleotides from which the plurality of sequences were generated were derived from the same polynucleotide molecule in an amplification reaction.

In some embodiments, one or more vessel barcodes are used to group or bin sequences. In some embodiments, one or more vessel barcodes are used to group or bin sequences, wherein the sequences in each bin contain the same vessel barcode. In some embodiments, one or more vessel barcodes are used to group or bin sequences, wherein the sequences in each bin comprise one or more amplicon sets. In some embodiments, one or more vessel barcodes are used to group or bin sequences, wherein the sequences in each bin comprise a plurality of sequences wherein the polynucleotides from which the plurality of sequences were generated were derived from the polynucleotides from a single vessel or single cell.

In some embodiments, one or more molecular barcodes and vessel barcodes are used to group or bin sequences. In some embodiments, one or more molecular barcodes and vessel barcodes are used to group or bin sequences, wherein the sequences in each bin contain the same molecular barcode and same vessel barcode. In some embodiments, one or more molecular barcodes and vessel barcodes are used to group or bin sequences, wherein the sequences in each bin comprise one or more amplicon sets. In some embodiments, one or more molecular barcodes and vessel barcodes are used to group or bin sequences, wherein the sequences in each bin comprise a plurality of sequences wherein the polynucleotides from which the plurality of sequences were generated were derived from the same polynucleotide in an amplification reaction and from the same single cell or vessel. In some embodiments, one or more molecular barcodes and vessel barcodes are not used to align sequences.

In some embodiments, one or more molecular barcodes are not used to align sequences. In some embodiments, one or more molecular barcodes are used to align sequences. In some embodiments, one or more molecular barcodes are used to group or bin sequences, and a target specific region is used to align sequences. In some embodiments, one or more vessel barcodes are not used to align sequences. In some embodiments, one or more vessel barcodes are used to align sequences. In some embodiments, one or more vessel barcodes are used to group or bin sequences, and a target specific region is used to align sequences. In some embodiments, one or more molecular barcodes and vessel barcodes are used to align sequences. In some embodiments, one or more molecular barcodes and vessel barcodes are used to group or bin sequences, and a target specific region is used to align sequences.

In some embodiments, the aligned sequences contain the same molecular barcode. In some embodiments, the aligned sequences contain the same vessel barcode. In some embodiments, the aligned sequences contain the same molecular barcode and vessel barcode. In some embodiments, one or more molecular barcodes or vessel barcodes are used align sequences, wherein the aligned sequences comprise two or more sequences from an amplicon set. In some embodiments, one or more molecular barcodes or vessel barcodes are used to align sequences, wherein the aligned sequences comprise a plurality of sequences wherein the polynucleotides from which the plurality of sequences were generated were derived from the same polynucleotide molecule in an amplification reaction. In some embodiments, one or more molecular barcodes or vessel barcodes are used to align sequences, wherein the aligned sequences comprise a plurality of sequences wherein the polynucleotides from which the plurality of sequences were generated were derived from a single cell or single vessel.

Droplet Generation

Splitting a sample of a plurality of cells into small reaction volumes, coupled with molecular and vessel barcoding of polynucleotides from, or derived from, an individual cell from the plurality of cells can enable high throughput sequencing of a repertoire of sequences, such as biomarker sequences.

Splitting a sample of a plurality of cells into small reaction volumes, coupled with molecular and vessel barcoding of polynucleotides from, or derived from, an individual cell from the plurality of cells can enable high throughput sequencing of a repertoire of sequences, such as sequences representing a percentage of the transcriptome of an organism. For example, a repertoire of sequences can comprise a plurality of sequences representing at least about 0.00001%, 0.00005%, 0.00010%, 0.00050%, 0.001%, 0.005%, 0.01%, 0.05%, 0.1%, 0.5%, 1%, 2%, 2.5%, 3%, 3.5%, 4%, 4.5%, 5%, 6%, 7%, 8%, 9%, 10%, 15%, 20%, 30%, 35%, 40%, 45, 50%, 55%, 60%, 65%, 70%, 75%, 80%, 85%, 90%, 95%, 98%, 99%, or 100% of the transcriptome of an organism.

Splitting a sample of immune cells into small reaction volumes, coupled with molecular and vessel barcoding of polynucleotides from, or derived from, an individual immune cell from the plurality of immune cells can enable high throughput sequencing of a repertoire of heavy and light chain sequences. These methods can also allow for pairing of the heavy and light chains after sequencing based on the barcoded sequences. Splitting a sample into small reaction volumes as described herein can also enable the use of reduced amounts of reagents, thereby lowering the material cost of the analysis.

In some cases, the reverse transcription reaction and/or the amplification reaction (e.g., PCR) are carried out in droplets, such as in droplet digital PCR. In certain aspects, the invention provides fluidic compartments to contain all or a portion of a target material. In some embodiments, a compartment is droplet. While reference is made to "droplets" throughout the specification, that term is used interchangeably with fluid compartment and fluid partition unless otherwise indicated. Except where indicated otherwise, "droplet" is used for convenience and any fluid partition or compartment may be used. The droplets used herein can include emulsion compositions (or mixtures of two or more immiscible fluids), such as described in U.S. Pat. No. 7,622,280. The droplets can be generated by devices described in WO/2010/036352. The term emulsion, as used herein, can refer to a mixture of immiscible liquids (such as oil and water). Oil-phase and/or water-in-oil emulsions allow for the compartmentalization of reaction mixtures within aqueous droplets. The emulsions can comprise aqueous droplets within a continuous oil phase. The emulsions provided herein can be oil-in-water emulsions, wherein the droplets are oil droplets within a continuous aqueous phase. The droplets provided herein are designed to prevent mixing between compartments, with each compartment protecting its contents from evaporation and coalescing with the contents of other compartments.

The mixtures or emulsions described herein can be stable or unstable. The emulsions can be relatively stable and have minimal coalescence. Coalescence occurs when small droplets combine to form progressively larger ones. In some cases, less than 0.00001%, 0.00005%, 0.00010%, 0.00050%, 0.001%, 0.005%, 0.01%, 0.05%, 0.1%, 0.5%, 1%, 2%, 2.5%, 3%, 3.5%, 4%, 4.5%, 5%, 6%, 7%, 8%, 9%, or 10% of droplets generated from a droplet generator coalesce with other droplets. The emulsions can also have limited flocculation, a process by which the dispersed phase comes out of suspension in flakes.

Droplets can be generated having an average diameter of about, less than about, or more than about, or at least about 0.001, 0.01, 0.05, 0.1, 1, 5, 10, 20, 30, 40, 50, 60, 70, 80, 100, 120, 130, 140, 150, 160, 180, 200, 300, 400, or 500 microns. Droplets can have an average diameter of about 0.001 to about 500, about 0.01 to about 500, about 0.1 to about 500, about 0.1 to about 100, about 0.01 to about 100, or about 1 to about 100 microns. Microfluidic methods of producing emulsion droplets using microchannel cross-flow focusing or physical agitation are known to produce either monodisperse or polydisperse emulsions. The droplets can be monodisperse droplets. The droplets can be generated such that the size of the droplets does not vary by more than plus or minus 5% of the average size of the droplets. In some cases, the droplets are generated such that the size of the droplets does not vary by more than plus or minus 2% of the average size of the droplets. A droplet generator can generate a population of droplets from a single sample, wherein none of the droplets vary in size by more than plus or minus about 0.1%, 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10% of the average size of the total population of droplets.

Higher mechanical stability can be useful for microfluidic manipulations and higher-shear fluidic processing (e.g., in microfluidic capillaries or through 90 degree turns, such as valves, in fluidic path). Pre- and post-thermally treated droplets or capsules can be mechanically stable to standard pipet manipulations and centrifugation.

A droplet can be formed by flowing an oil phase through an aqueous sample. The aqueous phase can comprise a buffered solution and reagents for performing an amplification reaction, including cells, nucleotides, nucleotide analogues, molecular barcoded polynucleotides, vessel barcoded polynucleotides primers, template nucleic acids, and enzymes, such as a DNA polymerase, RNA polymerase, and/or reverse transcriptase.

The aqueous phase can comprise a buffered solution and reagents for performing an amplification reaction with or without a solid surface, such as a bead. The buffered solution can comprise about, more than about, or less than about 1, 5, 10, 15, 20, 30, 50, 100, or 200 mM Tris. In some cases, the concentration of potassium chloride can be about, more than about, or less than about 10, 20, 30, 40, 50, 60, 80, 100, 200 mM. The buffered solution can comprise about 15 mM Tris and 50 mM KCl. The nucleotides can comprise deoxyribonucleotide triphosphate molecules, including dATP, dCTP, dGTP, and dTTP, in concentrations of about, more than about, or less than about 50, 100, 200, 300, 400, 500, 600, or 700 μm each. In some cases dUTP is added within the aqueous phase to a concentration of about, more than about, or less than about 50, 100, 200, 300, 400, 500, 600, or 700, 800, 900, or 1000 μm. In some cases, magnesium chloride or magnesium acetate ($MgCl_2$) is added to the aqueous phase at a concentration of about, more than about, or less than about 1.0, 2.0, 3.0, 4.0, or 5.0 mM. The concentration of $MgCl_2$ can be about 3.2 mM. In some cases, magnesium acetate or magnesium is used. In some cases, magnesium sulfate is used.

A non-specific blocking agent such as BSA or gelatin from bovine skin can be used, wherein the gelatin or BSA is present in a concentration range of approximately 0.1-0.9% w/v. Other possible blocking agents can include beta-lactoglobulin, casein, dry milk, or other common blocking agents. In some cases, preferred concentrations of BSA and gelatin are about 0.1% w/v.

Primers for amplification within the aqueous phase can have a concentration of about, more than about, or less than about 0.05, 0.1, 0.2, 0.3, 0.4, 0.5, 0.6, 0.7, 0.8, 0.9, 1.0, 1.2, 1.5, 1.7, or 2.0 μm. Primer concentration within the aqueous phase can be about 0.05 to about 2, about 0.1 to about 1.0, about 0.2 to about 1.0, about 0.3 to about 1.0, about 0.4 to about 1.0, or about 0.5 to about 1.0 μm. The concentration of primers can be about 0.5 μm. Amenable ranges for target nucleic acid concentrations in PCR include, but are not limited to between about 1 pg and about 500 ng.

In some cases, the aqueous phase can also comprise additives including, but not limited to, non-specific background/blocking nucleic acids (e.g., salmon sperm DNA), biopreservatives (e.g. sodium azide), PCR enhancers (e.g. Betaine, Trehalose, etc.), and inhibitors (e.g. RNAse inhibitors). Other additives can include, e.g., dimethyl sulfoxide (DMSO), glycerol, betaine (mono)hydrate (N,N,N-trimethylglycine=[caroxy-methyl] trimethylammonium), trehalose, 7-Deaza-2'-deoxyguanosine triphosphate (dC7GTP or 7-deaza-2'-dGTP), BSA (bovine serum albumin), formamide (methanamide), tetramethylammonium chloride (TMAC), other tetraalkylammonium derivatives (e.g., tetraethyammonium chloride (TEA-Cl) and tetrapropylammonium chloride (TPrA-Cl), non-ionic detergent (e.g., Triton X-100, Tween 20, Nonidet P-40 (NP-40)), or PREXCEL-Q. In some cases, the aqueous phase can comprise 0, 1, 2, 3, 4, 5, 6, 7, 8, 9, or 10 different additives. In other cases, the aqueous phase can comprise at least 0, 1, 2, 3, 4, 5, 6, 7, 8, 9, or 10 different additives.

In some cases, a non-ionic Ethylene Oxide/Propylene Oxide block copolymer can be added to the aqueous phase in a concentration of about 0.1%, 0.2%, 0.3%, 0.4%, 0.5%, 0.6%, 0.7%, 0.8%, 0.9%, or 1.0%. Common biosurfactants include non-ionic surfactants such as Pluronic F-68, Tetronics, and Zonyl FSN. Pluronic F-68 can be present at a concentration of about 0.5% w/v.

In some cases magnesium sulfate can be substituted for magnesium chloride, at similar concentrations. A wide range of common, commercial PCR buffers from varied vendors can be substituted for the buffered solution.

The emulsion can be formulated to produce highly monodisperse droplets having a liquid-like interfacial film that can be converted by heating into microcapsules having a solid-like interfacial film; such microcapsules can behave as bioreactors able to retain their contents through a reaction process such as PCR amplification. The conversion to microcapsule form can occur upon heating. For example, such conversion can occur at a temperature of greater than about 50° C., 60° C., 70° C., 80° C., 90° C., or 95° C. In some cases this heating occurs using a thermocycler. During the heating process, a fluid or mineral oil overlay can be used to prevent evaporation. Excess continuous phase oil can or cannot be removed prior to heating. The biocompatible capsules can be resistant to coalescence and/or flocculation across a wide range of thermal and mechanical processing. Following conversion, the capsules can be stored at about, more than about, or less than about 3° C., 4° C., 5° C., 6° C., 7° C., 8° C., 9° C. 10° C., 15° C., 20° C., 25° C., 30° C., 35° C., or 40° C. These capsules can be useful in biomedical applications, such as stable, digitized encapsulation of macromolecules, particularly aqueous biological fluids containing a mix of nucleic acids or protein, or both together; drug and vaccine delivery; biomolecular libraries; clinical imaging applications, and others.

The microcapsules can contain one or more polynucleotides and can resist coalescence, particularly at high temperatures. Accordingly, PCR amplification reactions can occur at a very high density (e.g., number of reactions per unit volume). In some cases, greater than 100,000, 500,000, 1,000,000, 1,500,000, 2,000,000, 2,500,000, 5,000,000, or 10,000,000 separate reactions can occur per ml. In some cases, the reactions occur in a single well, e.g., a well of a microtiter plate, without inter-mixing between reaction volumes. The microcapsules can also contain other components necessary to enable a reverse transcription, primer extension, and/or PCR reaction to occur, e.g., primers, probes, dNTPs, DNA or RNA polymerases, etc. These capsules exhibit resistance to coalescence and flocculation across a wide range of thermal and mechanical processing.

In some cases, the amplifying step is carried out by performing digital PCR, such as microfluidic-based digital PCR or droplet digital PCR.

Droplets can be generated using microfluidic systems or devices. As used herein, the "micro-" prefix (for example, as "microchannel" or "microfluidic"), generally refers to elements or articles having widths or diameters of less than about 1 mm, and less than about 100 microns (micrometers) in some cases. In some cases, the element or article includes a channel through which a fluid can flow. Additionally, "microfluidic", as used herein, refers to a device, apparatus or system that includes at least one microscale channel.

Microfluidic systems and devices have been described in a variety of contexts, typically in the context of miniaturized laboratory (e.g., clinical) analysis. Other uses have been described as well. For example, International Patent Application Publication Nos. WO 01/89788; WO 2006/040551; WO 2006/040554; WO 2004/002627; WO 2008/063227; WO 2004/091763; WO 2005/021151; WO 2006/096571; WO 2007/089541; WO 2007/081385 and WO 2008/063227.

A droplet generally includes an amount of a first sample fluid in a second carrier fluid. Any technique known in the art for forming droplets may be used with methods of the invention. An exemplary method involves flowing a stream of the sample fluid containing the target material (e.g., immune cell) such that it intersects two opposing streams of flowing carrier fluid. The carrier fluid is immiscible with the sample fluid. Intersection of the sample fluid with the two opposing streams of flowing carrier fluid results in partitioning of the sample fluid into individual sample droplets containing the target material.

The carrier fluid may be any fluid that is immiscible with the sample fluid. An exemplary carrier fluid is oil. In certain embodiments, the carrier fluid includes a surfactant.

The same method may be applied to create individual droplets that contain other reagents such as reagents for an amplification reaction such as a polymerase chain reaction (PCR), or a non-PCR based amplification reaction such as multi-strand displacement amplification, or other methods known to one of ordinary skill in the art. Suitable reagents for conducting PCR-based amplification reactions are known to those of ordinary skill in the art and include, but are not limited to, DNA polymerases, forward and reverse primers, deoxynucleotide triphosphates (dNTPs), and one or more buffers.

In certain embodiments, fluidic compartments are formed by providing a first fluid partition (e.g., a droplet) comprising a target material (e.g., an immune cell and/or a solid support such as a bead) and a second fluid (e.g., as a fluid stream or within droplets). The first and second fluids are merged to form a droplet. Merging can be accomplished by application of an electric field to the two fluids. In certain embodiments, the second fluid contains reagents for conducting an amplification reaction, such as a polymerase chain reaction or a amplification reaction.

In certain aspects, the invention provides a method of making a library of uniquely barcoded heavy and light chain antibody sequences and/or alpha and beta chain TCR sequences and/or gamma and delta chain TCR sequences including obtaining a plurality of nucleic acid constructs in which each construct includes a unique N-mer and a functional N-mer. The functional N-mer can be a random N-mer, a PCR primer, a universal primer, an antibody, a sticky end, or any other sequence. The method can include making M sets of a number N of fluid compartments each containing one or more copies of a unique construct. The method can create barcode libraries of higher complexity by adding an additional construct to each compartment in a set, and repeating that for each set to produce N×M compartments each containing a unique pair of constructs. The pairs can be hybridized or ligated to produce new constructs. In each construct in a barcode library, each unique N-mer can be adapted for identification by sequencing, probe hybridization, other methods, or a combination of methods.

Droplet Libraries

In general, a droplet library is made up of a number of library elements that are pooled together in a single collection. Libraries may vary in complexity from a single library element to $1 \times 10^{15}$ library elements or more. Each library element is one or more given components at a fixed concentration. The element may be, but is not limited to, cells, beads, amino acids, proteins, polypeptides, nucleic acids, polynucleotides or small molecule chemical compounds. The element may contain an identifier such as a molecular barcode, a vessel barcode, or both.

A cell library element can include, but is not limited to, hybridomas, B-cells, T-cells, primary cells, cultured cell lines, cancer cells, stem cells, or any other cell type. Cellular library elements are prepared by encapsulating a number of cells from one to tens of thousands in individual droplets. The number of cells encapsulated is usually given by Poisson statistics from the number density of cells and volume of the droplet. However, in some cases the number deviates from Poisson statistics as described in Edd et al., "Controlled encapsulation of single-cells into monodisperse picolitre drops." Lab Chip, 8(8):1262-1264, 2008. The discreet nature of cells allows for libraries to be prepared in mass with a plurality of cell variants, such as immune cells producing one antibody or TCR each, all present in a single starting media and then that media is broken up into individual droplet capsules that contain at most one cell. The cells within the individual droplets capsules are then lysed, heavy chain and light chain polynucleotides and/or alpha and beta chain polynucleotides and/or gamma and delta chain polynucleotides from the lysed cells are barcoded with molecular barcodes and vessel barcodes and amplified and then combined or pooled to form a library consisting of heavy and light chain and/or alpha and beta chain and/or gamma and delta chain library elements.

A bead based library element contains one or more beads, and may also contain other reagents, such as antibodies, enzymes or other proteins. In the case where all library elements contain different types of beads, but the same surrounding media, the library elements can all be prepared from a single starting fluid or have a variety of starting fluids. In the case of cellular libraries prepared in mass from a collection of variants, the library elements will be prepared from a variety of starting fluids. It is desirable to have exactly one cell per droplet with only a few droplets containing more than one cell when starting with a plurality of cells. In some cases, variations from Poisson statistics can be achieved to provide an enhanced loading of droplets such that there are more droplets with exactly one cell per droplet and few exceptions of empty droplets or droplets containing more than one cell.

In some embodiments, it is desirable to have exactly one vessel barcoded polynucleotide per droplet with only a few droplets containing more than one vessel barcoded polynucleotide when starting with a plurality of vessel barcoded polynucleotide. In some cases, variations from Poisson statistics can be achieved to provide an enhanced loading of droplets such that there are more droplets with exactly one vessel barcoded polynucleotide per droplet and few exceptions of empty droplets or droplets containing more than one vessel barcoded polynucleotide.

Examples of droplet libraries are collections of droplets that have different contents, ranging from beads, cells, small molecules, DNA, primers, antibodies, and barcoded polynucleotides. The droplets range in size from roughly 0.5 micron to 500 micron in diameter, which corresponds to about 1 picoliter to 1 nanoliter. However, droplets can be as small as 5 microns and as large as 500 microns. Preferably, the droplets are at less than 100 microns, about 1 micron to about 100 microns in diameter. The most preferred size is about 20 to 40 microns in diameter (10 to 100 picoliters). The preferred properties examined of droplet libraries include osmotic pressure balance, uniform size, and size ranges.

The droplets comprised within the droplet library provided by the instant invention are preferably uniform in size. That is, the diameter of any droplet within the library will vary less than 5%, 4%, 3%, 2%, 1% or 0.5% when compared to the diameter of other droplets within the same library. The uniform size of the droplets in the library may be critical to maintain the stability and integrity of the droplets and also may be essential for the subsequent use of the droplets within the library for the various biological and chemical assays described herein.

The invention provides a droplet library comprising a plurality of aqueous droplets within an immiscible fluid, wherein each droplet is preferably substantially uniform in size and comprises a different library element. The invention provides a method for forming the droplet library comprising providing a single aqueous fluid comprising different library elements, encapsulating each library element into an aqueous droplet within an immiscible fluid.

In certain embodiments, different types of elements (e.g., cells or beads), are pooled in a single source contained in the same medium. After the initial pooling, the elements are then encapsulated in droplets to generate a library of droplets wherein each droplet with a different type of bead or cell is a different library element. The dilution of the initial solution enables the encapsulation process. In some embodiments, the droplets formed will either contain a single element or will not contain anything, i.e., be empty. In other embodiments, the droplets formed will contain multiple copies of a library element. The elements being encapsulated are generally variants of a type. In one example, elements are immune cells of a blood sample, and each immune cell is encapsulated to amplify and barcode the antibody sequences of the nucleotides in the immune cells.

For example, in one type of emulsion library, there are library elements that have different particles, i.e., cells or barcoded polynucleotides in a different medium and are encapsulated prior to pooling. In one example, a specified number of library elements, i.e., n number of different cells or barcoded polynucleotides, is contained within different mediums. Each of the library elements are separately emulsified and pooled, at which point each of the n number of pooled different library elements are combined and pooled into a single pool. The resultant pool contains a plurality of water-in-oil emulsion droplets each containing a different type of particle.

In some embodiments, the droplets formed will either contain a single library element or will not contain anything, i.e., be empty. In other embodiments, the droplets formed will contain multiple copies of a library element. The contents of the beads follow a Poisson distribution, where there is a discrete probability distribution that expresses the probability of a number of events occurring in a fixed period of time if these events occur with a known average rate and independently of the time since the last event. The oils and surfactants used to create the libraries prevent the exchange of the contents of the library between droplets.

Primers

Generally, one or more pairs of primers can be used in a amplification reaction; one primer of a primer pair can be a forward primer and one primer of a primer pair can be a reverse primer.

In some cases, a first pair of primers can be used in the amplification reaction; one primer of the first pair can be a forward primer complementary to a sequence of a first target polynucleotide molecule and one primer of the first pair can be reverse primer can be complementary to a second sequence of the first target polynucleotide molecule, and a first target locus can reside between the first sequence and the second sequence. In some embodiments, the first target locus comprises a $V_H$ or Vα or Vγ sequence.

In some cases, a second pair of primers can be used in the amplification reaction; one primer of the second pair can be a forward primer complementary to a first sequence of a second target polynucleotide molecule and one primer of the second pair can be a reverse primer complementary to a second sequence of the second target polynucleotide molecule, and a second target locus can reside between the first sequence and the second sequence. In some embodiments, the second target locus comprises a $V_L$ or Vβ or Vδ sequence.

In some cases, a third pair of primers can be used in the amplification reaction; one primer of the third pair can be a forward primer complementary to a first sequence of a third target polynucleotide molecule and one primer of the third pair can be a reverse primer complementary to a second sequence of the third target polynucleotide molecule, and a third target locus can reside between the first sequence and the second sequence. In some embodiments, the third target locus comprises a barcode, such as a molecular barcode or vessel barcode.

The length of the forward primer and the reverse primer can depend on the sequence of the target polynucleotide and the target locus. For example, the length and/or $T_M$ of the forward primer and reverse primer can be optimized. In some case, a primer can be about, more than about, or less than about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 nucleotides in length. In some cases, a primer is about 15 to about 20, about 15 to about 25, about 15 to about 30, about 15 to about 40, about 15 to about 45, about 15 to about 50, about 15 to about 55, about 15 to about 60, about 20 to about 25, about 20 to about 30, about 20 to about 35, about 20 to about 40, about 20 to about 45, about 20 to about 50, about 20 to about 55, or about 20 to about 60 nucleotides in length.

A primer can be a single-stranded DNA prior to binding a template polynucleotide. In some cases, the primer initially comprises double-stranded sequence. The appropriate length of a primer can depend on the intended use of the primer but can range from about 6 to about 50 nucleotides, or from about 15 to about 35 nucleotides. Short primer molecules can generally require cooler temperatures to form sufficiently stable hybrid complexes with a template. In some embodiments, a primer need not reflect the exact sequence of the template nucleic acid, but can be sufficiently complementary to hybridize with a template. In some cases, a primer can be partially double-stranded before binding to a template polynucleotide. A primer with double-stranded sequence can have a hairpin loop of about, more than about, or less than about 3, 4, 5, 6, 7, 8, 9, 10, 11, 12, 13, 14, 15, 16, 17, 18, 19, or 20 bases. A double stranded portion of a primer can be about, more than about, less than about, or at least about 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 base-pairs. The design of suitable primers for the amplification of a given target sequence is well known in the art.

Primers can incorporate additional features that allow for the detection or immobilization of the primer but do not alter a basic property of the primer (e.g., acting as a point of initiation of DNA synthesis). For example, primers can contain an additional nucleic acid sequence at the 5' end which does not hybridize to a target nucleic acid, but which facilitates cloning or further amplification, or sequencing of an amplified product. For example, the additional sequence can comprise a primer binding site, such as a universal primer binding site. A region of the primer which is sufficiently complementary to a template to hybridize can be referred to herein as a hybridizing region.

In another case, a primer utilized in methods and compositions described herein can comprise one or more universal nucleosides. Non-limiting examples of universal nucleosides are 5-nitroindole and inosine, as described in U.S. Appl. Pub. Nos. 2009/0325169 and 2010/0167353.

Primers can be designed according to known parameters for avoiding secondary structures and self-hybridization. Different primer pairs can anneal and melt at about the same temperatures, for example, within 1° C., 2° C., 3° C., 4° C., 5° C., 6° C., 7° C., 8° C., 9° C. or 10° C. of another primer pair. In some cases, greater than 1, 2, 3, 4, 5, 6, 7, 8, 9, 10, 15, 20, 25, 30, 35, 40, 45, 50, 100, 200, 500, 1000, 5000, 10,000 or more primers are initially used. Such primers can hybridize to target polynucleotides described herein.

Primers can be prepared by a variety of methods including but not limited to cloning of appropriate sequences and direct chemical synthesis using methods well known in the art (Narang et al., Methods Enzymol. 68:90 (1979); Brown et al., Methods Enzymol. 68:109 (1979)). Primers can also be obtained from commercial sources. The primers can have an identical melting temperature. The primers can have non-identical melting temperatures. The lengths of the primers can be extended or shortened at the 5' end or the 3' end to produce primers with desired melting temperatures. One of the primers of a primer pair can be longer than the other primer. The 3' annealing lengths of the primers, within a primer pair, can differ. Also, the annealing position of each primer pair can be designed such that the sequence and length of the primer pairs yield the desired melting temperature. An equation for determining the melting temperature of primers smaller than 25 base pairs is the Wallace Rule ($T_M=2(A+T)+4(G+C)$). Computer programs can also be used to design primers. The $T_M$ (melting or annealing temperature) of each primer can be calculated using software programs. The annealing temperature of the primers can be recalculated and increased after any cycle of amplification, including but not limited to cycle 1, 2, 3, 4, 5, cycles 6-10, cycles 10-15, cycles 15-20, cycles 20-25, cycles 25-30, cycles 30-35, or cycles 35-40. After the initial cycles of amplification, the 5' half of the primers can be incorporated into the products from each loci of interest; thus the $T_M$ can be recalculated based on both the sequences of the 5' half and the 3' half of each primer.

Conducting the one or more reactions of the methods disclosed herein can comprise the use of one or more primers. As used herein, a primer comprises a double-stranded, single-stranded, or partially single-stranded polynucleotide that is sufficiently complementary to hybridize to a template polynucleotide. A primer can be a single-stranded DNA prior to binding a template polynucleotide. In some embodiments, the primer initially comprises double-stranded sequence. A primer site includes the area of the template to which a primer hybridizes. In some embodiments, primers are capable of acting as a point of initiation for template-directed nucleic acid synthesis. For example, primers can initiate template-directed nucleic acid synthesis when four different nucleotides and a polymerization agent or enzyme, such as DNA or RNA polymerase or reverse transcriptase. A primer pair includes 2 primers: a first primer with a 5' upstream region that hybridizes with a 5' end of a template sequence, and a second primer with a 3' downstream region that hybridizes with the complement of the 3' end of the template sequence. A primer set includes two or more primers: a first primer or first plurality of primers with a 5' upstream region that hybridizes with a 5' end of a template sequence or plurality of template sequences, and a second primer or second plurality of primers with a 3' downstream region that hybridizes with the complement of the 3' end of the template sequence or plurality of template sequences. In some embodiments, a primer comprises a target specific sequence. In some embodiments, a primer comprises a sample barcode sequence. In some embodiments, a primer comprises a universal priming sequence. In some embodiments, a primer comprises a PCR priming sequence. In some embodiments, a primer comprises a PCR priming sequence used to initiate amplification of a polynucleotide. (Dieffenbach, PCR Primer: A Laboratory Manual, 2nd Edition (Cold Spring Harbor Press, New York (2003)). The universal primer binding site or sequence allows the attachment of a universal primer to a polynucleotide and/or amplicon. Universal primers are well known in the art and include, but are not limited to, −47F (M13F), alfaMF, AOX3', AOX5', BGHr, CMV-30, CMV-50, CVMf, LACrmt, lamgda gt10F, lambda gt 10R, lambda gt11F, lambda gt11R, M13 rev, M13Forward(−20), M13Reverse, male, p10SEQPpQE, pA-120, pet4, pGAP Forward, pGLRVpr3, pGLpr2R, pKLAC14, pQEFS, pQERS, pucU1, pucU2, reversA, seqIREStam, seqIRESzpet, seqori, seqPCR, seqpIRES−, seqpIRES+, seqpSecTag, seqpSecTag+, seqretro+PSI, SP6, T3-prom, T7-prom, and T7-termInv. As used herein, attach can refer to both or either covalent interactions and noncovalent interactions. Attachment of the universal primer to the universal primer binding site may be used for amplification, detection, and/or sequencing of the polynucleotide and/or amplicon. The universal primer binding site may comprise at least about 1, 2, 3, 4, 5, 6, 7, 8, 9, 10, 11, 12, 13, 14, 15, 16, 17, 18, 19, 20, 30, 40, 50, 60, 70, 80, 90, 100, 200, 300, 400, 500, 600, 700, 800, 900, or 1000 nucleotides or base pairs. In another example, the universal primer binding site comprises at least about 1500, 2000, 2500, 3000, 3500, 4000, 4500, 5000, 5500, 6000, 6500, 7000, 7500, 8000, 8500, 9000, 9500, or 10000 nucleotides or base pairs. In some embodiments, the universal primer binding site comprises 1-10, 10-20, 10-30 or 10-100 nucleotides or base pairs. In some embodiments, the universal primer binding site comprises from about 1-90, 1-80, 1-70, 1-60, 1-50, 1-40, 1-30, 1-20, 1-10, 2-90, 2-80, 2-70, 2-60, 2-50, 2-40, 2-30, 2-20, 2-10, 1-900, 1-800, 1-700, 1-600, 1-500, 1-400, 1-300, 1-200, 1-100, 2-900, 2-800, 2-700, 2-600, 2-500, 2-400, 2-300, 2-200, 2-100, 5-90, 5-80, 5-70, 5-60, 5-50, 5-40, 5-30, 5-20, 5-10, 10-90, 10-80, 10-70, 10-60, 10-50, 10-40, 10-30, 10-20, 10-10, 5-900, 5-800, 5-700, 5-600, 5-500, 5-400, 5-300, 5-200, 5-100, 10-900, 10-800, 10-700, 10-600, 10-500, 10-400, 10-300, 10-200, 10-100, 25-900, 25-800, 25-700, 25-600, 25-500, 25-400, 25-300, 25-200, 25-100, 100-1000, 100-900, 100-800, 100-700, 100-600, 100-500, 100-400, 100-300, 100-200, 200-1000, 200-900, 200-800, 200-700, 200-600, 200-500, 200-400, 200-300, 300-1000, 300-900, 300-800, 300-700, 300-600, 300-500, 300-400, 400-1000, 400-900, 400-800, 400-700, 400-600, 400-500, 500-1000, 500-900, 500-800, 500-700, 500-600, 600-1000, 600-900, 600-800, 600-700, 700-1000, 700-900, 700-800, 800-1000, 800-900, or 900-1000 nucleotides or base pairs.

Primers can have a length compatible with its use in synthesis of primer extension products. A primer can be a polynucleotide that is 8 to 200 nucleotides in length. The length of a primer can depend on the sequence of the template polynucleotide and the template locus. For example, the length and/or melting temperature ($T_M$) of a primer or primer set can be optimized. In some case, a primer can be about, more than about, or less than about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 nucleotides in length. In some embodiments, primers are about 8-100 nucleotides in length, for example, 10-75, 15-60, 15-40, 18-30, 20-40, 21-50, 22-45, 25-40, 7-9, 12-15, 15-20, 15-25, 15-30, 15-45, 15-50, 15-55, 15-60, 20-25, 20-30, 20-35, 20-45, 20-50, 20-55, or 20-60 nucleotides in length and any length there between. In some embodiments, primers are at most about 10, 12, 15, 20, 21, 22, 23, 24, 25, 26, 27, 28, 29, 30, 35, 40, 45, 50, 55, 60, 65, 70, 75, 80, 85, 90, 95 or 100 nucleotides in length.

Generally, one or more pairs of primers can be used in an exponential amplification reaction; one primer of a primer pair can be a forward primer and one primer of a primer pair can be a reverse primer. In some embodiments, a first pair of primers can be used in the exponential amplification reaction; one primer of the first pair can be a forward primer complementary to a sequence of a first template polynucleotide molecule and one primer of the first pair can be a reverse primer complementary to a second sequence of the first template polynucleotide molecule, and a first template locus can reside between the first sequence and the second sequence. In some embodiments, a second pair of primers can be used in the amplification reaction; one primer of the second pair can be a forward primer complementary to a first sequence of a second target polynucleotide molecule and one primer of the second pair can be a reverse primer complementary to a second sequence of the second target polynucleotide molecule, and a second target locus can reside between the first sequence and the second sequence. In some embodiments, the second target locus comprises a variable light chain antibody sequence. In some embodiments, a third pair of primers can be used in the amplification reaction; one primer of the third pair can be a forward primer complementary to a first sequence of a third template polynucleotide molecule and one primer of the third pair can be a reverse primer complementary to a second sequence of the third template polynucleotide molecule, and a third template locus can reside between the first sequence and the second sequence.

The one or more primers can anneal to at least a portion of a plurality of template polynucleotides. The one or more primers can anneal to the 3' end and/or 5' end of the plurality of template polynucleotides. The one or more primers can anneal to an internal region of the plurality of template polynucleotides. The internal region can be at least about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 150, 200, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 650, 700, 750, 800, 850, 900 or 1000 nucleotides from the 3' ends or 5' ends the plurality of template polynucleotides. The one or more primers can comprise a fixed panel of primers. The one or more primers can comprise at least one or more custom primers. The one or more primers can comprise at least one or more control primers. The one or more primers can comprise at least one or more housekeeping gene primers. The one or more primers can comprise a universal primer. The universal primer can anneal to a universal primer binding site. In some embodiments, the one or more custom primers anneal to an SBC, a target specific region, complements thereof, or any combination thereof. The one or more primers can comprise a universal primer. The one or more primers primer can be designed to amplify or perform primer extension, reverse transcription, linear extension, non-exponential amplification, exponential amplification, PCR, or any other amplification method of one or more target or template polynucleotides The target specific region can comprise at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 150, 200, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 650, 700, 750, 800, 850, 900 or 1000 nucleotides or base pairs. In another example, the target specific region comprises at least about 1500, 2000, 2500, 3000, 3500, 4000, 4500, 5000, 5500, 6000, 6500, 7000, 7500, 8000, 8500, 9000, 9500, or 10000 nucleotides or base pairs. in some embodiments, the target specific region comprises from about 5-10, 10-15, 10-20, 10-30, 15-30, 10-75, 15-60, 15-40, 18-30, 20-40, 21-50, 22-45, 25-40, 7-9, 12-15, 15-20, 15-25, 15-30, 15-45, 15-50, 15-55, 15-60, 20-25, 20-30, 20-35, 20-45, 20-50, 20-55, 20-60, 2-900, 2-800, 2-700, 2-600, 2-500, 2-400, 2-300, 2-200, 2-100, 25-900, 25-800, 25-700, 25-600, 25-500, 25-400, 25-300, 25-200, 25-100, 100-1000, 100-900, 100-800, 100-700, 100-600, 100-500, 100-400, 100-300, 100-200, 200-1000, 200-900, 200-800, 200-700, 200-600, 200-500, 200-400, 200-300, 300-1000, 300-900, 300-800, 300-700, 300-600, 300-500, 300-400, 400-1000, 400-900, 400-800, 400-700, 400-600, 400-500, 500-1000, 500-900, 500-800, 500-700, 500-600, 600-1000, 600-900, 600-800, 600-700, 700-1000, 700-900, 700-800, 800-1000, 800-900, or 900-1000 nucleotides or base pairs.

Primers can be designed according to known parameters for avoiding secondary structures and self-hybridization. In some embodiments, different primer pairs can anneal and melt at about the same temperatures, for example, within 1° C., 2° C., 3° C., 4° C., 5° C., 6° C., 7° C., 8° C., 9° C. or 10° C. of another primer pair. In some embodiments, one or more primers in a plurality of primers can anneal and melt at about the same temperatures, for example, within 1, 2, 3, 4, 5, 6, 7, 8, 9 or 10° C. of another primer in the plurality of primers. In some embodiments, one or more primers in a plurality can anneal and melt at different temperatures than another primer in the plurality of primers.

A plurality of primers for one or more steps of the methods described herein can comprise a plurality of primers comprising about, at most about, or at least about 1, 2, 3, 4, 5, 6, 7, 8, 9, 10, 11, 12, 13, 14, 15, 16, 17, 18, 19, 20, 30, 40, 50, 60, 70, 80, 90, 100, 200, 300, 400, 500, 600, 700, 800, 900, 1000, 1500, 2000, 3000, 4000, 5000, 6000, 7000, 8000, 9000, 10,000, 11,000, 12,000, 13,000, 14,000, 15,000, 16,000, 17,000, 18,000, 19,000, 20,000, 30,000, 40,000, 50,000, 60,000, 70,000, 80,000, 90,000, 100,000, 200,000, 300,000, 400,000, 500,000, 600,000, 700,000, 800,000, 900,000, 1,000,000, 50,000,000, 100,000,000 different primers. For example, each primer in a plurality of primers can comprise a different target or template specific region or sequence.

Reverse Transcription

In some cases, the target polynucleotides are prepared from an RNA by reverse transcription. In some cases, the target polynucleotides are prepared from a DNA by primer extension, such as using a polymerase.

The methods described herein can be used in coupled reverse transcription-PCR (reverse transcription-PCR). For example, reverse transcription and PCR can be carried out in two distinct steps. First a cDNA copy of the sample mRNA can be synthesized using either a polynucleotide dT primer, a sequence specific primer, a universal primer, or any primer described herein.

Reverse transcription and PCR can be carried out in a single closed vessel reaction. For example, three primers can be employed, one for reverse transcription and two for PCR. The primer for reverse transcription can bind to the mRNA 3' to the position of the PCR amplicon. Although not essential, the reverse transcription primer can include RNA residues or modified analogs such as 2'-O-methyl RNA bases, which will not form a substrate for RNase H when hybridized to the mRNA.

The temperature to carry out the reverse transcription reaction depends on the reverse transcriptase being used. In some cases, a thermostable reverse transcriptase is used and the reverse transcription reaction is carried out at about 37° C. to about 75° C., at about 37° C. to about 50° C., at about 37° C. to about 55° C., at about 37° C. to about 60° C., at about 55° C. to about 75° C., at about 55° C. to about 60° C., at about 37° C., or at about 60° C. In some cases, a reverse transcriptase that transfers 3 or more non-template terminal nucleotides to an end of the transcribed product is used.

A reverse transcription reaction and the PCR reaction described herein can be carried out in various formats known in the art, such as in tubes, microtiter plates, microfluidic devices, or, preferably, droplets.

A reverse transcription reaction can be carried out in volumes ranging from 5 µL to 100 µL, or in 10 µL to 20 µL reaction volumes. In droplets, reaction volumes can range from 1 pL to 100 nL, or 10 pL to 1 nL. In some cases, the reverse transcription reaction is carried out in a droplet having a volume that is about or less than 1 nL. In some cases, a PCR reaction is in a droplet having a reaction volume ranges from 1 pL to 100 nL preferably 10 pL to 1 nL. In some cases, the PCR reaction is carried out in a droplet having a volume that is about or less than 1 nL. In some cases, a reverse transcription reaction and a PCR reaction are carried out in the same droplet having a reaction volume ranges from 1 pL to 100 nL or 10 pL to 1 nL. In some cases, the reverse transcription reaction and the PCR reaction are carried out in a droplet having a volume that is about or less than 1 nL or a volume that is about or less than 1 pL. In some cases, a reverse transcription reaction and a PCR reaction are carried out in a different droplet. In some cases, a reverse transcription reaction and a PCR reaction are carried out in a plurality of droplets each having a reaction volume ranges from 1 pL to 100 nL or 10 pL to 1 nL. In some cases, the reverse transcription reaction and the PCR reaction are carried out in a plurality of droplets each having a volume that is about or less than 1 nL.

In some cases, a first PCR reaction is in a first droplet having a reaction volume ranges from 1 pL to 100 nL preferably 10 pL to 1 nL and a second PCR reaction is in a second droplet having a reaction volume ranges from 1 pL to 100 nL preferably 10 pL to 1 nL. In some cases, a first PCR reaction is in a first droplet having a volume that is about or less than 1 nL, and a second PCR reaction is in a second droplet having a volume that is about or less than 1 nL.

In some cases, a first PCR reaction and a second PCR reaction are carried out in a plurality of droplets each having a reaction volume ranges from 1 pL to 100 nL or 10 pL to 1 nL. In some cases, a first PCR reaction and a second PCR reaction are carried out in a plurality of droplets each having a volume that is about or less than 1 nL.

Target polynucleotides, such as RNA, can be reverse transcribed into cDNA using one or more reverse transcription primers. The one or more reverse transcription primers can comprise a region complementary to a region of the RNA, such as a constant region (e.g., a heavy or light chain constant region or a poly-A tail of mRNA). In some embodiments, the reverse transcription primers can comprise a first reverse transcription primer with a region complementary to a constant region of a first RNA, and a second reverse transcription primer with a region complementary to a constant region of a second RNA. In some embodiments, the reverse transcription primers can comprise a first reverse transcription primer with a region complementary to a constant region of a first RNA, and one or more reverse transcription primers with a region complementary to a constant region of one or more RNAs, respectively.

In some embodiments, reverse transcription primers do not comprise a barcode.

Reverse transcription primers can further comprise a region that is not complementary to a region of the RNA. In some embodiments, the region that is not complementary to a region of the RNA is 5' to a region of the primers that is complementary to the RNA. In some embodiments, the region that is not complementary to a region of the RNA is 3' to a region of the primers that is complementary to the RNA. In some embodiments, the region that is not complementary to a region of the RNA is a 5' overhang region. In some embodiments, the region that is not complementary to a region of the RNA comprises a priming site for amplification and/or a sequencing reaction. Using the one or more primers described herein, the RNA molecules are reverse transcribed using suitable reagents known in the art.

After performing the reverse transcription reactions of the RNA molecules, the resulting cDNA molecules can be barcoded with a molecular barcode and a vessel barcode and amplified by one or more PCR reactions, such as a first and/or a second PCR reaction. The first and/or second PCR reaction can utilize a pair of primers or a plurality of primer pairs. The first and/or second PCR reaction can utilize a plurality of forward/reverse primers and a reverse primer. The first and/or second PCR reaction can utilize a plurality of forward/reverse primers and a forward primer. A first and/or second primer of a plurality of forward/reverse primers can be a forward/reverse primer containing a region complementary to the cDNA molecules or barcoded cDNA molecules. A first and/or second primer of a plurality of forward/reverse primers can be a forward/reverse primer containing a region complementary to the barcoded cDNA molecules.

In some embodiments, a plurality of forward/reverse primers comprises one or more forward/reverse primers wherein each of the forward/reverse primers in the plurality of forward/reverse primers comprises a region complementary to one or more upstream or downstream regions to a V segment of the cDNAs or barcoded cDNAs. For example, a plurality of forward/reverse primers comprises a forward/reverse primer comprising a region complementary to a upstream or downstream region to a V segment of the cDNAs or barcoded cDNAs and one or more other forward/reverse primers comprising a region complementary to one or more other upstream or downstream regions to a V segment of the cDNAs or barcoded cDNAs. For example, a plurality of forward/reverse primers comprises a first and/or second forward/reverse primer comprising a region complementary to a first and/or second upstream or downstream region to a V segment of the cDNAs or barcoded cDNAs and a second forward/reverse primer comprising a region complementary to a second upstream or downstream region to a V segment of the cDNAs or barcoded cDNAs. For example, a plurality of forward/reverse primers comprises a first and/or second forward/reverse primer comprising a region complementary to a first and/or second upstream or downstream region to a V segment of the cDNAs or barcoded cDNAs, a second forward/reverse primer comprising a region complementary to a second upstream or downstream region to a V segment of the cDNAs or barcoded cDNAs, and a third forward/reverse primer comprising a region complementary to a third upstream or downstream region to a V segment of the cDNAs or barcoded cDNAs, etc. The primers in the plurality of forward/reverse primers can be used to anneal to all possible upstream or downstream regions of all V segments expressed by the cells, such as immune B-cells or T-cells, in the sample.

In some embodiments, a plurality of forward/reverse primers comprises one or more forward/reverse primers wherein each of the forward/reverse primers in the plurality of forward/reverse primers comprises a region complementary to one or more upstream or downstream regions to a C segment of the cDNAs or barcoded cDNAs. For example, a plurality of forward/reverse primers comprises a forward/reverse primer comprising a region complementary to a upstream or downstream region to a C segment of the cDNAs or barcoded cDNAs and one or more other forward/reverse primers comprising a region complementary to one or more other upstream or downstream regions to a C segment of the cDNAs or barcoded cDNAs. For example, a plurality of forward/reverse primers comprises a first and/or second forward/reverse primer comprising a region complementary to a first and/or second upstream or downstream region to a C segment of the cDNAs or barcoded cDNAs and a second forward/reverse primer comprising a region complementary to a second upstream or downstream region to a C segment of the cDNAs or barcoded cDNAs. For example, a plurality of forward/reverse primers comprises a first and/or second forward/reverse primer comprising a region complementary to a first and/or second upstream or downstream region to a C segment of the cDNAs or barcoded cDNAs, a second forward/reverse primer comprising a region complementary to a second upstream or downstream region to a C segment of the cDNAs or barcoded cDNAs, and a third forward/reverse primer comprising a region complementary to a third upstream or downstream region to a C segment of the cDNAs or barcoded cDNAs, etc. The primers in the plurality of forward/reverse primers can be used to anneal to all possible upstream or downstream regions of all C segments expressed by the cells, such as immune B-cells or T-cells, in the sample.

In some embodiments, a plurality of forward/reverse primers comprises one or more forward/reverse primers wherein each of the forward/reverse primers in the plurality of forward/reverse primers comprises a region complementary to one or more upstream or downstream regions to a molecular barcode of the barcoded cDNAs. For example, a plurality of forward/reverse primers comprises a forward/reverse primer comprising a region complementary to a upstream or downstream region to a molecular barcode of the barcoded cDNAs and one or more other forward/reverse primers comprising a region complementary to one or more other upstream or downstream regions to a molecular barcode of the barcoded cDNAs. For example, a plurality of forward/reverse primers comprises a first and/or second forward/reverse primer comprising a region complementary to a first and/or second upstream or downstream region to a molecular barcode of the barcoded cDNAs and a second forward/reverse primer comprising a region complementary to a second upstream or downstream region to a molecular barcode of the barcoded cDNAs. For example, a plurality of forward/reverse primers comprises a first and/or second forward/reverse primer comprising a region complementary to a first and/or second upstream or downstream region to a molecular barcode of the barcoded cDNAs, a second forward/reverse primer comprising a region complementary to a second upstream or downstream region to a molecular barcode of the barcoded cDNAs, and a third forward/reverse primer comprising a region complementary to a third upstream or downstream region to a molecular barcode of the barcoded cDNAs, etc. The plurality of forward/reverse primers can be used to anneal to all possible upstream or downstream regions of all molecular barcodes expressed by the cells, such as immune B-cells or T-cells, in the sample.

In some embodiments, a plurality of forward/reverse primers comprises one or more forward/reverse primers wherein each of the forward/reverse primers in the plurality of forward/reverse primers comprises a region complementary to one or more upstream or downstream regions to a vessel barcode of the barcoded cDNAs. For example, a plurality of forward/reverse primers comprises a forward/reverse primer comprising a region complementary to a upstream or downstream region to a vessel barcode of the barcoded cDNAs and one or more other forward/reverse primers comprising a region complementary to one or more other upstream or downstream regions to a vessel barcode of the barcoded cDNAs. For example, a plurality of forward/reverse primers comprises a first and/or second forward/reverse primer comprising a region complementary to a first and/or second upstream or downstream region to a vessel barcode of the barcoded cDNAs and a second forward/reverse primer comprising a region complementary to a second upstream or downstream region to a vessel barcode of the barcoded cDNAs. For example, a plurality of forward/reverse primers comprises a first and/or second forward/reverse primer comprising a region complementary to a first and/or second upstream or downstream region to a vessel barcode of the barcoded cDNAs, a second forward/reverse primer comprising a region complementary to a second upstream or downstream region to a vessel barcode of the barcoded cDNAs, and a third forward/reverse primer comprising a region complementary to a third upstream or downstream region to a vessel barcode of the barcoded cDNAs, etc. The primers in the plurality of forward/reverse primers can be used to anneal to all possible upstream or downstream regions of all vessel barcodes expressed by the cells, such as immune B-cells or T-cells, in the sample.

The forward/reverse primers in the plurality of forward/reverse primers further comprise a region that is not complementary to a region of the RNA. In some embodiments, the region that is not complementary to a region of the RNA is 5' to a region of the forward/reverse primers that is complementary to the RNA (i.e. a upstream or downstream regions of a V segment). In some embodiments, the region that is not complementary to a region of the RNA is 3' to a region of the forward/reverse primers that is complementary to the RNA. In some embodiments, the region that is not complementary to a region of the RNA is a 5' overhang region. In some embodiments, the region that is not complementary to a region of the RNA comprises a priming site for amplification and/or a second sequencing reaction. In some embodiments, the region that is not complementary to a region of the RNA comprises a priming site for amplification and/or a third sequencing reaction. In some embodiments, the region that is not complementary to a region of the RNA comprises a priming site for a second and a third sequencing reaction. In some embodiments, the sequence of the priming site for the second and the third sequencing reaction are the same. Using the one or more forward/reverse primers and a reverse primer as described herein, the cDNA molecules are amplified using suitable reagents known in the art. In some embodiments, a region is complementary to a region of the RNA, such as the constant region or a poly-A tail of mRNA.

Amplification

The sample containing the target polynucleotide can comprise mRNA, or fragments thereof, which can be amplified. In some cases, the average length of the mRNA, or fragments thereof, can be less than about 100, 200, 300, 400, 500, or 800 base pairs, or less than about 5, 10, 20, 30, 40, 50, 60, 70, 80, 90, 100, 110, 120, 130, 140, 150, 160, 170, 180, 190, or 200 nucleotides, or less than about 1, 2, 5, 10, 20, 30, 40, 50, 60, 70, 80, 90, 100 kilobases. In some cases, a target sequence from a relative short template, such as a sample containing a template that is about 40, 45, 50, 55, 60, 65, 70, 75, 80, 85, 90, 95, or 100 bases, is amplified.

An amplification reaction can comprise one or more additives. In some cases, the one or more additives are dimethyl sulfoxide (DMSO), glycerol, betaine (mono)hydrate (N,N,N-trimethylglycine=[caroxy-methyl] trimethylammonium), trehalose, 7-Deaza-2'-deoxyguanosine triphosphate (dC7GTP or 7-deaza-2'-dGTP), BSA (bovine serum albumin), formamide (methanamide), tetramethylammonium chloride (TMAC), other tetraalkylammonium derivatives (e.g., tetraethyammonium chloride (TEA-Cl) and tetrapropylammonium chloride (TPrA-Cl), non-ionic detergent (e.g., Triton X-100, Tween 20, Nonidet P-40 (NP-40)), or PREXCEL-Q. In some cases, an amplification reaction comprises 0, 1, 2, 3, 4, 5, 6, 7, 8, 9, or 10 different additives. In other cases, an amplification reaction comprises at least 0, 1, 2, 3, 4, 5, 6, 7, 8, 9, or 10 different additives.

Thermocycling reactions can be performed on samples contained in reaction volumes (e.g., droplets). Droplets can be polydisperse or preferably monodisperse, generated through agitation, sonication or microfluidically through a T-channel junction or other means by those familiar with the art. Densities can exceed 20,000 droplets/40 ul (1 nL droplets), 200,000 droplets/40 ul (100 pL droplets). The droplets can remain intact during thermocycling. Droplets can remain intact during thermocycling at densities of greater than about 10,000 droplets/µL, 100,000 droplets/µL, 200,000 droplets/µL, 300,000 droplets/µL, 400,000 droplets/µL, 500,000 droplets/µL, 600,000 droplets/µL, 700,000 droplets/µL, 800,000 droplets/µL, 900,000 droplets/µL or 1,000,000 droplets/µL. In other cases, two or more droplets do not coalesce during thermocycling. In other cases, greater than 100 or greater than 1,000 droplets do not coalesce during thermocycling.

Any DNA polymerase that catalyzes primer extension can be used, including but not limited to $E.\ coli$ DNA polymerase, Klenow fragment of $E.\ coli$ DNA polymerase 1, T7 DNA polymerase, T4 DNA polymerase, Taq polymerase, Pfu DNA polymerase, Vent DNA polymerase, bacteriophage 29, REDTaq™, Genomic DNA polymerase, or sequenase. In some cases, a thermostable DNA polymerase is used. A hot start PCR can also be performed wherein the reaction is heated to 95° C. for two minutes prior to addition of the polymerase or the polymerase can be kept inactive until the first heating step in cycle 1. Hot start PCR can be used to minimize nonspecific amplification. Any number of PCR cycles can be used to amplify the DNA, e.g., about, more than about, or less than about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45 cycles. The number of amplification cycles can be about 1-45, 10-45, 20-45, 30-45, 35-45, 10-40, 10-30, 10-25, 10-20, 10-15, 20-35, 25-35, 30-35, or 35-40.

Amplification of target nucleic acids can be performed by any means known in the art. Target nucleic acids can be amplified by polymerase chain reaction (PCR) or isothermal DNA amplification. Examples of PCR techniques that can be used include, but are not limited to, quantitative PCR, quantitative fluorescent PCR (QF-PCR), multiplex fluorescent PCR (MF-PCR), real time PCR (reverse transcription-PCR), single cell PCR, restriction fragment length polymorphism PCR (PCR-RFLP), PCR-RFLP/reverse transcription-PCR-RFLP, hot start PCR, nested PCR, in situ polony PCR, in situ rolling circle amplification (RCA), digital PCR (dPCR), droplet digital PCR (ddPCR), bridge PCR, picoliter PCR and emulsion PCR. Other suitable amplification methods include the ligase chain reaction (LCR), transcription amplification, molecular inversion probe (MIP) PCR, self-sustained sequence replication, selective amplification of target polynucleotide sequences, consensus sequence primed polymerase chain reaction (CP-PCR), arbitrarily primed polymerase chain reaction (AP-PCR), degenerate polynucleotide-primed PCR (DOP-PCR) and nucleic acid based sequence amplification (NABSA). Other amplification methods that can be used herein include those described in U.S. Pat. Nos. 5,242,794; 5,494,810; 4,988,617; and 6,582,938, as well as include Q beta replicase mediated RNA amplification. Amplification can be isothermal amplification, e.g., isothermal linear amplification.

In some embodiments, amplification does not occur on a solid support. In some embodiments, amplification does not occur on a solid support in a droplet. In some embodiments, amplification does occur on a solid support when the amplification is not in a droplet.

An amplification reaction can comprise one or more additives. In some embodiments, the one or more additives are dimethyl sulfoxide (DMSO), glycerol, betaine (mono) hydrate (N,N,N-trimethylglycine=[caroxy-methyl] trimethylammonium), trehalose, 7-Deaza-2'-deoxyguanosine triphosphate (dC7GTP or 7-deaza-2'-dGTP), BSA (bovine serum albumin), formamide (methanamide), tetramethylammonium chloride (TMAC), other tetraalkylammonium derivatives (e.g., tetraethyammonium chloride (TEA-Cl) and tetrapropylammonium chloride (TPrA-Cl), non-ionic detergent (e.g., Triton X-100, Tween 20, Nonidet P-40 (NP-40)), or PREXCEL-Q. In some embodiments, an amplification reaction can comprise 0, 1, 2, 3, 4, 5, 6, 7, 8, 9, or 10 different additives. In other cases, an amplification reaction can comprise at least 0, 1, 2, 3, 4, 5, 6, 7, 8, 9, or 10 different additives.

Sequencing

After performing one or more of the methods or method steps described herein, a library of polynucleotides generated can be sequenced.

Sequencing can be performed by any sequencing method known in the art. In some embodiments, sequencing can be performed in high throughput. Suitable next generation sequencing technologies include the 454 Life Sciences platform (Roche, Branford, Conn.) (Margulies et al., Nature, 437, 376-380 (2005)); lllumina's Genome Analyzer, GoldenGate Methylation Assay, or Infinium Methylation Assays, i.e., Infinium HumanMethylation 27K BeadArray or VeraCode GoldenGate methylation array (Illumina, San Diego, Calif.; Bibkova et al., Genome Res. 16, 383-393 (2006); and U.S. Pat. Nos. 6,306,597, 7,598,035, 7,232,656), or DNA Sequencing by Ligation, SOLiD System (Applied Biosystems/Life Technologies; U.S. Pat. Nos. 6,797,470, 7,083,917, 7,166,434, 7,320,865, 7,332,285, 7,364,858, and 7,429,453); or the Helicos True Single Molecule DNA sequencing technology (Harris et al., Science, 320, 106-109 (2008); and U.S. Pat. Nos. 7,037,687, 7,645,596, 7,169,560, and 7,769,400), the single molecule, real-time (SMRT™) technology of Pacific Biosciences, and sequencing (Soni et al., Clin. Chem. 53, 1996-2001 (2007)). These systems allow multiplexed parallel sequencing of many polynucleotides isolated from a sample (Dear, Brief Funct. Genomic Proteomic, 1(4), 397-416 (2003) and McCaughan et al., J. Pathol., 220, 297-306 (2010)). In some embodiments, polynucleotides are sequenced by sequencing by ligation of dye-modified probes, pyrosequencing, or single-molecule sequencing. Determining the sequence of a polynucleotide may be performed by sequencing methods such as Helioscope™ single molecule sequencing, Nanopore DNA sequencing, Lynx Therapeutics' Massively Parallel Signature Sequencing (MPSS), 454 pyrosequencing, Single Molecule real time (RNAP) sequencing, Illumina (Solexa) sequencing, SOLiD sequencing, Ion Torrent™, Ion semiconductor sequencing, Single Molecule SMRT™ sequencing, Polony sequencing, DNA nanoball sequencing, and VisiGen Biotechnologies approach. Alternatively, determining the sequence of polynucleotides may use sequencing platforms, including, but not limited to, Genome Analyzer IIx, HiSeq, and MiSeq offered by Illumina, Single Molecule Real Time (SMRT™) technology, such as the PacBio RS system offered by Pacific Biosciences (California) and the Solexa Sequencer, True Single Molecule Sequencing (tSMS™) technology such as the HeliScope™ Sequencer offered by Helicos Inc. (Cambridge, Mass.). Sequencing can comprise MiSeq sequencing. Sequencing can comprise HiSeq sequencing. In some embodiments, determining the sequence of a polynucleotide comprises paired-end sequencing, nanopore sequencing, high-throughput sequencing, shotgun sequencing, dye-terminator sequencing, multiple-primer DNA sequencing, primer walking, Sanger dideoxy sequencing, Maxim-Gilbert sequencing, pyrosequencing, true single molecule sequencing, or any combination thereof. Alternatively, the sequence of a polynucleotide can be determined by electron microscopy or a chemical-sensitive field effect transistor (chemFET) array.

A method can further comprise sequencing one or more polynucleotides in the library. A method can further comprise aligning one or more polynucleotide sequences, sequence reads, amplicon sequences, or amplicon set sequences in the library to each other.

As used herein, aligning comprises comparing a test sequence, such as a sequence read, to one or more other test sequences, reference sequences, or a combination thereof. In some embodiments, aligning can be used to determine a consensus sequence from a plurality of sequences or aligned sequences. In some embodiments, aligning comprises determining a consensus sequence from a plurality of sequences that each has an identical molecular barcode or vessel barcode. In some embodiments, the length of a sequence aligned for comparison purposes is at least 30%, at least 40%, at least 50%, at least 60%, at least 70%, at least 80%, at least 90%, or at least 95%, of the length of a reference sequence. The actual comparison of the two or more sequences can be accomplished by well-known methods, for example, using a mathematical algorithm. A non-limiting example of such a mathematical algorithm is described in Karlin, S. and Altschul, S., Proc. Natl. Acad. Sci. USA, 90-5873-5877 (1993). Such an algorithm is incorporated into the NBLAST and XBLAST programs (version 2.0), as described in Altschul, S. et al., Nucleic Acids Res., 25:3389-3402 (1997). When utilizing BLAST and Gapped BLAST programs, any relevant parameters of the respective programs (e.g., NBLAST) can be used. For example, parameters for sequence comparison can be set at score=100, word length=12, or can be varied (e.g., W=5 or W=20). Other examples include the algorithm of Myers and Miller, CABIOS (1989), ADVANCE, ADAM, BLAT, and FASTA. In some embodiments, the percent identity between two amino acid sequences can be accomplished using, for example, the GAP program in the GCG software package (Accelrys, Cambridge, UK).

Sequencing can comprise sequencing at least about 10, 20, 30, 40, 50, 60, 70, 80, 90, 100 or more nucleotides or base pairs of the polynucleotides. In some embodiments, sequencing comprises sequencing at least about 200, 300, 400, 500, 600, 700, 800, 900, 1000, or more nucleotides or base pairs of the polynucleotides. In other instances, sequencing comprises sequencing at least about 1500, 2000, 3000, 4000, 5000, 6000, 7000, 8000, 9000, 10,000, or more nucleotides or base pairs of the polynucleotides.

Sequencing can comprise at least about 200, 300, 400, 500, 600, 700, 800, 900, 1000 or more sequencing reads per run. As used herein, a sequence read comprises a sequence of nucleotides determined from a sequence or stream of data generated by a sequencing technique. In some embodiments, sequencing comprises sequencing at least about 1500, 2000, 3000, 4000, 5000, 6000, 7000, 8000, 9000, 10,000, or more sequencing reads per run. Sequencing can comprise more than, less than, or equal to about 1,000,000,000 sequencing reads per run. Sequencing can comprise more than, less than, or equal to about 200,000,000 reads per run.

In some embodiments, the number of sequence reads used to determine a consensus sequence is from about 2-1000 sequence reads. For example, the number of sequence reads used to determine a consensus sequence can be from about 2-900, 2-800, 2-700, 2-600, 2-500, 2-400, 2-300, 2-200, 2-100, 25-900, 25-800, 25-700, 25-600, 25-500, 25-400, 25-300, 25-200, 25-100, 100-1000, 100-900, 100-800, 100-700, 100-600, 100-500, 100-400, 100-300, 100-200, 200-1000, 200-900, 200-800, 200-700, 200-600, 200-500, 200-400, 200-300, 300-1000, 300-900, 300-800, 300-700, 300-600, 300-500, 300-400, 400-1000, 400-900, 400-800, 400-700, 400-600, 400-500, 500-1000, 500-900, 500-800, 500-700, 500-600, 600-1000, 600-900, 600-800, 600-700, 700-1000, 700-900, 700-800, 800-1000, 800-900, or 900-1000 sequence reads. In some embodiments, the number of sequence reads used to determine a consensus sequence is at least about 1000, 1500, 2000, 3000, 4000, 5000, 6000, 7000, 8000, 9000, 10,000, 11,000, 12,000, 13,000, 14,000, 15,000, 16,000, 17,000, 18,000, 19,000, 20,000, 25,000, 30,000, 35,000, 40,000, 45,000, 50,000, 55,000, 60,000, 65,000, 70,000, 75,000, 80,000, 85,000, 90,000, 95000, 100,000, 150,000, 200,000, 250,000, 300,000, 350,000, 400,000, 450,000, 500,000, 550,000, 600,000, 650,000, 700,000, 750,000, 800,000, 850,000, 900,000, 950,000, 1,000,000, 50,000,000, or 100,000,000 reads. In some embodiments, the number of sequence reads used to determine a consensus sequence is at most about 1000, 1500, 2000, 3000, 4000, 5000, 6000, 7000, 8000, 9000, 10,000, 11,000, 12,000, 13,000, 14,000, 15,000, 16,000, 17,000, 18,000, 19,000, 20,000, 25,000, 30,000, 35,000, 40,000, 45,000, 50,000, 55,000, 60,000, 65,000, 70,000, 75,000, 80,000, 85,000, 90,000, 95000, 100,000, 150,000, 200,000, 250,000, 300,000, 350,000, 400,000, 450,000, 500,000, 550,000, 600,000, 650,000, 700,000, 750,000, 800,000, 850,000, 900,000, 950,000, 1,000,000, 50,000,000, or 100,000,000 reads.

A method can comprise sequencing mis-reads. A method can comprise determining the number of mis-reads, such as for determining a reaction condition or designing primer sequences. Comparing the number of mis-reads generated under one or more first conditions or sets of conditions can be used to determine a preferred condition or condition set. For example, a first method can be carried out at a high salt concentration during a PCR reaction, and a second method can be carried out at a low salt concentration during a PCR reaction, wherein the first and second method are carried out substantially the same aside from the salt concentration difference. If the first method results in a higher number of mis-reads, such as a higher number of mis-reads for a particular target polynucleotide sequence or primer, a lower salt reaction condition can be determined to be preferred for that particular target polynucleotide sequence or primer.

Enzymes

The methods and kits disclosed herein may comprise one or more enzymes. Examples of enzymes include, but are not limited to ligases, reverse transcriptases, polymerases, and restriction nucleases.

In some embodiments, attachment of an adaptor to polynucleotides comprises the use of one or more ligases. Examples of ligases include, but are not limited to, DNA ligases such as DNA ligase I, DNA ligase III, DNA ligase IV, and T4 DNA ligase, and RNA ligases such as T4 RNA ligase I and T4 RNA ligase II.

The methods and kits disclosed herein may further comprise the use of one or more reverse transcriptases. In some embodiments, the reverse transcriptase is a HIV-1 reverse transcriptase, M-MLV reverse transcriptase, AMV reverse transcriptase, and telomerase reverse transcriptase. In some embodiments, the reverse transcriptase is M-MLV reverse transcriptase.

In some embodiments, the methods and kits disclosed herein comprise the use of one or more proteases.

In some embodiments, the methods and kits disclosed herein comprise the use of one or more polymerases. Examples of polymerases include, but are not limited to, DNA polymerases and RNA polymerases. In some embodiments, the DNA polymerase is a DNA polymerase I, DNA polymerase DNA polymerase III holoenzyme, and DNA polymerase IV. Commercially available DNA polymerases include, but are not limited to, Bst 2.0 DNA Polymerase, Bst 2.0 WarmStart™ DNA Polymerase, Bst DNA Polymerase, Sulfolobus DNA Polymerase IV, Taq DNA Polymerase, 9° NTMm DNA Polymerase, Deep VentR™ (exo-) DNA Polymerase, Deep VentR™ DNA Polymerase, Hemo KlenTaq™, LongAmp® Taq DNA Polymerase, OneTaq® DNA Polymerase, Phusion® DNA Polymerase, Q5™ High-Fidelity DNA Polymerase, Therminator™ γ DNA Polymerase, Therminator™ DNA Polymerase, Therminator™ II DNA Polymerase, Therminator™ III DNA Polymerase, VentR® DNA Polymerase, VentR® (exo-) DNA Polymerase, Bsu DNA Polymerase, phi29 DNA Polymerase, T4 DNA Polymerase, T7 DNA Polymerase, Terminal Transferase, Titanium® Taq Polymerase, KAPA Taq DNA Polymerase and KAPA Taq Hot Start DNA Polymerase.

In some embodiments, the polymerase is an RNA polymerases such as RNA polymerase I, RNA polymerase II, RNA polymerase III, *E. coli* Poly(A) polymerase, phi6 RNA polymerase (RdRP), Poly(U) polymerase, SP6 RNA polymerase, and T7 RNA polymerase.

Artificial Antigen Presenting Cells (aApcs) and APC Reporters

Artificial antigen presenting cells (aAPCs), also referred to herein as engineered APCs (eAPC) may refer to APC cells (in some embodiments, cells based on the K562 cell line) that do not express endogenous MHC proteins. In some embodiments, the aAPC cells are transfected with MHC gene(s) matched to those of the source organism of the TCR under investigation. aAPCs can be further transfected with an expression vector coding for peptide antigens of interest or pulsed with a library of target antigens.

In some embodiments, aAPCs are additionally engineered to contain a reporter gene construct which can express a reporter (e.g. luciferase, fluorescent protein, surface protein) upon antigen recognition by a T cell. In some aspects, APCs (and aAPCs) that express a reporter upon recognition by and/or engagement with a T cell are deemed to have reactivity to the T cell. Expression of these reporter genes can be a method of detecting binding of an aAPC to a T cell, thereby allowing for identification of a target antigen of a TCR of interest. In some embodiments, the target antigen is not known. In some embodiments, the TCR comprises a TCR with known variable region sequences. For example, the methods described herein can comprise identifying an unknown target antigen of a TCR with known variable region sequences of interest In some embodiments, detection of an aAPC that has become activated by binding of MHC-peptide complexes to a TCR can result in expression of a reporter gene. In some embodiments, the reporter is a fluorescent protein such as luciferase, red fluorescent protein, green fluorescent protein, yellow fluorescent protein, a green fluorescent protein derivative, or any engineered fluorescent protein. In further embodiments, detection of the fluorescent reporter can be detected using fluorescence techniques. For example, fluorescent protein expression can be measured using a fluorescence plate reader, flow cytometry, or fluorescence microscopy. In some embodiments, the activated APC can be sorted based on expression of a fluorescent reporter using a fluorescence activated cell sorter (FACS).

In some embodiments, detection of an aAPC that is activated by binding of MHC-peptide complexes to a TCR can result in expression of a reporter gene that encodes for a cell-surface marker. APCs can upregulate or downregulate various cell surface markers upon engaging a TCR. In some embodiments, the level of expression of a cell surface protein such as CD80, CD86, MHC I, MHC II, CD11c, CD11b, CD8α, OX40-L, ICOS-1, or CD40 can change (e.g., increase or decrease after binding of an MHC-peptide complex to a TCR. In some embodiments, detection of the cell surface reporter can be detected using techniques such as immunohistochemistry, fluorescence staining and quantification by flow cytometry, or assaying for changes in gene expression with cDNA arrays or mRNA quantification. In some embodiments, the activated APC can be isolated based on expression of a cell surface reporter using magnetic activated cell sorting.

In some embodiments, detection of an aAPC that is activated by binding of MHC-peptide complexes to a TCR can result in expression of a reporter gene that encodes for a secreted factor such as IL6, IL-12, IFNα, IL-23, IL-1, TNF, or IL-10. In further embodiments, these secreted factors can be detected by mRNA quantification, cDNA arrays, or quantification of expressed proteins by assays such as an enzyme-linked immunosorbent assay (ELISA) or an enzyme linked immunospot (ELISPOT).

In some embodiments, expression of a reporter gene in aAPCs can be triggered by binding of a signal by engineered T cells during T cell activation. For example, APCs presenting antigens of interest can be engineered to also express a synthetic Notch (synNotch) receptor. In some embodiments, the synNotch receptor is a transcellular protein with an external and an internal domain. In some embodiments, synNotch can bind to target antigens at the same time as formation of the MHC-peptide TCR complex. In still other embodiments, synNotch can bind to target antigens after formation of the MHC-peptide TCR complex. Upon binding of synNotch to target antigens, the internal domain of the receptor is cleaved giving rise to a transcriptional activation domain that migrates to the nucleus and promotes expression of a reporter gene by the APC. In some aspects, the synthetic Notch receptor expressed by the APC recognizes a protein ligand and/or antigen expressed by a target T cell only when said T cell is activated (e.g. by TCR engagement with the appropriate MHC-peptide complex).

In some embodiments, the reporter system expressed by the APC and/or engineered/artificial APC comprises a signaling system comprising a component that is able to be cleaved by one or more effector agents (e.g. an enzyme) that are secreted when an engineered T cell recognizes its cognate antigen (e.g., recognizes the MHC-peptide complex presented on the APC). In some embodiments, this system is a FRET-based detection system. Exemplary systems may be found in international patent application publication number WO2015143558. In some aspects, engagement of the aAPC with the engineered T-cell results in activation of the T-cell and/or release of enzymes, cytokines, and/or chemokines. In some aspects these enzymes, cytokines, and/or chemokines represent cytotoxic signals and/or effector functions. In some aspects, effector agents include, but are not limited to, granzymes, perforins, and granulysins. In some embodiments, upon contact and specific recognition of T cell receptor and MHC-epitope complex, an engineered T cell is activated and produces granules that contain a variety of effector agents, including granzyme proteases and perforins. In some aspects, granules of the activated engineered T cell are transported to the cell surface and released into the intercellular environment adjacent to the aAPC. In some aspects, perforins form pores through the cell membrane of reporter cell, thereby allowing granzymes and other effector agents to enter the cytosol of a reporter cell (e.g. aAPC). In some embodiments, the signaling system and/or reporter construct may comprise a quenched fluorescent protein that may be unquenched by enzymatic cleavage (e.g. granzyme cleavage) of a peptide link that releases a fluorescent moiety to generate signal. In some aspects, the reporter construct comprises a FRET-based fluorescent protein signaling system that generates a fluorescent signal when cleaved (e.g. enzymatically cleaved) by an effector agent delivered to the aAPC by the engineered T cell. In one aspect, the reporter construct comprises a genetically-encoded CFP-YFP fusion FRET pair separated by a granzyme B (GzmB)-cleavable linker.

In some embodiments, a system for measuring APC activation comprises an engineered APC comprising a synthetic reporter, such as a synthetic Notch receptor. In some embodiments, the synthetic reporter is a receptor comprising an intracellular domain. The intracellular domain can comprise a transcription activator protein. For example, the intracellular domain can comprise a GAL4-VP64 domain. In some embodiments, the synthetic reporter is constitutively expressed in the engineered APC.

In some embodiments, a system for measuring APC activation comprises an engineered T-cell comprises a gene encoding a cell surface expressed protein ligand under control of an inducible promoter, such as a NFAT promoter. The synthetic reporter, such as a synthetic Notch receptor, can specifically bind the cell surface expressed protein ligand on the cell surface of the engineered T-cell.

In some embodiments, a system for measuring APC activation comprises a fluorescent reporter downstream of an activating sequence within the APC. For example, the activating sequence can be GAL4-UAS. In the system for measuring APC activation described herein, under non-stimulatory conditions, the T-cell does not express the protein ligand on its surface. Upon contact and subsequent stimulation with an APC presenting a cognate MHC-peptide complex of a TCR expressed on a T-cell, the T-cell's reporter becomes active and the cell surface ligand is expressed. For example, this protein ligand interacts with the extracellular domain of the synthetic Notch receptor on the APC, causing the intracellular GAL4-VP64 domain to be cleaved within the APC. Upon cleavage, the GAL4-VP64 domain transits to the nucleus and activates the fluorescent reporter downstream of the GAL4-UAS sequence.

Identifying TCR Antigen Targets

Natively paired TCR chains of interest can be transfected into T cells using expression vectors. In some embodiments, the T cell line is engineered to lack endogenous TCR expression. In some aspects, exemplary T cell lines include Jurkat cell lines. In some aspects, T cells expressing a TCR of interest are cultured with aAPCs (described above) presenting a library of antigens on MHC molecules matching the host organism from which the TCR of interest was derived. In some embodiments, a T cell binds an aAPC via engagement of MHC-peptide complexes via the TCR, and results in expression of a reporter gene by the APC, as described above. Activated APCs can be isolated using fluorescence activated cell sorting (FACS) or magnetic activated cell sorting (MACS). In some embodiments, antigenic peptides can be eluted off of the MHC molecule by treatment with an acid and/or reverse phase HPLC (RP-HPLC). In further embodiments, the antigenic peptide can be sequenced or analyzed by mass spectrometry. This method allows rapid and simultaneous screening of a large panel of target antigens against a TCR of interest, thereby allowing for accurate identification of the target antigen of a TCR.

In some embodiments, pools of antigens can be deconvoluted. For example, engineered T-cells expressing a TCR from a subject can be contacted with a pool of engineered APCs comprising engineered APCs expressing a plurality of antigen targets. For example, engineered T-cells expressing a TCR from a subject can be contacted with a pool of engineered APCs comprising engineered APCs expressing a first antigen target and engineered APCs expressing a second antigen target. For example, engineered T-cells expressing a TCR from a subject can be contacted with a first pool of engineered APCs comprising engineered APCs expressing a first antigen target and engineered APCs expressing a second antigen target, and engineered T-cells expressing the TCR can be contacted with a second pool of engineered APCs comprising engineered APCs expressing a third antigen target and engineered APCs expressing a fourth antigen target.

For example, engineered T-cells expressing a first TCR from a subject can be contacted with a pool of engineered APCs comprising engineered APCs expressing a first antigen target and engineered APCs expressing a second antigen target, and engineered T-cells expressing a second TCR from a subject can be contacted with a pool of engineered APCs comprising the engineered APCs expressing the first antigen target and the engineered APCs expressing the second antigen target.

For example, engineered T-cells expressing a first TCR from a subject can be contacted with a pool of engineered APCs comprising engineered APCs expressing a first antigen target and engineered APCs expressing a second antigen target, and engineered T-cells expressing a second TCR from the subject can be contacted with another pool of engineered APCs comprising the engineered APCs expressing a first antigen target and the engineered APCs expressing a second antigen target.

For example, engineered T-cells expressing a first TCR from a subject can be contacted with a first pool of engineered APCs comprising engineered APCs expressing a first antigen target and engineered APCs expressing a second antigen target, and engineered T-cells expressing the first TCR can be contacted with a second pool of engineered APCs comprising engineered APCs expressing a third antigen target and engineered APCs expressing a fourth antigen target; and engineered T-cells expressing a second TCR from a subject can be contacted with a another first pool of engineered APCs comprising the engineered APCs expressing the first antigen target and the engineered APCs expressing the second antigen target, and engineered T-cells expressing the second TCR can be contacted with another second pool of engineered APCs comprising the engineered APCs expressing the third antigen target and the engineered APCs expressing the fourth antigen target.

The APCs in a vessel, such as a well, containing activated APCs can be replated into 2 or more vessels, such as wells, such that the two or more vessels contain a subset of the APCs from the vessel from which they came. For example, the APCs in a vessel, such as a well, containing activated APCs can be replated into 2 or more vessels, such as wells, such that the two or more vessels contain a lower number of APCs than the vessel from which they came. In some embodiments, the APCs in a vessel, such as a well, containing activated APCs can be replated into 2 or more vessels, such as wells, such that the two or more vessels contain a single APC.

The replated APCs can then be assayed for activation by the engineered T-cells expressing the one or more TCRs from a subject. The antigen of the replated APCs that are activated can then be identified. For example, the gene encoding the antigen in replated APCs that are activated can then be amplified and sequenced.

In some embodiments, next generation sequencing can be used to identify the antigen. For example, a subpool of a population of APCs each expressing one of "m" antigens, can be plated into "o" number of wells, such that there are "n" number of antigens expressed in any well, where "in" is less than "m". For example, the subpool size and number of wells can be balanced such that multiple wells will contain APCs expressing each of the "m" antigens. Each well can then be assayed with engineered T-cells expressing a TCR of interest. Wells containing activated APCs can then be collected. The antigen of the collected APCs can then be identified. For example, DNA encoding the antigen expressed in the collected APCs can be amplified and subsequently sequenced, such as by a next generation sequencing method. The set of antigens in a first well containing activated APCs can be compared to the set of antigens in a second well containing activated APCs. For example, the set of antigens in the well containing activated APCs can be compared to the set of antigens in each other well containing activated APCs. An identified antigen from a first set of antigens in a well containing activated APCs that is the same as an identified antigen in a second set of antigens in another well can be identified as a target antigen of the TCR. For example, an identified antigen from the set of antigens in the well containing activated APCs that is the same as an identified antigen in each of the sets of antigens in each other well can be identified as a target antigen of the TCR.

Identifying Antigen-Specific TCRS

The present disclosure provides methods to identify human-derived TCRs that are reactive to an antigen of interest, thereby allowing for the discovery of therapeutically relevant TCRs. In some embodiments, the antigen of interest can be representative of a disease condition, such as cancer. In some embodiments, various TCRs of tumor infiltrating lymphocytes can be transfected into T cell lines expressing the CD4 and CD8 co-receptor. In some embodiments, the T cell line is engineered to lack endogenous TCR expression. In some aspects, exemplary T cell lines include Jurkat cell lines. In some embodiments, TCRs can be isolated from T cells of multiple patients, giving multiple populations of T cells. T cells expressing various TCRs of interest can be cultured with aAPCs presenting a target antigen of interest. In some embodiments, the aAPCs are made of a multiple populations of aAPCs in which each population has can be transfected with an MHC molecule to match each T cell population present in the co-culture, all presenting the same target antigen. In some aspects, TCR-expressing T cells that induce expression of the reporter gene in the aAPCs are isolated and analyzed to determine TCRs reactive to antigen of interest.

In some embodiments, the identified TCRs that are reactive to a target antigen representative of a disease condition can be engineered in T cells and used as an immunotherapy. In certain embodiments, this T cell immunotherapy can be administered to a subject in need thereof to treat the condition.

Methods of Treatment

The present disclosure provides methods for treatment of a subject in need thereof with therapeutics against the identified target antigens of natively paired TCR chains. In some embodiments, subject in need thereof can be a human. The subject can have a disease in which a target antigen is expressed. For example, the disease can be cancer including, B-cell lymphoma, acute lymphoblastic leukemia (ALL), chronic lymphocytic leukemia, acute myeloid leukemia, adrenocortical carcinoma, adrenal cortex cancer, AIDS-related cancers, anal cancer, appendix cancer, astrocytomas, atypical teratoid/rhabdoid tumor, basal cell carcinoma, bile duct cancer, extrahepatic, bladder cancer, bone cancer (includes ewing sarcoma and osteosarcoma and malignant fibrous histiocytoma), brain tumors, breast cancer, burkitt lymphoma, carcinoid tumor (gastrointestinal), carcinoma of unknown primary, central nervous system, lymphoma, primary, cervical cancer, cholangiocarcinoma, chronic lymphocytic leukemia (cll), chronic myelogenous leukemia (cml), chronic myeloproliferative neoplasms, colorectal cancer, cutaneous t-cell lymphoma, ductal carcinoma in situ (dcis), endometrial cancer, esophageal, ewing sarcoma, extragonadal germ cell tumor, eye cancer, intraocular melanoma, retinoblastoma, fallopian tube cancer, fibrous histiocytoma of bone, malignant, and osteosarcoma, gallbladder cancer, gastric (stomach) cancer, gastrointestinal carcinoid tumor, gastrointestinal stromal tumors (gist), germ cell tumors, extragonadal, ovarian, testicular, gestational trophoblastic disease, gliomas, hairy cell leukemia, head and neck cancer, hepatocellular (liver) cancer, histiocytosis, langerhans cell, hodgkin lymphoma, hypopharyngeal cancer, intraocular melanoma, islet cell tumors, pancreatic neuroendocrine tumors, kaposi sarcoma, kidney, langerhans cell histiocytosis, laryngeal cancer, leukemia, lip and oral cavity cancer, liver cancer (primary), lung cancer, lymphoma, macroglobulinemia, waldenstrom, male breast cancer, malignant fibrous histiocytoma of bone and osteosarcoma, melanoma, melanoma, intraocular (eye), merkel cell carcinoma, mesothelioma, malignant, metastatic squamous neck cancer with occult primary, mouth cancer, multiple myeloma/plasma cell neoplasms, mycosis fungoides, myelodysplastic syndromes, myelodysplastic/myeloproliferative neoplasms and chronic myeloproliferative neoplasms, myelogenous leukemia, chronic (cml), myeloid leukemia, acute (AML), nasal cavity and paranasal sinus cancer, nasopharyngeal cancer, neuroblastoma, non-hodgkin lymphoma, non-small cell lung cancer, oral cancer, lip and oral cavity cancer and oropharyngeal cancer, osteosarcoma and malignant fibrous histiocytoma of bone, ovarian cancer, pancreatic cancer and pancreatic neuroendocrine tumors (islet cell tumors), paraganglioma, paranasal sinus and nasal cavity cancer, parathyroid cancer, penile cancer, pharyngeal cancer, pheochromocytoma, pituitary tumor, plasma cell neoplasm/multiple myeloma, pregnancy and breast cancer, primary central nervous system (CNS) lymphoma, primary peritoneal cancer, prostate cancer, rectal cancer, renal cell (kidney) cancer, retinoblastoma, salivary gland cancer, sarcoma, ewing sarcoma, kaposi sarcoma, osteosarcoma, rhabdomyosarcoma, uterine sarcoma, sézary syndrome, skin cancer, small cell lung cancer, small intestine cancer, soft tissue sarcoma, squamous cell carcinoma, squamous neck cancer with occult primary, metastatic, stomach (gastric) cancer, t-cell lymphoma, cutaneous, testicular cancer, throat cancer, thymoma and thymic carcinoma, thyroid cancer, transitional cell cancer of the renal pelvis and ureter, ureter and renal pelvis, transitional cell cancer, urethral cancer, uterine cancer, endometrial and uterine sarcoma, vaginal cancer, vulvar cancer, waldenstrom macroglobulinemia, or wilms tumor In some embodiments, a target antigen can be associated with any cancer. In some embodiments, a sample can be taken from a patient and screened against TCRs using the methods described above. Using the methods provided in the present disclosure a target antigen can be identified by reactivity of engineered T cells. In certain embodiments, a patient can then be treated with a therapeutic against the target antigen. For example, a patient can be administered an effective dose of a small molecule, antibody, peptide or protein biologic, or immunotherapy targeted to the identified antigen. In some embodiments, the immunotherapy can include T cells engineered to express the TCR specific to the target antigen.

In some embodiments, a therapeutic agent against the target antigen may be a TCR or a TCR-like chimeric antigen receptor (CAR). In some aspects, a TCR-like CAR specifically binds to and/or recognizes protein epitopes in the context of MHC. Exemplary antigen receptors, including CARs, and methods for engineering and introducing such receptors into cells, include those described, for example, in international patent application publication numbers WO200014257, WO2013126726, WO2012/129514, WO2014031687, WO2013/166321, WO2013/071154, WO2013/123061 U.S. patent application publication numbers US2002131960, US2013287748, US20130149337, U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, and 8,479,118, and European patent application number EP2537416, and/or those described by Sadelain et al., Cancer Discov. 2013 April; 3(4): 388-398; Davila et al. (2013) PLoS ONE 8(4): e61338; Turtle et al., Curr. Opin. Immunol., 2012 October; 24(5): 633-39; Wu et al., Cancer, 2012 Mar. 18(2): 160-75. Examples of the CARs include CARs as disclosed in any of the aforementioned publications, such as WO2014031687, U.S. Pat. Nos. 8,339,645, 7,446,179, US 2013/0149337, U.S. Pat. Nos. 7,446,190, 8,389,282, Kochenderfer et al., 2013, Nature Reviews Clinical Oncology, 10, 267-276 (2013); Wang et al. (2012) J. Immunother. 35(9): 689-701; and Brentjens et al., Sci Transl Med. 2013 5(177). See also WO2014031687, U.S. Pat. Nos. 8,339,645, 7,446,179, US 2013/0149337, U.S. Pat. Nos. 7,446,190, and 8,389,282. The chimeric receptors, such as TCR-like CARs, generally include an extracellular antigen binding domain, such as a portion of an antibody molecule, generally a variable heavy (VH) chain region and/or variable light (VL) chain region of the antibody, e.g., an scFv and/or scTv antibody fragment. Also provided are methods involving the engineering of antibody fragments that specifically bind to and/or recognize epitopes generally recognized by TCRs, such as peptide epitopes in the context of MHC, such as TCR-like scFvs and/or scTvs, and/or for the generation and/or engineering of TCRs having certain features of scFvs, such as of such TCR-like scFvs and/or scTvs, for example, containing one or more CDRs thereof.

In some embodiments, a TCR-like chimeric antigen receptor (CAR) can comprise an intracellular domain comprising an intracellular domain of a T cell receptor, and an extracellular portion comprising a TCR-like antigen binding portion of an antibody, e.g., a TCR-like sFv and/or scTvs of an antibody. Generally, a chimeric receptor (e.g. a TCR-like CAR) comprises a linker or spacer domain between the antigen binding portion and the transmembrane domain. In some embodiments, the linker or spacer is derived from an immunoglobulin hinge region. In some embodiments, a nucleic acid encoding a TCR-like CAR construct, in some embodiments a TCR-like CAR vector, in addition to encoding an intracellular domain comprising an intracellular domain of a T cell receptor, and an extracellular portion comprising an antigen binding portion of an antibody, e.g., an sFv of an antibody and/or scTv, can comprise a promoter. For example, a promoter can be a synthetic promoter that contains a U3 region of a modified MoMuLV LTR with myleloproliferative sarcoma virus enhancer. In some embodiments, a promoter can be an EFla promoter or an EF1 promoter. In some embodiments, a TCR-like CAR can comprise an intracellular domain comprising a co-stimulatory domain and an intracellular domain of a T cell receptor, and an extracellular portion comprising an antibody, such as one or more antibodies provided herein, which may be a single-chain antibody or fragment thereof. In some embodiments, the antibody is or comprises an sV, an scFv, and/or an scTv. In some embodiments, the TCR-like CAR may further include additional extracellular portion(s), such as a spacer and/or hinge region.

In some aspects, the linkers rich in glycine and serine (and/or threonine) include at least 80, 85, 90, 91, 92, 93, 94, 95, 96, 97, 98, or 99% such amino acid(s). In some embodiments, they include at least at or about 50%, 55%, 60%, 70%, or 75%, glycine, serine, and/or threonine. In some embodiments, the linker is comprised substantially entirely of glycine, serine, and/or threonine. The linkers generally are between about 5 and about 50 amino acids in length, typically between at or about 10 and at or about 30, e.g., 10, 11, 12, 13, 14, 15, 16, 17, 18, 19, 20, 21, 22, 23, 24, 25, 26, 27, 28, 29, or 30, and in some examples between 10 and 25 amino acids in length. Exemplary linkers include linkers having various numbers of repeats of the sequence GGGGS (4GS) or GGGS (3GS), such as between 2, 3, 4, and 5 repeats of such a sequence. Exemplary linkers include those having or consisting of a GGGGSGGGGSGGGGS. Exemplary linkers further include those having or consisting of the sequence GSTSGSGKPGSGEGSTKG.

In some embodiments, the intracellular signaling domain includes intracellular signaling domains of costimulatory receptors such as CD28, CD137 (4-1 BB), OX40, and/or ICOS. In some embodiments, the TCR-like CAR includes a primary cytoplasmic signaling sequence that regulates primary activation of the TCR complex. Primary cytoplasmic signaling sequences that act in a stimulatory manner may contain signaling motifs which are known as immunoreceptor tyrosine-based activation motifs or ITAMs. Examples of ITAM containing primary cytoplasmic signaling sequences include those derived from TCR zeta, FcR gamma, FcR beta, CD3 gamma, CD3 delta, CD3 epsilon, CD8, CD22, CD79a, CD79b, and CD66d. In some embodiments, cytoplasmic signaling molecule(s) in the TCR-like CAR contain(s) a cytoplasmic signaling domain, portion thereof, or sequence derived from CD3 zeta.

In some embodiments, the methods include adoptive cell therapy, whereby genetically engineered cells expressing the provided antibodies, TCR-like CARs, and/or TCRs, or fragments thereof, are administered to subjects. Such administration can promote activation of the cells (e.g., T cell activation) in a targeted manner, such that the cells of the disease or disorder are targeted for destruction.

Thus, the provided methods and uses include methods and uses for adoptive cell therapy. In some embodiments, the methods include administration of the cells or a composition containing the cells to a subject, tissue, or cell, such as one having, at risk for, or suspected of having the disease, condition or disorder. In some embodiments, the cells, populations, and compositions are administered to a subject having the particular disease or condition to be treated, e.g., via adoptive cell therapy, such as adoptive T cell therapy. In some embodiments, the cells or compositions are administered to the subject, such as a subject having or at risk for the disease or condition. In some aspects, the methods thereby treat, e.g., ameliorate one or more symptom of the disease or condition.

Methods for administration of cells for adoptive cell therapy are known and may be used in connection with the provided methods and compositions. For example, adoptive T cell therapy methods are described, e.g., in US Patent Application Publication No. 2003/0170238 to Gruenberg et al; U.S. Pat. No. 4,690,915 to Rosenberg; Rosenberg (2011) Nat Rev Clin Oncol. 8(10):577-85). See, e.g., Themeli et al. (2013) Nat Biotechnol. 31(10): 928-933; Tsukahara et al. (2013) Biochem Biophys Res Commun 438(1): 84-9; Davila et al. (2013) PLoS ONE 8(4): e61338.

In some embodiments, the cell therapy, e.g., adoptive cell therapy, e.g., adoptive T cell therapy, is carried out by autologous transfer, in which the cells are isolated and/or otherwise prepared from the subject who is to receive the cell therapy, or from a sample derived from such a subject. Thus, in some aspects, the cells are derived from a subject, e.g., patient, in need of a treatment and the cells, following isolation and processing are administered to the same subject.

In some embodiments, the cell therapy, e.g., adoptive cell therapy, e.g., adoptive T cell therapy, is carried out by allogeneic transfer, in which the cells are isolated and/or otherwise prepared from a subject other than a subject who is to receive or who ultimately receives the cell therapy, e.g., a first subject. In such embodiments, the cells then are administered to a different subject, e.g., a second subject, of the same species. In some embodiments, the first and second subjects are genetically identical. In some embodiments, the first and second subjects are genetically similar. In some embodiments, the second subject expresses the same HLA class or supertype as the first subject.

In some embodiments, the subject, to whom the cells, cell populations, or compositions are administered is a primate, such as a human. In some embodiments, the primate is a monkey or an ape. The subject can be male or female and can be any suitable age, including infant, juvenile, adolescent, adult, and geriatric subjects. In some embodiments, the subject is a non-primate mammal, such as a rodent. In some examples, the patient or subject is a validated animal model for disease, adoptive cell therapy, and/or for assessing toxic outcomes such as cytokine release syndrome (CRS).

Additional Reagents

The methods and kits disclosed herein may comprise the use of one or more reagents. Examples of reagents include, but are not limited to, PCR reagents, ligation reagents, reverse transcription reagents, enzyme reagents, hybridization reagents, sample preparation reagents, affinity capture reagents, solid supports such as beads, and reagents for nucleic acid purification and/or isolation.

A solid support can comprise virtually any insoluble or solid material, and often a solid support composition is selected that is insoluble in water. For example, a solid support can comprise or consist essentially of silica gel, glass (e.g. controlled-pore glass (CPG)), nylon, Sephadex®, Sepharose®, cellulose, a metal surface (e.g. steel, gold, silver, aluminum, silicon and copper), a magnetic material, a plastic material (e.g., polyethylene, polypropylene, polyamide, polyester, polyvinylidene difluoride (PVDF)) and the like. Examples of beads for use according to the embodiments can include an affinity moiety that allows the bead to interact with a nucleic acid molecule. A solid phase (e.g. a bead) can comprise a member of a binding pair (e.g. avidin, streptavidin or derivative thereof). For instance, the bead may be a streptavidin-coated bead and a nucleic acid molecule for immobilization on the bead can include a biotin moiety. In some cases, each polynucleotide molecule can include two affinity moieties, such as biotin, to further stabilize the polynucleotide. Beads can include additional features for use in immobilizing nucleic acids or that can be used in a downstream screening or selection processes. For example, the bead may include a binding moiety, a fluorescent label or a fluorescent quencher. In some cases, the bead can be magnetic. In some instances, the solid support is a bead. Examples of beads include, but are not limited to, streptavidin beads, agarose beads, magnetic beads, Dynabeads®, MACS® microbeads, antibody conjugated beads (e.g., anti-immunoglobulin microbead), protein A conjugated beads, protein G conjugated beads, protein A/G conjugated beads, protein L conjugated beads, polynucleotide-dT conjugated beads, silica beads, silica-like beads, anti-biotin microbead, anti-fluoro chrome microbead, and BcMag™ Carboxy-Terminated Magnetic Beads. Beads or particles may be swellable (e.g., polymeric beads such as Wang resin) or non-swellable (e.g., CPG). In some embodiments a solid phase is substantially hydrophilic. In some embodiments a solid phase (e.g. a bead) is substantially hydrophobic. In some embodiments a solid phase comprises a member of a binding pair (e.g. avidin, streptavidin or derivative thereof) and is substantially hydrophobic or substantially hydrophilic. In some embodiments, a solid phase comprises a member of a binding pair (e.g. avidin, streptavidin or derivative thereof) and has a binding capacity greater than about 1350 picomoles of free capture agent (e.g. free biotin) per mg solid support. In some embodiments the binding capacity of solid phase comprising a member of a binding pair is greater than 800, 900, 1000, 1100, 1200, 1250, 1300, 1350, 1400, 1450, 1500, 1600, 1800, 2000 picomoles of free capture agent per mg solid support. Other examples of beads that are suitable for the invention are gold colloids or beads such as polystyrene beads or silica beads. Substantially any bead radii may be used. Examples of beads may include beads having a radius ranging from 150 nanometers to 10 microns. Other sizes may also be used.

The methods and kits disclosed herein may comprise the use of one or more buffers. Examples of buffers include, but are not limited to, wash buffers, ligation buffers, hybridization buffers, amplification buffers, and reverse transcription buffers. In some embodiments, the hybridization buffer is a commercially available buffer, such as TMAC Hyb solution, SSPE hybridization solution, and ECONO™ hybridization buffer. The buffers disclosed herein may comprise one or more detergents.

The methods and kits disclosed herein may comprise the use of one or more carriers. Carriers may enhance or improve the efficiency of one or more reactions disclosed herein (e.g., ligation reaction, reverse transcription, amplification, hybridization). Carriers may decrease or prevent non-specific loss of the molecules or any products thereof (e.g., a polynucleotide and/or amplicon). For example, the carrier may decrease non-specific loss of a polynucleotide through absorption to surfaces. The carrier may decrease the affinity of a polynucleotide to a surface or substrate (e.g., container, Eppendorf tube, pipet tip). Alternatively, the carrier may increase the affinity of a polynucleotide to a surface or substrate (e.g., bead, array, glass, slide, chip). Carriers may protect the polynucleotide from degradation. For example, carriers may protect an RNA molecule from ribonucleases. Alternatively, carriers may protect a DNA molecule from a DNase. Examples of carriers include, but are not limited to, polynucleotides such as DNA and/or RNA, or polypeptides. Examples of DNA carriers include plasmids, vectors, polyadenylated DNA, and DNA polynucleotides. Examples of RNA carriers include polyadenylated RNA, phage RNA, phage MS2 RNA, *E. coli* RNA, yeast RNA, yeast tRNA, mammalian RNA, mammalian tRNA, short polyadenylated synthetic ribonucleotides and RNA polynucleotides. The RNA carrier may be a polyadenylated RNA. Alternatively, the RNA carrier may be a non-polyadenylated RNA. In some embodiments, the carrier is from a bacteria, yeast, or virus. For example, the carrier may be a polynucleotide or a polypeptide derived from a bacteria, yeast or virus. For example, the carrier is a protein from *Bacillus subtilis*. In another example, the carrier is a polynucleotide from *Escherichia coli*. Alternatively, the carrier is a polynucleotide or peptide from a mammal (e.g., human, mouse, goat, rat, cow, sheep, pig, dog, or rabbit), avian, amphibian, or reptile.

The methods and kits disclosed herein may comprise the use of one or more control agents. Control agents may include control polynucleotides, inactive enzymes, non-specific competitors. Alternatively, the control agents comprise bright hybridization, bright probe controls, nucleic acid templates, spike-in controls, PCR amplification controls. The PCR amplification controls may be positive controls. In other instances, the PCR amplification controls are negative controls. The nucleic acid template controls may be of known concentrations. The control agents may comprise one or more labels.

Spike-in controls may be templates that are added to a reaction or sample. For example, a spike-in template may be added to an amplification reaction. The spike-in template may be added to the amplification reaction any time after the first amplification cycle. In some embodiments, the spike-in template is added to an amplification reaction after cycle number 2, 3, 4, 5, 6, 7, 8, 9, 10, 11, 12, 13, 14, 15, 20, 25, 30, 35, 40, 45, or 50. The spike-in template may be added to the amplification reaction any time before the last amplification cycle. The spike-in template may comprise one or more nucleotides or nucleic acid base pairs. The spike-in template may comprise DNA, RNA, or any combination thereof. The spike-in template may comprise one or more labels.

Disclosed herein are molecules, materials, compositions, and components that can be used for, can be used in conjunction with, can be used in preparation for, or are products of methods and compositions disclosed herein. It is understood that when combinations, subsets, interactions, groups, etc. of these materials are disclosed and while specific reference of each various individual and collective combinations and permutation of these molecules and compounds cannot be explicitly disclosed, each is specifically contemplated and described herein. For example, if a nucleotide or nucleic acid is disclosed and discussed and a number of modifications that can be made to a number of molecules including the nucleotide or nucleic acid are discussed, each and every combination and permutation of nucleotide or nucleic acid and the modifications that are possible are specifically contemplated unless specifically indicated to the contrary. This concept applies to all aspects of this application including, but not limited to, steps in methods of making and using the disclosed methods and compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

While some embodiments described herein have been shown and described herein, such embodiments are provided by way of example only. Numerous variations, changes, and substitutions will now occur to those skilled in the art without departing from the disclosure provided herein. It should be understood that various alternatives to the embodiments described herein can be employed in practicing the methods described herein.

Unless otherwise explained, all technical and scientific terms used herein have the same meaning as commonly understood by one of ordinary skill in the art to which this disclosure belongs. The following references contain embodiments of the methods and compositions that can be used herein: The Merck Manual of Diagnosis and Therapy, 18th Edition, published by Merck Research Laboratories, 2006 (ISBN 0-9119102); Benjamin Lewin, Genes IX, published by Jones & Bartlett Publishing, 2007 (ISBN-13: 9780763740634); Kendrew et al. (eds.), The Encyclopedia of Mol. Biology, published by Blackwell Science Ltd., 1994 (ISBN 0-632-02182-9); and Robert A. Meyers (ed.), Mol. Biology and Biotechnology: a Comprehensive Desk Reference, published by VCH Publishers, Inc., 1995 (ISBN 1-56081-569-8).

Standard procedures of the present disclosure are described, e.g., in Maniatis et al., Molecular Cloning: A Laboratory Manual, Cold Spring Harbor Laboratory Press, Cold Spring Harbor, N.Y., USA (1982); Sambrook et al., Molecular Cloning: A Laboratory Manual (2 ed.), Cold Spring Harbor Laboratory Press, Cold Spring Harbor, N.Y., USA (1989); Davis et al., Basic Methods in Molecular Biology, Elsevier Science Publishing, Inc., New York, USA (1986); or Methods in Enzymology: Guide to Molecular Cloning Techniques Vol. 152, S. L. Berger and A. R. Kimmerl (eds.), Academic Press Inc., San Diego, USA (1987)). Current Protocols in Molecular Biology (CPMB) (Fred M. Ausubel, et al. ed., John Wiley and Sons, Inc.), Current Protocols in Protein Science (CPPS) (John E. Coligan, et. al., ed., John Wiley and Sons, Inc.), Current Protocols in Immunology (CPI) (John E. Coligan, et. al., ed. John Wiley and Sons, Inc.), Current Protocols in Cell Biology (CPCB) (Juan S. Bonifacino et. al. ed., John Wiley and Sons, Inc.), Culture of Animal Cells: A Manual of Basic Technique by R. Ian Freshney, Publisher: Wiley-Liss; 5th edition (2005), and Animal Cell Culture Methods (Methods in Cell Biology, Vol. 57, Jennie P. Mather and David Barnes editors, Academic Press, 1st edition, 1998).

EXAMPLES

The following examples are included to further describe some aspects of the present disclosure, and should not be used to limit the scope of the invention.

Example 1—High-Throughput Identification of BCRs and TCRs

Tumor-infiltrating lymphocytes (TILs) are critical to anti-cancer immune responses, but are challenging to study due to their unpredictable abundance, phenotypes and function. A method for deep TIL characterization without the need for cell-sorting, stimulation or culture was developed by the inventors. The emulsion-based, single-cell barcoding method captures natively paired B-cell and T-cell receptor (BCR and TCR) sequences from lymphocytes among millions of input cells. In contrast to previous approaches the recovered variable regions are full-length and can be accompanied by additional mRNA and protein targets. The method was validated with 3 million B-cells from healthy human blood and 350,000 B-cells from an HIV patient before processing 400,000 unsorted cells from an ovarian adenocarcinoma, recovering paired BCRs and TCRs from over 11,000 TILs. Our results represent the deepest sampling of any paired BCR or TCR repertoire as well as the first demonstration of simultaneous RNA sequencing and protein measurements from single-cells in emulsion.

Example 2—Barcoding of Single Cells

Sequencing of the immune repertoire has wide applications in basic immunology, autoimmunity, infectious disease and oncology. While many studies have investigated BCR and TCR diversity in circulating blood, there is growing interest in the immune receptors of TILs, whose functions are highly relevant to cancer growth or regression yet variable and often uncharacterized. A critical step towards a better understanding of TILs will be recovery and functional characterization of their BCRs and TCRs, since this may allow the identification of new tumor-associated antigens. Tumor antigens are critically required to develop cancer vaccines, understand the role of checkpoint inhibitors, and advance chimeric antigen receptor T-cell (CAR-T) therapy in solid tumors. However, despite decades of technical progress in immune sequencing, no study has recovered full-length, natively paired BCRs (heavy and light chains) and TCRs (alpha and beta chains) from a heterogeneous sample such as a tumor without in vitro culture or cell sorting, steps that restrict and bias the observed repertoire. The technical challenge is particularly high since primary uncultured immune cells can contain 100-fold less receptor RNA than in vitro stimulated cells. To allow comprehensive analysis of natively paired BCRs and TCRs from complex heterogeneous samples a microfluidic emulsion-based method was developed for parallel isolation and DNA barcoding of large numbers of single cells (FIG. 4). Up to a million cells per hour are isolated in individual ~65 picoliter emulsion droplets. Within the droplets cells are lysed, target mRNA is reverse transcribed with target-specific primers and a two-step DNA barcoding process attaches both molecule-specific and droplet-specific barcodes to the cDNAs. After subsequent recovery and next generation sequencing, the dual barcoding strategy allows clustering of sequence reads into both their molecules and cells of origin. This allows extensive correction of errors and amplification biases, clone counting at both the mRNA and cellular levels, heavy chain isotype determination, and importantly, recovery of full-length, natively paired V(D)J sequences of BCR and TCRs simultaneously at extremely high throughput.

Figure 5A:
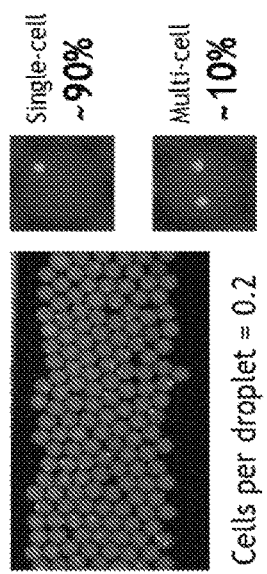
FIG. 5A is an exemplary depiction of droplets in which 3 million B-cells were passed into an emulsion at 0.2 cells/droplet resulting in ~90% of occupied cells containing single cells.

Example 3—Large Scale Recovery of B-Cell $V_H V_L$ Pairs from a Healthy Blood Sample The technology was initially developed and pairing capability and throughput was assessed with 3 million B-cells isolated by negative bead enrichment from peripheral blood of a healthy volunteer. The emulsion was split across six separate fractions which were processed in parallel and not remixed prior to sequencing. The emulsion was loaded at 0.2 cells per droplet, giving a Poisson expectation that ~90% of occupied droplets contain single cells, which was consistent with emulsion droplet observations (FIG. 5A). After emulsion breaking and additional library processing steps paired-end 325+300 bp sequencing was performed with Illumina MiSeq. To process the sequencing data, the droplet and molecular barcodes were used together to collect PCR replicate reads from each original mRNA molecule, and determined a consensus for each mRNA keeping only mRNA sequences built from at least two reads. Forward and reverse reads were stitched to generate full-length products comprising the 5' UTR, complete V(D)J sequence, and constant region sufficient for isotype determination. Rearranged immunoglobulin heavy and light chain sequences were annotated with IMGT High-VQuest and/or IgBLAST.

Figure 5C:
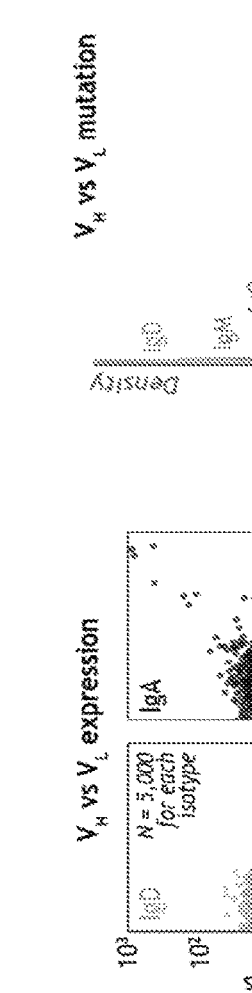
FIG. 5C is an exemplary graph of droplet barcode percentage vs. Ig isotype. Heavy chain isotype (most abundant isotype within each droplet) and light chain locus usage for 259,368 filtered $V_H V_L$ pairs are shown.
Figure 5D:
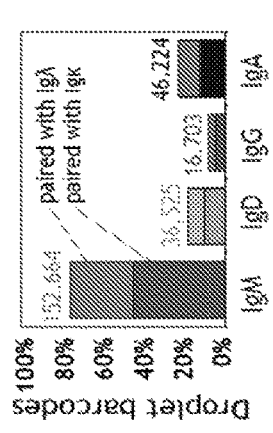
FIG. 5D is an exemplary graph of rank abundance of the 100 most frequent heavy chain clones in each of six independent emulsion fractions. 0.05% overall frequency is marked.
Figure 5B:
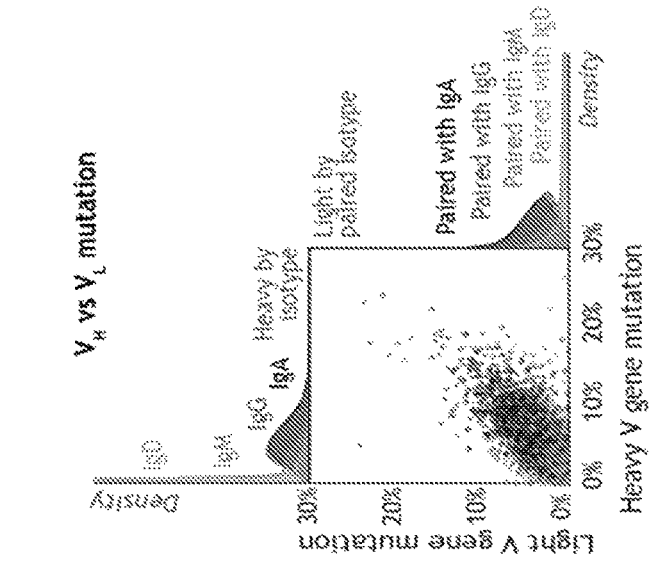
FIG. 5B is an exemplary depiction of $V_H V_L$ pairing precision. After emulsion barcoding and sequencing, data was enriched for data from single-cell droplets and $V_H V_L$ pairing precision was estimated using pair consistency among expanded clones.

The resulting dataset contained 324,988 droplet barcodes that were associated with at least one heavy chain ($V_H$) and one light chain ($V_L$) mRNA, with 229,869 distinct $V_H$ clonal lineages present as estimated by heavy chain clustering analysis. Since this raw set includes data from multi-cell as well as single-cell droplets, data from single-cell droplets was enriched by filtering out droplet barcodes linked to non-unanimous heavy or light chain V(D)J sequences (FIG. 5B). This step is made possible by the high diversity of typical immune repertoires, in which $V_H$ or $V_L$ mRNAs from two random cells will almost never match. The resulting enriched dataset comprised 259,368 $V_H V_L$ droplet barcodes and contained 182,745 $V_H$ clonal lineages, representing comfortably the deepest sampling of a paired immune repertoire to date. Precision of the $V_H V_L$ pairings by identifying incidences of clonal expansion was directly estimated, since clonally related cells should show consistency in their $V_H V_L$ pairings. 2,604 $V_H$ clones were identified that were observed in more than one emulsion fraction with high confidence to be clonally expanded cells. The consistency of $V_L$ sequences paired with these $V_H$ clones across fractions was very high and indicated a pairing precision of 96.1%, allowing high confidence in the entire filtered dataset of 259,368 $V_H V_L$ pairs. The cross-fraction $V_H$ and $V_L$ sequences were invariably associated with different droplet and molecular barcodes in each fraction and thus did not represent library cross-contamination. The analysis may underestimate pairing precision since some B-cells are known to express multiple light chains. 75.0% of the 259,368 filtered $V_H V_L$ droplet barcodes or "$V_H V_L$ pairs" contained IgM and/or IgD (FIG. 5C), which were frequently observed together as expected given the typical IgM⁺IgD⁺ phenotype of naive B-cells. Lower but substantial fractions of IgA (18.3%) and IgG (6.6%) $V_H V_L$ pairs were also found. All $V_H$ isotypes were paired with either Igκ or Igλ in a ~3:2 ratio. Among the 182,745 $V_H$ clonal lineages clone expansion was assessed in two ways: the number of droplet barcodes associated with a clone and observation of the clone across emulsion fractions. Clones seen in multiple droplet barcodes could reflect clonal expansion or multi-barcode droplets, which are expected in ~37% of droplets given the initial $\lambda=1$ Poisson dispersal of barcodes into droplets. However, any clone represented by >8 droplet barcodes is likely to be genuinely expanded (Poisson probability in a single droplet <10-6). While overall 6.0% of clones were seen in more than one fraction, for the clones seen in more than 8 droplet barcodes (0.7% overall), 99% of them were seen in more than one fraction. The 100 most frequent clones (30-137 droplet barcodes each, FIG. 5D) were all seen in at least five of six fractions. A combination of barcode counting and independent fraction analysis thus allows detection of rare expanded lineages amongst a vast background of non-expanded clones. Notably however, even the most abundant expanded clone was present at less than one cell in a thousand, exemplifying the huge diversity of human peripheral immune repertoires.

Figure 5E:
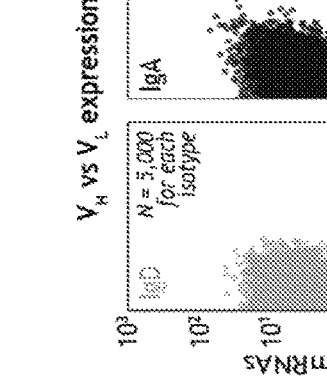
FIG. 5E is an exemplary graph of $V_H$ vs $V_L$ expression within cells as estimated by number of captured mRNAs within each droplet barcode. 5,000 points are shown for each isotype.

The number of captured mRNAs of each $V_H$ and $V_L$ chain within pairs as an estimate of expression level (FIG. 5E). Generally less than ten heavy chain (mean 2.0) and light chain (mean 4.0) mRNAs were captured per droplet barcode, a small population of droplet barcodes with dozens to hundreds of captured heavy and light chain mRNAs per cell was observed, almost exclusively from IgG and IgA expressing cells. Interestingly the degree of $V_H$ and $V_L$ mutation within pairs was strongly correlated both within each isotype (e.g. $V_H$ vs $V_L$ for IgG) and between isotypes (e.g. IgG vs IgM) (FIG. 2F). Furthermore, IgG and IgA pairs were almost all substantially mutated in both their $V_H$ and $V_L$ chains, whereas IgM and IgD pairs mostly showed little $V_H$ or $V_L$ mutation. These results are consistent with the mechanism of B-cell activation leading to class-switching from IgM and IgD to IgG or IgA, increased immunoglobulin expression and somatic hypermutation that affects both heavy and light chain loci in the cell. In addition to this observation that highly mutated $V_H$ chains tend to be paired with highly mutated $V_L$ chains, this method is capable of generating large numbers of full-length, natively paired BCRs from resting human B-cell repertoires.

Figure 3:
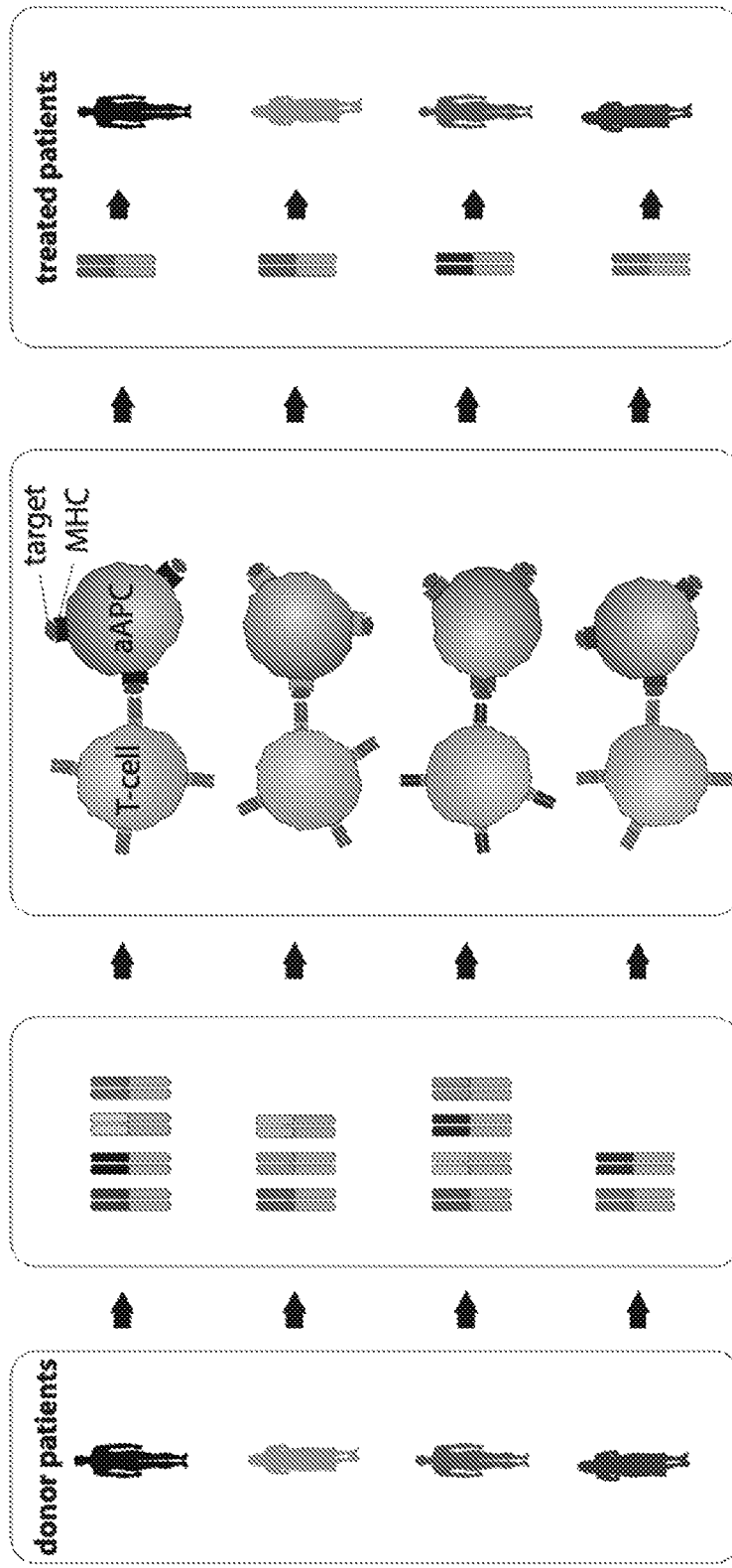
FIG. 3 depicts an exemplary flow chart for a method of discovery of human-derived, antigen-specific TCRs.
Figure 4A:
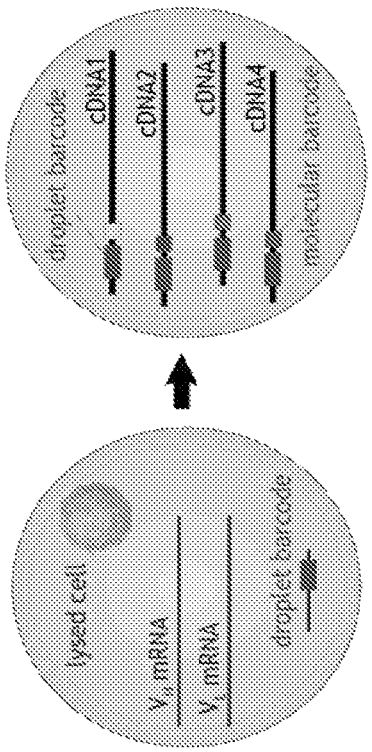
FIG. 4A is an exemplary depiction of two aqueous streams containing cells and lysis/reaction (LR) mix being passed into oil that produces monodisperse emulsion at over 8 million droplets per hour.
Figure 4B:
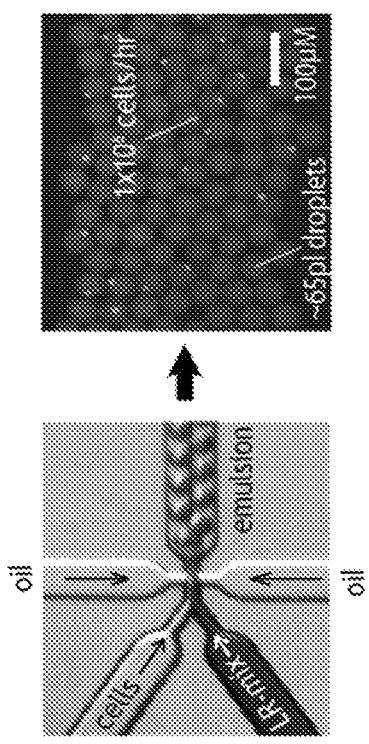
FIG. 4B is an exemplary depiction showing that cells within the vessels are lysed and subjected to molecular- and droplet-specific barcoding in a single reaction.
Figure 4C:
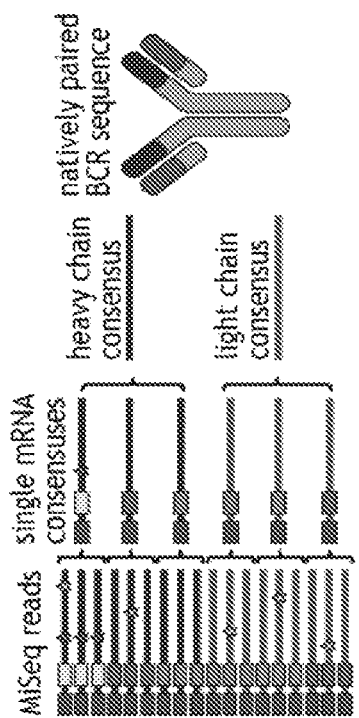
FIG. 4C is an exemplary depiction showing that target mRNA is reverse transcribed and template switch-tagged with a universal adaptor sequence. Subsequently PCR amplification occurs of a droplet barcode template initially diluted to ~1 molecule per droplet. Amplified barcodes are appended to template-switched cDNAs by complementary overlap extension. Products are recovered from the emulsion and purified using a biotin on the RT primer, before additional library processing steps and high throughput sequencing.
Figure 4D:
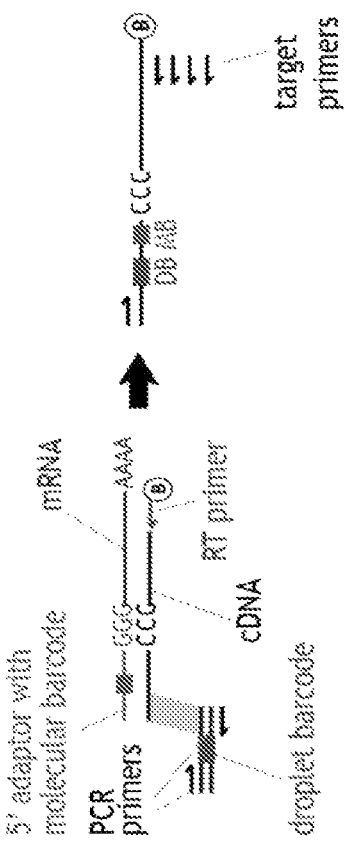
FIG. 4D is an exemplary depiction showing that dual barcoding allows clustering of sequencing reads into their molecules and droplets of origin, reconstructing the native receptor chain pairings while minimizing sequencing errors and amplification biases.

Example 4—Recovery of Known Low Frequency $V_H V_L$ Pairs from an HIV Elite Controller As a further validation of the pairing sensitivity and accuracy of the assay, a sample was processed where several rare (<1 cell in 10,000) native $V_H V_L$ pairings are already and publically known. Peripheral B-cells from an HIV elite controller patient were obtained whose memory B cells have been mined heavily in recent years for antibodies displaying HIV neutralization activity. 350,000 B-cells were processed to generate a total of 38,620 filtered $V_H V_L$ pairs. Interestingly, this individual showed a greater proportion of IgG than the previous healthy sample (FIG. 3A) or typical healthy peripheral B-cell repertoires. $V_H$ sequences from this dataset were compared to all reported broadly neutralizing antibodies (bNAbs) from this individual including PGT121 and found eight close or identical $V_H$ sequences, indicating that this family of bNAbs represents less than 0.03% of circulating B-cells. Crucially, all light chains paired to these heavy chains were of the expected and similarly rare bNAb lineage, displaying the same Igλ-V3-21/J3 rearrangement and hallmark triple codon insertion as previously reported, supporting the high accuracy and sensitivity of our method. Furthermore, on a phylogenetic tree of all known and newly generated PGT121-like $V_H V_L$ pairs from this individual (FIG. 3B), the $V_H$ and $V_L$ trees show strikingly similar topology with paired $V_H$ and $V_L$ sequences occupying mirror-like positions, likely reflecting shared phylogenetic history. The variant pairs discovered here fit well with this rule. Interestingly, two published antibodies PGT122 and PGT123 appear as exceptions; support for these two pairings was not found, but instead PGT122$V_H$:PGT123$V_L$-like, and PGT123$V_H$:PGT122$V_L$-like pairs were found, addressing the unverified pairing in the original report. DNA encoding the complete V(D)J regions of 8 novel PGT-like $V_H V_L$ pairs were synthesized, expressed the antibodies as full IgG and tested their ability to neutralize multiple pseudostrains of HIV (FIG. 6C). The antibodies expressed well and all showed strong neutralizing activity against the virus, demonstrating the utility of our approach in rapidly generating natively paired functional antibody variants from a relevant biological sample.

Example 5—B-Cell and T-Cell Receptor Pairs from Tumor Infiltrating Lymphocytes

Having validated emulsion barcoding for high throughput recovery of paired receptors, immune receptors were recovered directly from a tumor. A protease-dissociated resected ovarian adenocarcinoma sample was taken and entered 400,000 unsorted cells into emulsion. CD3/CD19 staining of a separate aliquot of the sample suggested substantial numbers of infiltrating B (~5%) and T cells (~20%) among the material. Single cell dispersal in the emulsion was similar to purified cells albeit with some limited clumping visible, and extensive variation in cell size and shape within the droplets as expected given the cell type heterogeneity of the sample (FIG. 7A).

Primers targeting the constant regions of T-cell receptor alpha and beta chains together were used with the BCR primers used previously, and following sequencing and stringent filtering recovered thousands of droplet barcodes linked to BCR or TCR products. To assess single cell precision all possible combinations of the four target loci ($V_H$, $V_L$, Vα, Vβ) within droplet barcodes were counted (FIG. 7B).

The vast majority (97.9%) of droplet barcodes with more than one target chain contained biologically expected pairings of BCR $V_H^+V_L$ or TCR Vα$^+$Vβ with only 2.1% containing mixed BCR-TCR combinations. Since barcoding of products is unbiased with respect to target chain, this result allows a high degree of confidence in the resulting 6,056 BCR $V_H V_L$ and 5,217 TCR VαVβ pairs. The BCRs showed striking dominance of IgG (>80%) compared to other isotypes (FIG. 7C), although all were present (IgE<0.05% only). Kappa and lambda light chains were present in similar ratios to the peripheral blood datasets.

Figure 5F:
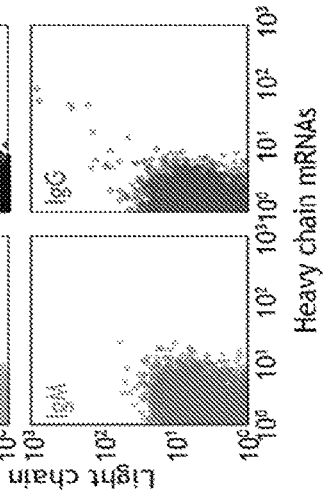
FIG. 5F is an exemplary graph of $V_H$ versus $V_L$ mutation correlation for BCR pairs and density distributions within each isotype.
Figure 5F:
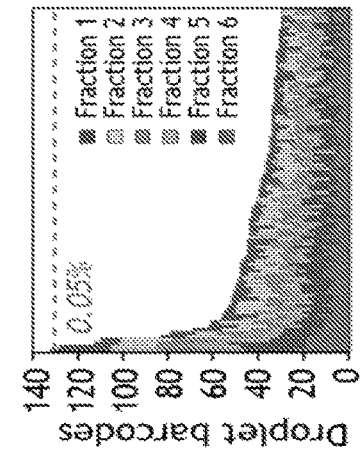

Similarly to peripheral blood a correlation was observed between BCR isotype and mutation level of both $V_H$ and $V_L$ chains, with IgG and IgA pairs showing greater $V_H$ and $V_L$ mutation than IgD and IgM, and a general correlation of mutation between $V_H$ and $V_L$ within each isotype (FIG. 7D). Interestingly, while IgD, IgM and IgA pairs showed very similar mutational distributions between the tumor and peripheral blood datasets (FIG. 5F), the tumor IgG fraction also contained a substantial proportion of little-to non-mutated sequences that was not observed in the peripheral blood. For TCRs, and for BCRs containing IgD, similar numbers of captured mRNAs were observed per droplet barcode to the BCR results from peripheral blood (FIG. 7E, mostly <10 per droplet barcode). In stark contrast, the tumor-derived IgM, IgA and IgG pairs showed a 10 to 100-fold increased average expression level with hundreds or thousands of target mRNAs captured in many of the droplet barcodes. The diversity of the captured TIL-TCR and BCR repertoires was then assessed (FIG. 7F). Among the 5,217 total TCR pairs 2,423 distinct TCR beta clones were observed. Seven clones were present at a frequency >1% with the top clone representing 16.9% of all droplet barcodes. Among the 6,056 total BCR pairs 1,518 distinct heavy chain clones were observed, with 15 clones at >1% frequency but none >5%. While this represents substantially more restricted diversity than the healthy peripheral BCR repertoire (where no clone was present in greater than 0.06% frequency), the presence of so many class-switched, mutated and highly expressed clones in the tumor sample demonstrates the necessity of a deep and sensitive sampling approach for TIL characterization. These method allows rapid retrieval of large numbers of TIL immune receptor pairs, from both B and T cells simultaneously, without the need for prior sorting or exogenous activation of defined TIL populations.

Example 6—Capture of Additional Phenotypic Markers of Interest

Figure 8A:
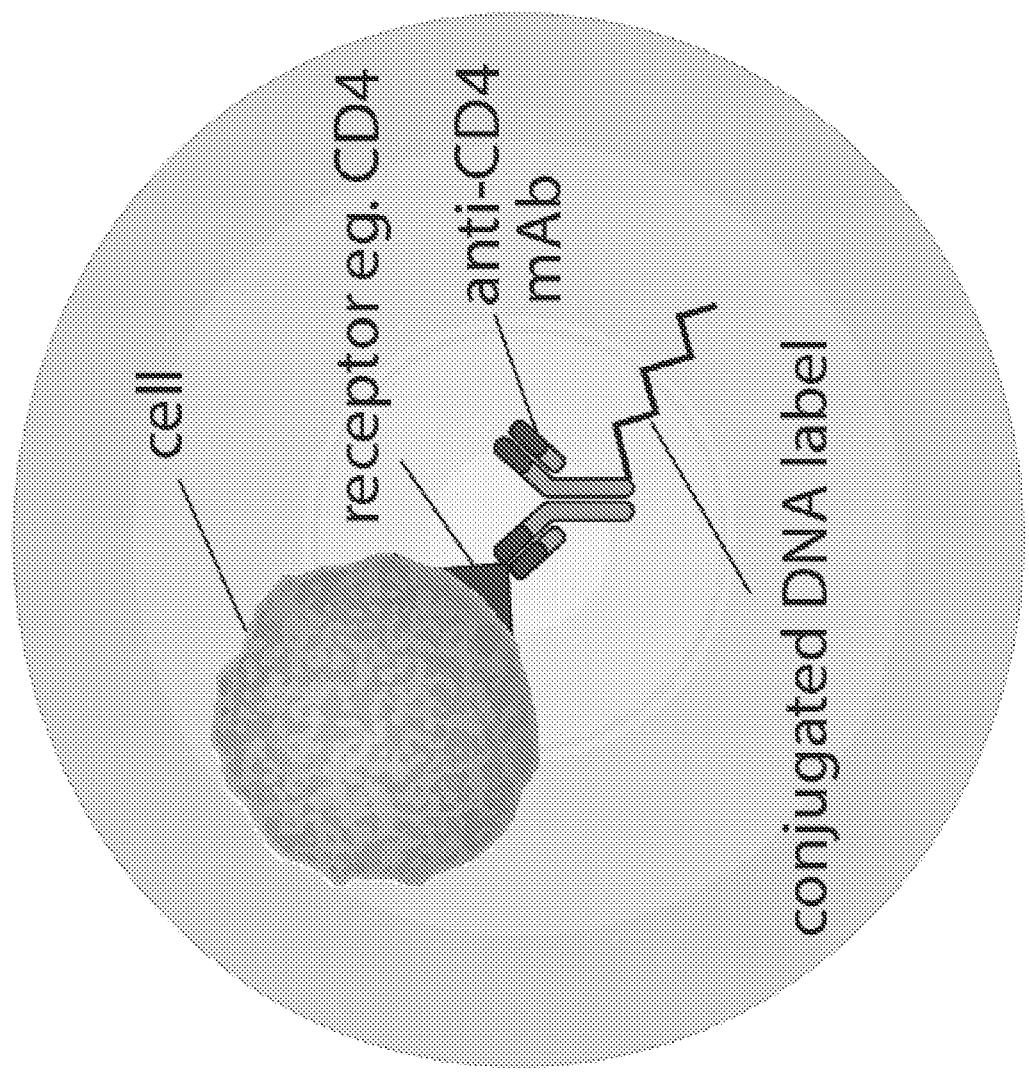
FIG. 8A depicts an exemplary co-capture of immune receptor sequences with additional mRNA and protein targets. Surface protein targets are quantified by pre-incubating cells with DNA-labeled staining antibodies prior to emulsion sequencing.
Figure 8B:
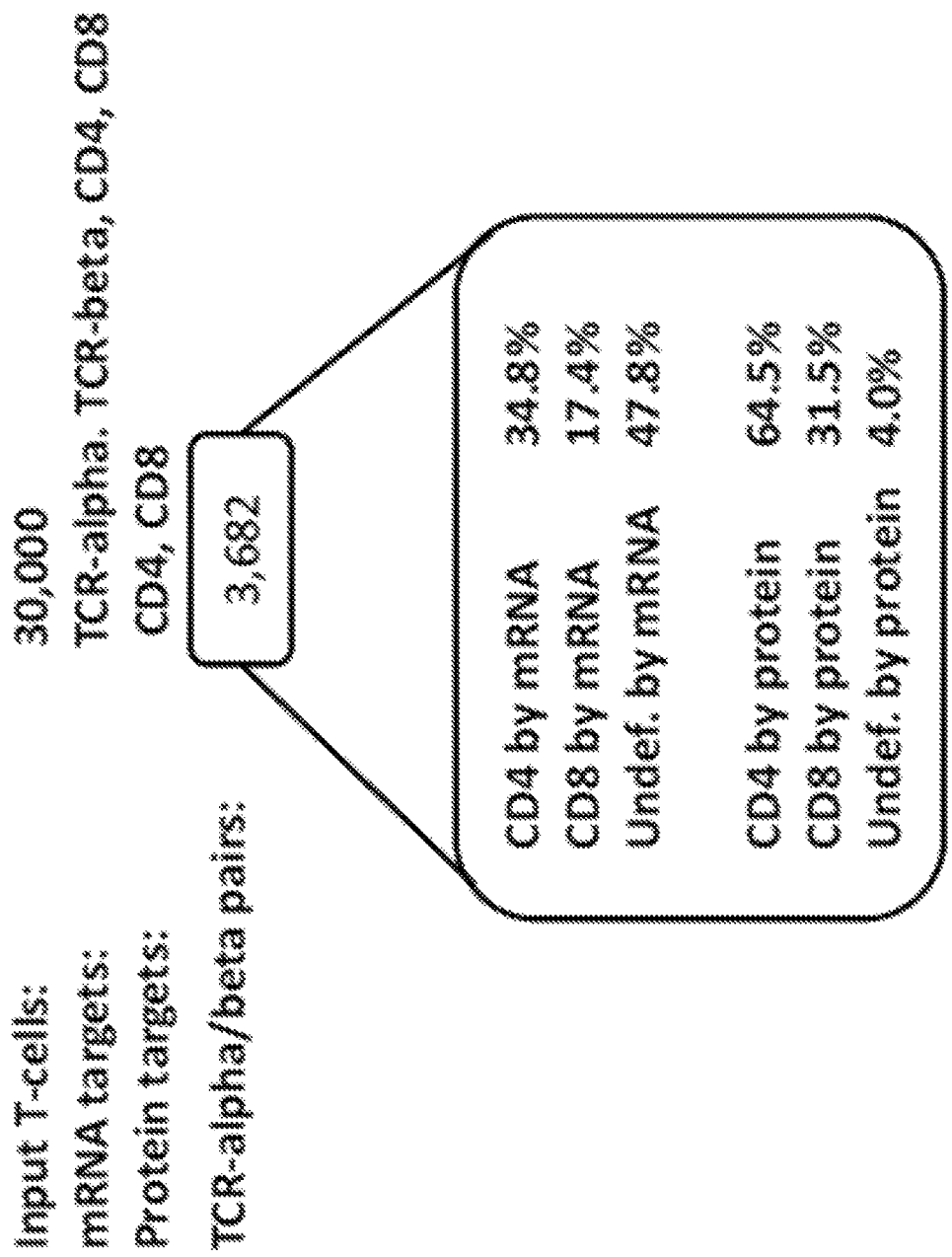
FIG. 8B depicts an exemplary CD4 and CD8 mRNA and protein measurements on 3,682 droplet barcode TCR $V_\alpha V_\beta$ pairs generated from healthy human T-cells.
Figure 8C:
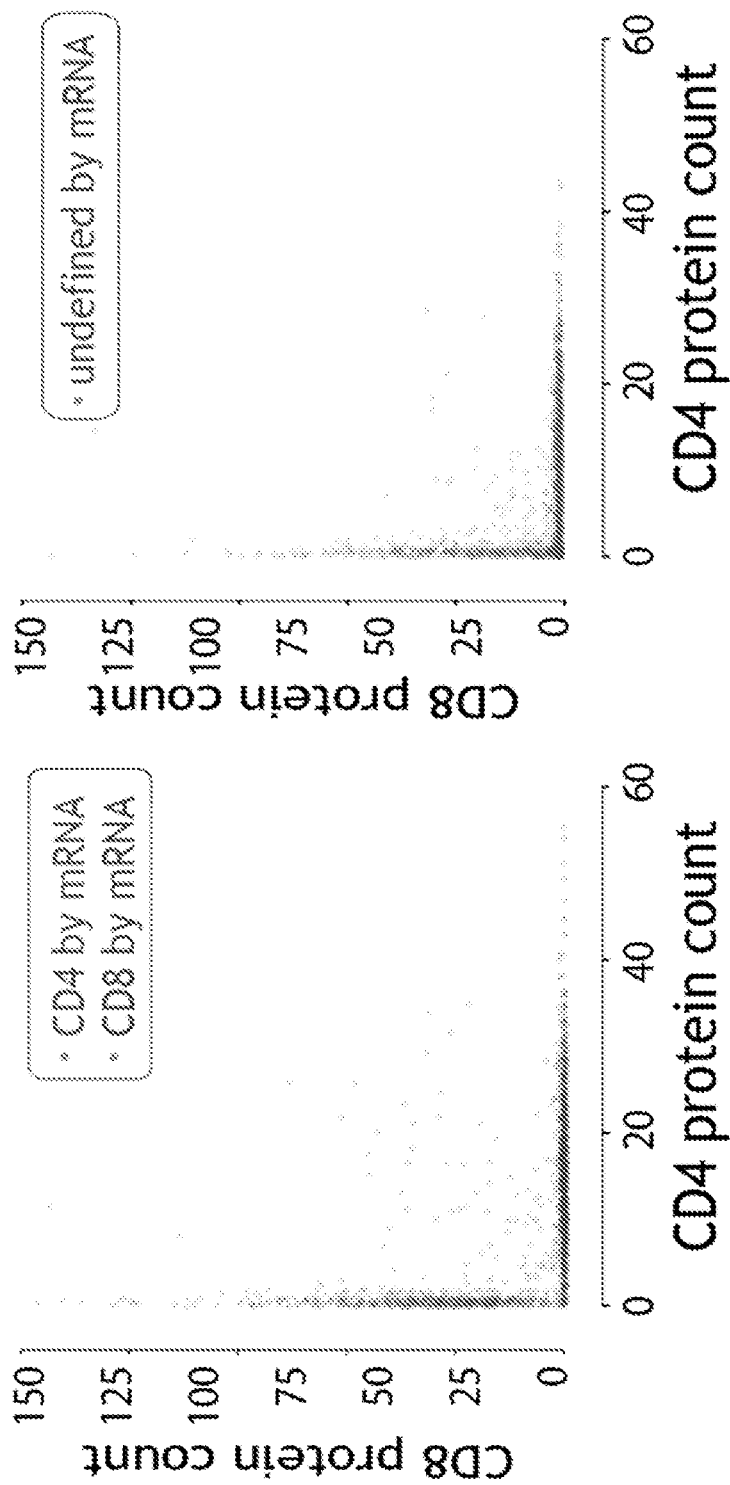
FIG. 8C depicts an exemplary Concordance between mRNA and protein measurements (each point is a droplet barcode linked to a TCR $V_\alpha V_\beta$ pair).
Figure 9A:
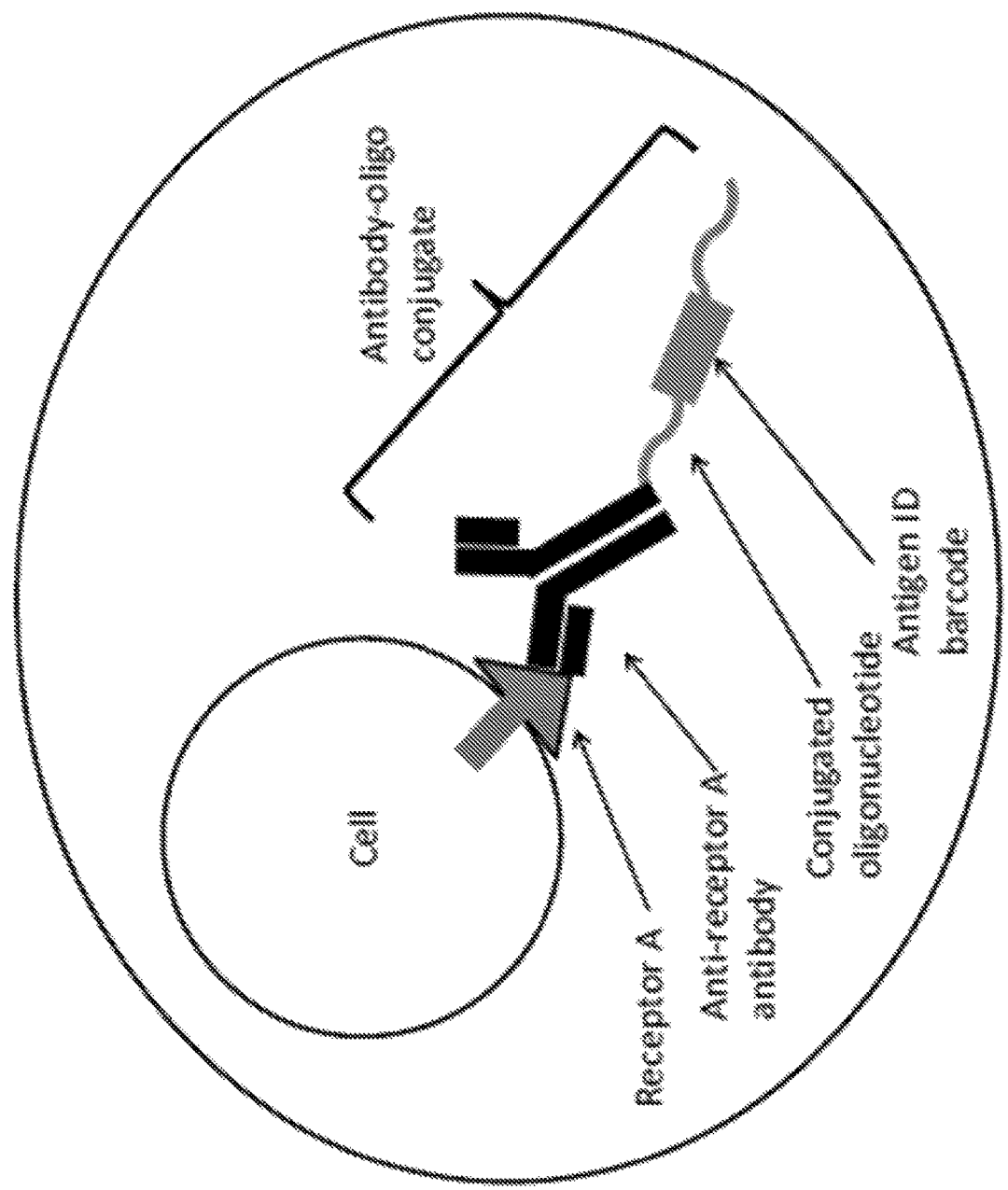
FIG. 9A depicts an exemplary schematic of a vessel of the methods described herein.
Figure 9B:
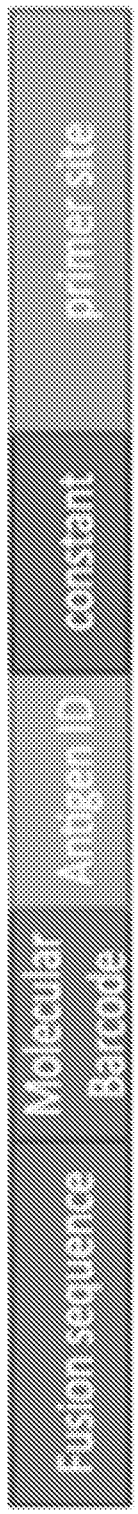
FIG. 9B depicts an exemplary design of oligonucleotide tag conjugated to an antibody. Each colored block represents a portion of the complete oligonucleotide sequence. The fusion sequence is used for enzymatic attachment of a droplet-specific DNA barcode inside the emulsion reaction. Only one possible arrangement of the sequences is shown, although other arrangements are compatible with the method described.
Figure 10A:
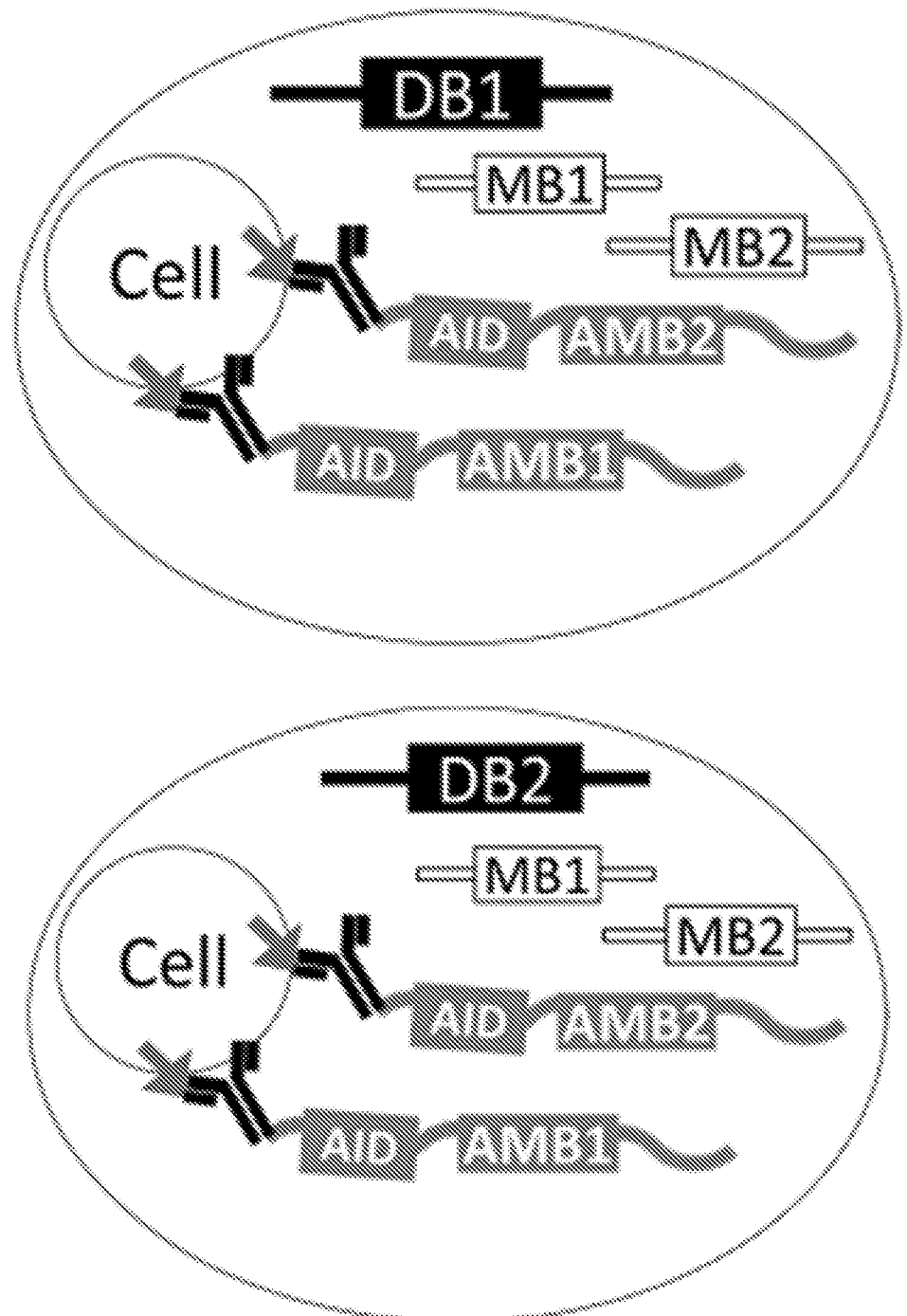
FIG. 10A depicts an exemplary schematic showing 2 vessels each containing a single cell bound to an antibody-oligonucleotide conjugate are depicted. (DB1—droplet barcode 1; DB2—droplet barcode 2; MB1—molecular barcode 1; MB2—molecular barcode 2; AID—antigen ID barcode; AMB1—antibody molecular barcode 1; AMB2—antibody molecular barcode 2).
Figure 10B:
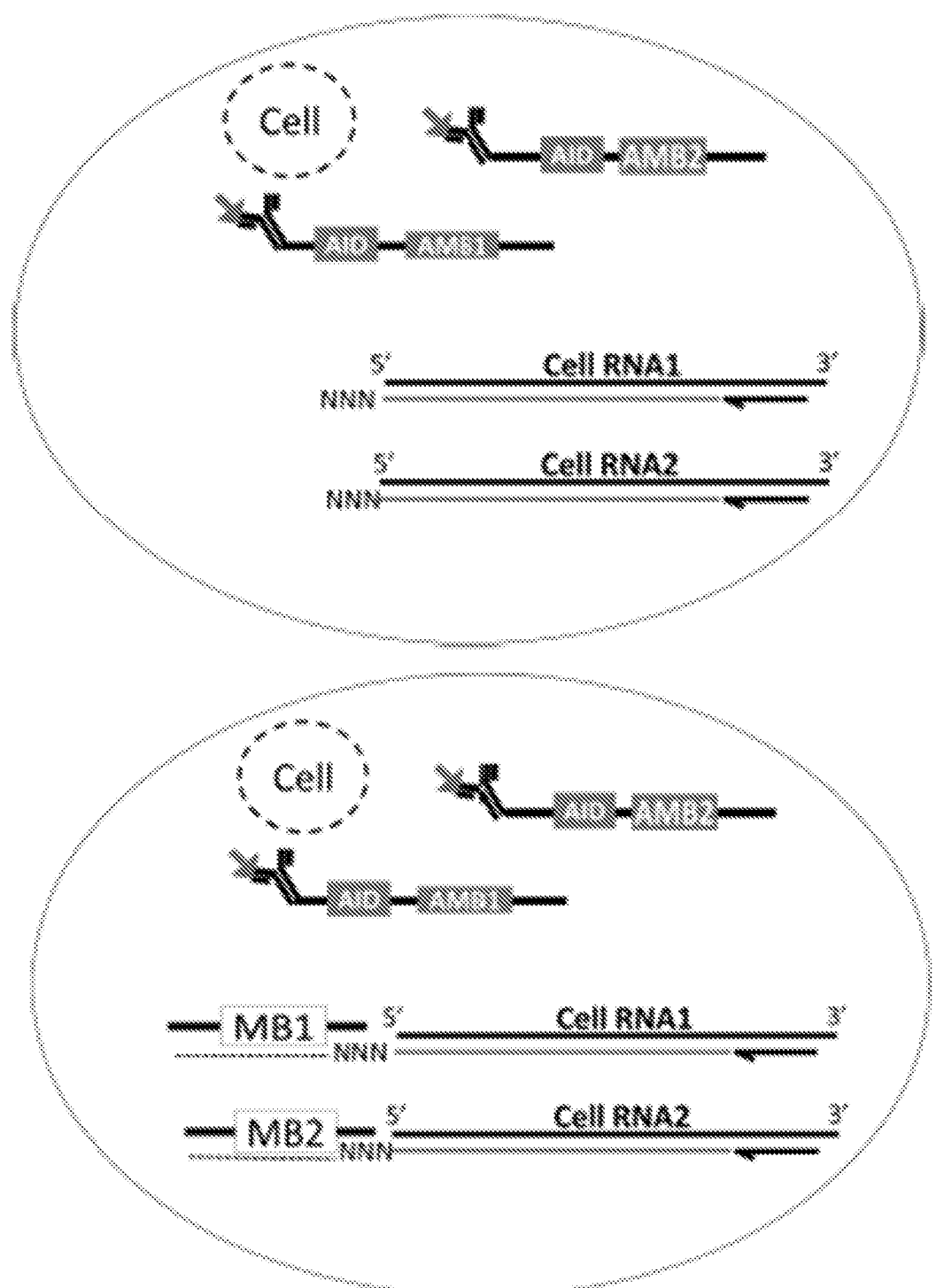
FIG. 10B depicts an exemplary schematic showing 2 vessels each containing RNA molecules from a lysed cell of a vessel from FIG. 9A. The RNA molecules are reverse transcribed and non-template nucleotides are added to the end of the cDNA molecule created by the reverse transcription. Molecular barcodes are hybridized to the non-template nucleotides added to the end of the cDNA molecule created by the reverse transcription.
Figure 10C:
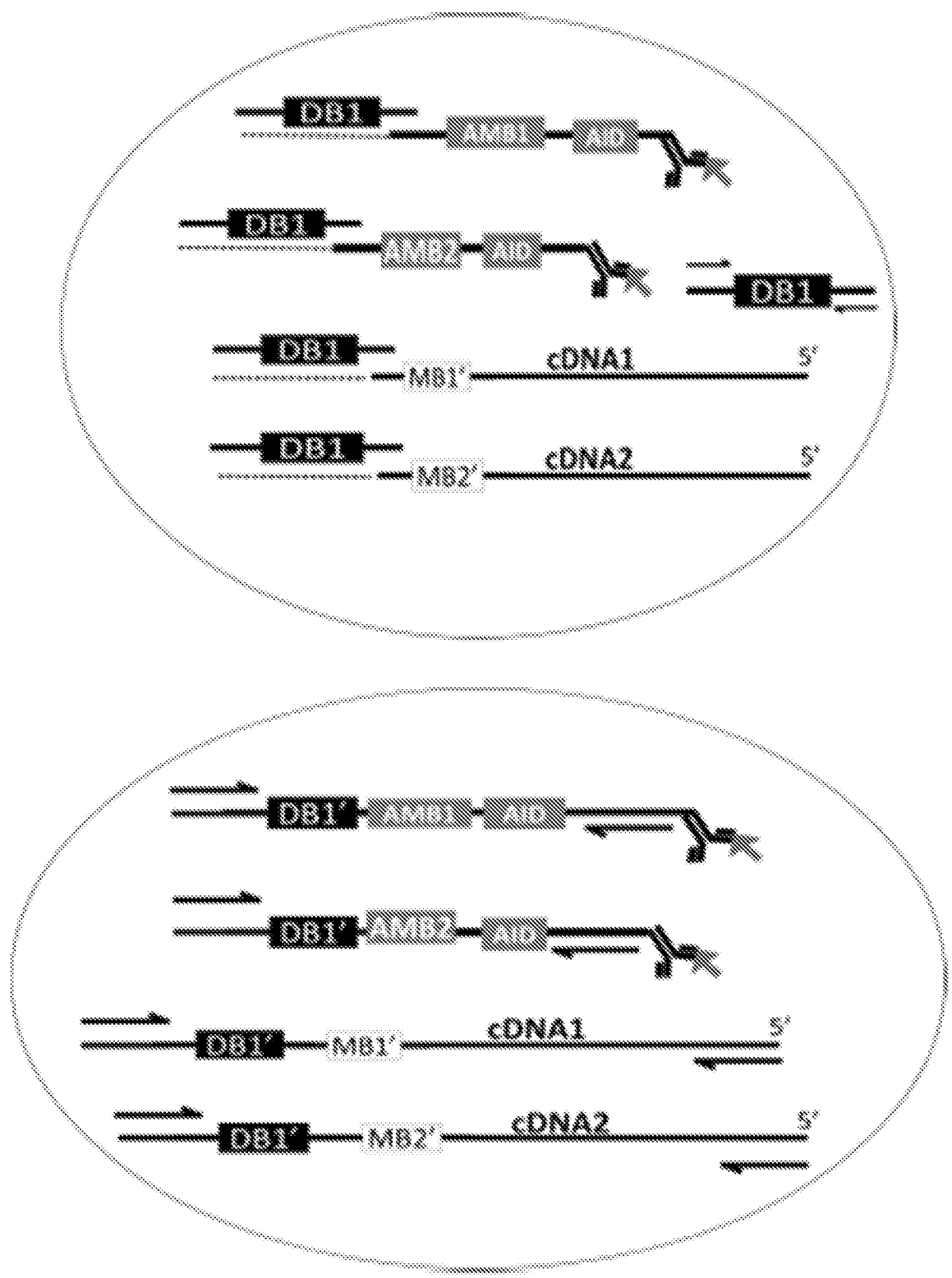
FIG. 10C depicts an exemplary schematic showing 2 vessels each containing a template barcoded polynucleotide that is amplified and attached to the cDNA of a vessel from FIG. 9B via hybridization and the cDNA is extended (top). The extended cDNA is then amplified (bottom).
Figure 10D:
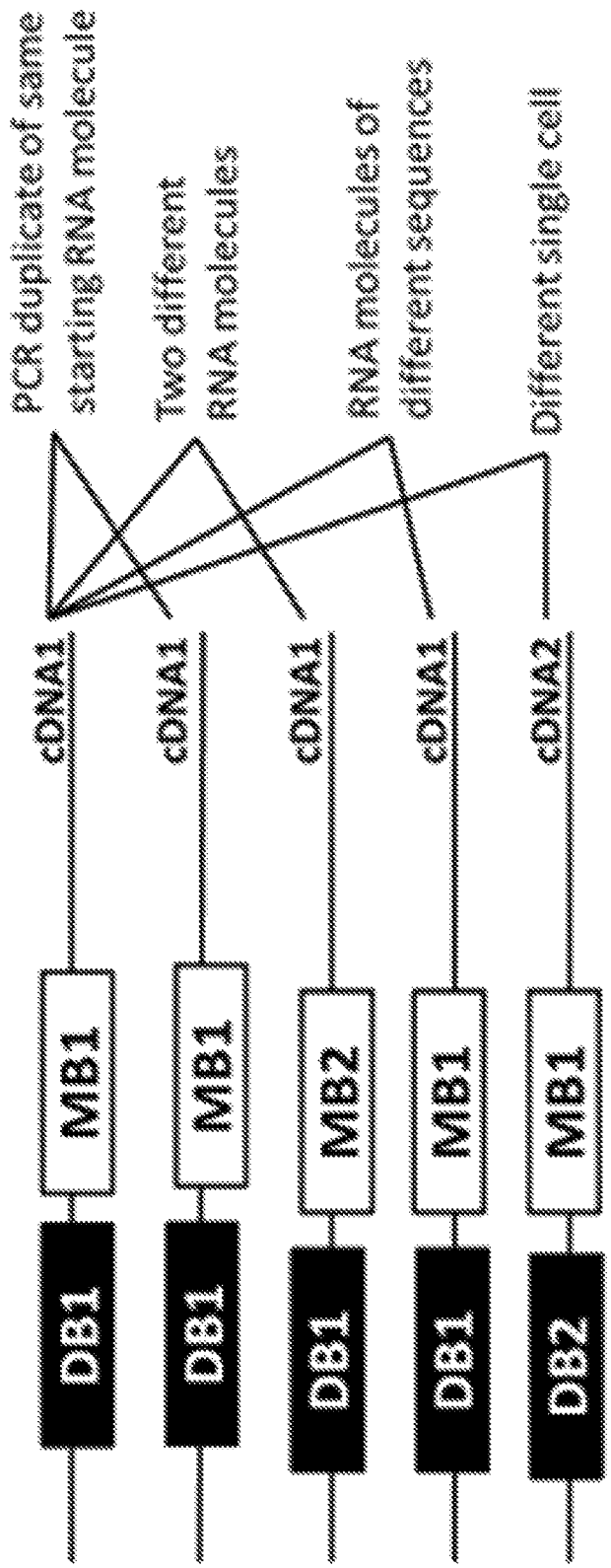
FIG. 10D depicts an exemplary schematic showing that RNA-MB-DB species with the same molecular barcode (MB) attached to the same identical RNA sequences is likely the result of PCR duplication. RNA-MB-DB species with two different MBs that are attached to the same identical RNA sequences (RNA1-MB1-DB and RNA1-MB2-DB) are two independent RNA molecules of origin and not of PCR duplication.
Figure 10E:
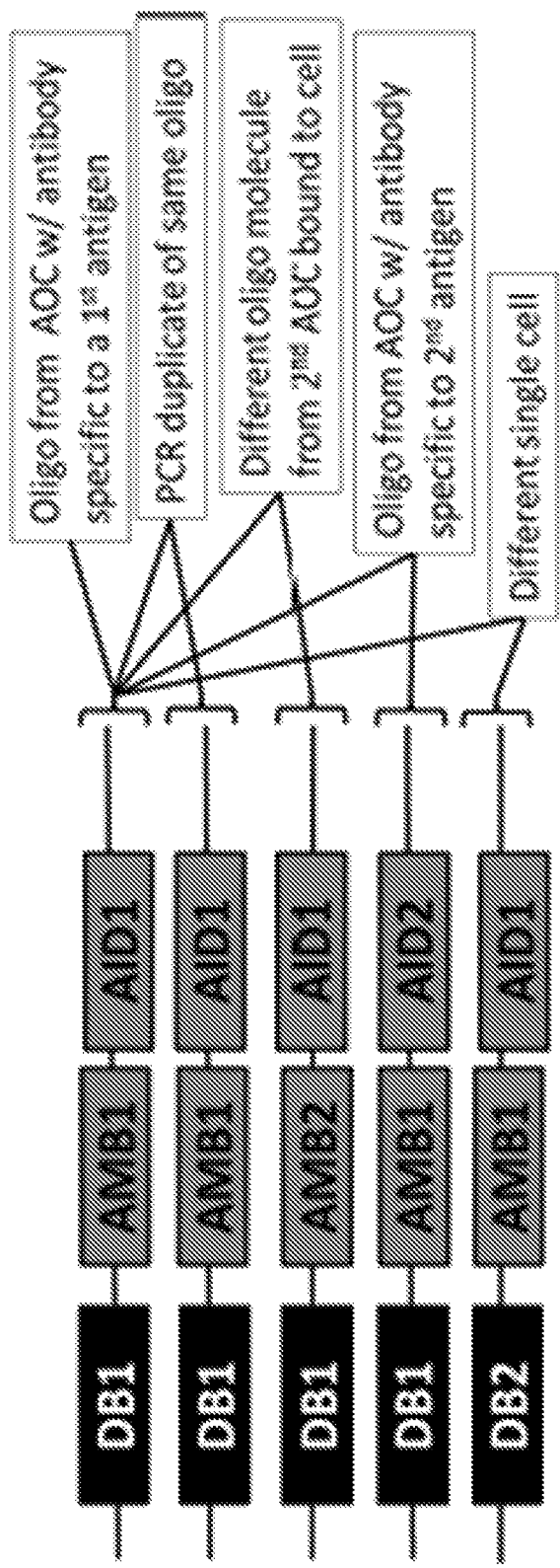
FIG. 10E depicts an exemplary schematic showing that DB-AMB-AID species with the same antibody molecular barcode (AMB) attached to a sequence with the same droplet barcode (DB) and antigen ID barcode (AID) is likely the result of PCR duplication. DB1-AMB1-AID1 and DB1-AMB2-AID1 species with two different AMBs attached to sequences with the same droplet barcode (DB) and antigen ID barcode (AID) are two independent oligonucleotide molecules from two independent antibody oligonucleotide conjugate molecules each with an antibody that specifically binds to the same target antigen attached to the same single cell in a vessel, and not of PCR duplication. DB1-AMBn-AID1 and DB1-AMBn-AID2 species with two different AIDs attached to sequences with the same droplet barcode (DB) and a same or different antibody molecular barcodes (AMBs) are two independent oligonucleotide molecules from two independent antibody oligonucleotide conjugate molecules attached to the same single cell in a vessel, wherein one of the antibody oligonucleotide conjugate molecules has an antibody that specifically binds to a first target antigen and the other antibody oligonucleotide conjugate molecule has an antibody that specifically binds to a second target antigen.

Pairing of receptor chains by droplet barcoding potentially allows capture of additional targets besides immune receptors. To investigate this possibility healthy T-cells into CD4$^+$ and CD8$^+$ populations were separated by magnetic bead enrichment and entered 20,000 cells of each type into separate emulsion runs, with primers targeting TCR alpha and beta chains and CD4 and CD8 mRNAs. After sequencing, 47.0% of 3,861 droplet barcodes containing TCR Vα and Vβ ("TCR pairs") from CD4$^+$ isolated cells were linked to CD4 mRNA, while only 0.3% were linked to CD8 mRNA. Conversely, 50.6% of 2,235 TCR pairs from CD8$^+$ isolated cells were associated with CD8 mRNA, while only 0.6% were linked to CD4 mRNA. This demonstrates the high specificity but limited sensitivity of an mRNA-based approach to cell phenotyping, similar to a previous report. In contrast, proteins such as cell surface receptors are usually present in far higher numbers (1,000-100,000 per cell) than their coding mRNAs, potentially making them easier to detect as well as being potentially more directly relevant to cell phenotype. To measure target protein levels on each cell custom oligonucleotide DNA labels were conjugated to anti-human CD4 and CD8 antibodies, and incubated the labeled antibodies with an unseparated mixture of CD4$^+$ and CD8$^+$ T-cells before entry of 30,000 cells into an emulsion (FIG. 8A). The DNA labels carry antibody-specific sequence tags as well as molecular barcodes and sequence complementarity to the amplified droplet barcodes, allowing emulsion droplet barcoding and molecular counting similarly to that done for mRNAs. The DNA labels were targeted as well as TCR, CD4 and CD8 mRNAs simultaneously. After sequencing and filtering 3,682 droplet barcodes were identified with high confidence TCR VαVβ pairs. Consistent with the previous experiment, roughly half (52%) of the TCR pairs could be assigned CD4 or CD8 status based on mRNA (FIG. 8B). However, over 95% of droplet barcodes could be assigned CD4 or CD8 based on protein status, with average molecular counts per droplet considerably higher for CD4/8 proteins (mean 20.5) than CD4/8 mRNAs (mean 1.0). Concordance between mRNA and protein signals was high (FIG. 8C): 96.0% of droplets given both mRNA and protein calls were in agreement. In some rare instances, both CD4 and CD8 proteins were detected, likely a result of droplets that contained two or more cells. Emulsion barcoding allows, for the first time, direct linking of single cell immune receptors to mRNA and protein markers of interest, all at high throughput. Application of this approach to TILs with an expanded, immune-oncology relevant marker set such as anti-PD-1 and anti-CTLA-4 is warranted.

Example 7—Human Samples

The blood sample for healthy repertoire validation was collected under the approval of the Personal Genome Project. PBMCs for the HIV bNAb experiment were obtained from donor 17, an HIV-1 infected donor from the IAVI Protocol G cohort. All human HIV samples were collected with written informed consent under clinical protocols approved by the Republic of Rwanda National Ethics Committee, the Emory University Institutional Review Board, the University of Zambia Research Ethics Committee, the Charing Cross Research Ethics Committee, the UVRI Science and Ethics Committee, the University of New South Wales Research Ethics Committee. St. Vincent's Hospital and Eastern Sydney Area Health Service, Kenyatta National Hospital Ethics and Research Committee, University of Cape Town Research Ethics Committee, the International Institutional Review Board, the Mahidol University Ethics Committee, the Walter Reed Army Institute of Research (WRAIR) Institutional Review Board, and the Ivory Coast Comite "National d'Ethique des Sciences de la Vie et de la Sante" (CNESVS). Cryopreserved, dissociated resected ovarian adenocarcinoma from a single donor was obtained from Conversant Biologics with written informed consent under an IRB approved protocol.

Example 8—Cell Preparation

For the study of 3 million healthy B-cells, 50 mL blood was drawn into Vacutainer CPT Cell Preparation Tubes with sodium heparin (BD), centrifuged for 20 min at 1800×g, washed twice in cell preparation buffer (lx PBS supplemented with 2% fetal bovine serum and 2 mM EDTA), using spins at 200×g to remove platelets, and the resulting PBMCs were cryopreserved in RPMI-1640 medium (Life Technologies)+20% fetal bovine serum+10% DMSO at −80° C. until needed. Prior to emulsion generation, PBMCs were thawed, washed twice in cell preparation buffer and counted. B-cells were isolated using a negative selection-based human B-cell enrichment kit (Stem Cell Technologies) according to the manufacturer's instructions. Cells were passed through a 20 µm cell strainer and diluted to $6.2 \times 10^6$ cells/mL (3-million B-cell experiment) or $3.1 \times 10^6$ cells/mL (PGT-donor and ovarian tumor experiments) in cell preparation buffer.

Example 9—Immune Receptor Barcoding in Emulsion

The emulsion generation platform consisted of three Mitos P-Pumps (Dolomite Microfluidics) driven by a single air compressor, each with a Mitos Flow Rate sensor, to allow computer-controlled flow of two aqueous phases and one fluorophilic oil continuous phase into a fluorophilically-coated quartz Dolomite Small 2-Reagent chip. One aqueous input channel contained the cells at the required density to produce the desired cells-per-droplet occupancy level, while the second aqueous channel contained lysis and reaction mix, consisting of AbPair™ reaction buffer and oligonucleotides (www.abvitro.com/catalog AV2070-1S and AV2080-1S), 5 units/µL MuMLV-based reverse transcriptase (Thermo Scientific) and 0.1 units/µL Herculase II PCR polymerase. A 100 µL Hamilton Microliter syringe was used to overload a 100 µL internal diameter PEEK tubing sample loop in two injections of ~100 µL each of LR mix. A 100 µL Hamilton Gastight syringe was used to load ~110 µL of the cell suspension into a ~100 µL, 0.2 mm internal diameter FEP tubing loop. The emulsion was formed by focused flow jetting of the aqueous phases at identical flow rates through the 2-reagent chip with simultaneous oil flow from the two oil channels in the chip. The emulsion leaving the chip exit channel was dripped into 0.2-mL PCR strip tubes (Eppendorf) on a cold block, after which excess oil was removed by pipetting from the bottom of the tube, 40 µL of overlay solution was added (25 mM Na-EDTA, pH 8.0) and tubes were transferred to a standard thermocycler for the transcript tagging reaction. During a 45-min reverse transcription (RT) step, RNA is reverse transcribed at 42° C. with target-specific RT primers, with template-switch-based addition of a universal adaptor sequence containing a randomized molecular barcode. Following RT, emulsions were subjected to 40 cycles of thermocycling (each cycle: 82° C. for 10 sec, 65° C. for 25 sec) to perform PCR amplification of the droplet barcode templates, which were diluted in the initial lysis and reaction mix to 30,000 cp/µL, generating a concentration in the final mixture of 15,000 cp/µL or ~1 per ~65 pl droplet. One end of the droplet barcode comprises the Illumina read 2 ("P7") primer site, whereas the other end matches the common sequence of the universal adaptor oligonucleotide. Therefore, during PCR, template-switched cDNAs can anneal to amplified droplet barcode strands and become spliced by overlap extension to produce full-length products containing target, molecular barcode and droplet barcode sequences.

Example 10—Emulsion Breaking, Cleanup, Downstream PCRs, Pooling and Sequencing

After thermocycling, the overlay solution was removed by pipetting and 40 µL emulsion breaking solution (1:1 FC-40:perfluorooctanol) were added together with 15 µL lysate clearing solution (12.5 µL Qiagen Protease, 2.5 µL 0.5 M Na-EDTA, pH 8.0). After inverting 10 times to break the emulsion, the mixture was incubated for 15 minutes at 50° C. and 3 minutes at 95° C. to inactivate the protease. After centrifugation at 15,000×g for 1 min to isolate the aqueous phase, the recovered material was rigorously purified to remove oligonucleotides, reagents and excess droplet barcode PCR products. Since full length products contain biotin due to 5' biotinylation of the RT primer, they can be efficiently separated from excess droplet barcode PCR products by cleanup on streptavidin beads, thus minimizing downstream PCR recombination artifacts, a common problem in extension-by-overlap approaches. First products were purified using AMPure XP beads (Agencourt) using manufacturer's instructions at a 1:1 ratio, followed by cleanup using streptavidin beads (New England Biolabs) also using manufacturer's instructions, followed by elution in deionized water at 95° C., followed by a second cleanup with AMPure XP beads at a 1:1 ratio. Products were then entered into a target enrichment PCR in which primers specific to the constant regions of the B- or T-cell receptor targets were used together with a primer specific to the universal end of the droplet barcode sequence. This reverse primer also contained a six-base index barcode for multiplexed sequencing on the MiSeq instrument according the manufacturer's instructions. Thus, only full-length, droplet-barcoded target sequences are amplified in this step. All targets were first amplified together for seven cycles of 98° C. 10 seconds; 64° C. 20 seconds; 72° C. 15 seconds, using Q5 Hot Start polymerase (New England Biolabs) under manufacturerrecommended conditions, including a 2 minute 98° C. polymerase activation step at the beginning of the reaction. This was followed by AMPure XP cleanup at a 1.5:1 beads:PCR ratio. A second seven-cycle targeting each chain ($V_H$, $V_L$, $V\alpha$, $V\beta$) separately was then performed, using the same thermocycling conditions as before, followed by AMPure XP cleanup. A final PCR with the same thermocycling conditions and 5-15 cycles (depending on yield as judged by qPCR) to add the full-length Illumina sequencing adaptors and generate enough material for TapeStation D1000 (Agilent) quantification was then performed. Libraries were then pooled and sequenced on the V3 2×300 bp MiSeq platform (Illumina).

Example 11—Modifications to the MiSeq Platform

Reconstruction of the complete variable V(D)J region of BCR or TCR requires stitching the two paired-end Illumina reads. To improve this process the forward read of the 2×300 bp kit was extended to 325 bp. 10% phiX spike-in was used to alleviate issues of limited library diversity, since immune receptor libraries have limited diversity in the constant region primer sites.

Example 12—Overview of Bioinformatics Processing of Reads

Illumina MiSeq reads were processed using custom pipelines built around the pRESTO package (version 0.4) to generate full length consensus sequences for mRNA molecules from each droplet, annotated with IgBLAST and/or IMGT/HighV-QUEST, and further aligned, filtered, and processed with custom scripts and the Change-O package to generate statistics.

Example 13—Read Processing and Annotation, Isotype Assignment

Raw read processing, V(D)J annotation and clonal assignment was performed with custom pipelines utilizing the pRESTO and Change-O packages. Briefly, raw Illumina paired-end 325+300 bp reads were quality-controlled, primer-trimmed, and droplet-specific (DB) and molecule-specific barcodes (MB) identified via fuzzy matching of primer sites. Together, DB and MB uniquely specify a molecule of origin, and this unique molecular identifier (UMI) was used to group agreeing PCR replicate reads (minimum of two) hailing from the same molecule to generate a consensus for each mRNA sequence. Isotype-specific priming was confirmed by fuzzy matching of known isotype-specific constant regions within primer-trimmed sequences. V(D)J germline segments and rearrangement structure was determined using IgBLAST and confirmed with IMGT/HighV-QUEST where appropriate, parsed by Change-O and custom scripts. Clones were assigned via single-linkage clustering within groups of functional V(D)J sequences having matching IGHV gene, IGHJ gene, and junction length as implemented in Change-O. For the 3 million circulating cell dataset, a weighted intraclonal distance of 4.0, using a symmetrized transition/transversion model was used as the nearest-neighbor distance cutoff within clones.

Example 14—Droplet Immune Receptor Inclusion Filtering and Pairing Fidelity Calculation Precision of B-cell sequence recovery from droplets can be assessed in two ways with this barcoding method: using intra-droplet mRNA sequence agreement, and via cross-fraction pairing agreement. Within each droplet, multiple mRNAs are captured per locus; expressed V(D)J sequences from one cell should agree. The presence of more than one productive VDJ and one productive VJ sequence per droplet is flagged bioinformatically as putative immune receptor inclusion or multi-cell occupancy, using a cutoff of 2% sequence diversity (mean pairwise nucleotide differences pi55<0.02) of multiple aligned V(D)J segments to define sequence agreement. Heavy and light chain consensus sequences were built for each allelically excluded droplet, and were used for clone definition and cross-fraction pairing analysis. For the 3 million circulating B-cell dataset, each $V_H$ lineage is associated with one (in the ideal case) of >20,000 light chain clones in the dataset. Among 259,368 immune-locus-excluded droplets with $V_H V_L$ pairs, 10,870 VDJ heavy locus rearrangement clusters were present in at least two of six physically separated emulsion fractions. These clusters represent either expanded lineages or independent but similar rearrangement of the same VJ exons. Where a VDJ rearrangement is paired with a consistent VJ rearrangement across two replicates, both experiments independently produced a true positive (33,157 of 35,922 possible pairwise comparisons for 2,604 clones with rarer rearrangements). Thus, the precision for each replicate is 96.1% (0.923^0.5).

Example 15—HIV bNAb Candidate Sequence Discovery

New natively paired broadly-neutralizing antibodies (BNAbs) to HIV were discovered by mining our 38,620 $V_H V_L$ pairs for similarity to known bNAb HCDR3s, VDJ sequences and Donor 17 lineages culled from the literature using tblastx, MUSCLE, and PhyML, followed by manual inspection of phylogenetic trees of full V(D)J amino acid sequence to select antibody candidates interspersing with known bNAb sequences.

Example 16—HIV bNAb Protein Expression and Purification

Antibody sequences were synthesized and cloned into previously described heavy and light chain vectors. Heavy and light chain plasmids were co-transfected (1:1 ratio) in 293 FreeStyle cells using 293fectin (Invitrogen) according to the manufacturer's protocol. Antibody supernatants were harvested four days following transfection and purified by protein-A affinity chromatography. Purified antibodies were buffer exchanged into PBS before use in further assays.

Example 17—Pseudovirus Production and Neutralization Assays

Pseudoviruses were generated by transfection of 293T cells with an HIV-1 Env expressing plasmid and an Env-deficient genomic backbone plasmid (pSG3ΔEnv). Pseudoviruses were harvested 72 hr post-transfection for use in neutralization assays. Neutralizing activity was assessed using a single round of replication pseudovirus assay and TZM-Bl target cells. Briefly, TZM-Bl cells were seeded in a 96 well flat bottom plate. To this plate was added pseudovirus, which was preincubated with serial dilutions of antibody for 1 hr at 37° C. Luciferase reporter gene expression was quantified 72 hr after infection upon lysis and addition of Bright-Glo Luciferase substrate (Promega). To determine $IC_{50}$ values, dose-response curves were fit by nonlinear regression.

Example 18—Ovarian Tumor Target Chain Identification

After simultaneous BCR and TCR capture from ovarian dissociated tumor tissue in emulsion, reads were filtered using molecular and droplet barcodes as previously described, but then looked for the presence of each of the four possible target chain types (BCR $V_H$, BCR $V_L$, TCR Vα, TCR Vβ). Target chains were retained if they were supported by at least two mRNAs, each with at least two sequencing reads. All droplet barcodes containing only BCR $V_H V_L$ or TCR VαVβ pairs were analyzed further. BCR heavy chain and TCR beta chain clones were called based on distinct CDR3 amino acid sequences.

Example 19—Protein Detection in Emulsion Through DNA-Labelled Antibody Staining

Single-stranded, 200 bp DNA oligonucleotides were designed to contain unique 5 bp antigen ID sequences and were modified with a 5' amino group (Integrated DNA Technologies). Mouse monoclonal, anti-human CD4 (BioLegend, #300516) and CD8a (BioLegend, #301018) antibodies were conjugated to DNA oligonucleotide tags using the Thunder-Link kit (Innova Biosciences) according to manufacturer's protocol. For cell labeling prior to emulsion, two million negatively selected T-cells from peripheral blood were diluted in 400 μL cell buffer+2 mM EDTA+ 0.05% sodium azide. Single stranded salmon sperm DNA was added to cells to a final concentration of 200 μg/mL and cells were rotated at room temperature for five minutes. A mixture of CD4 and CD8a DNA-labeled antibodies (each to a final concentration of 5 nM) was added to the cells and incubated at room temperature for 30 minutes. Cells were washed three times with cell Buffer+2 mM EDTA+0.05% sodium azide+200 μg/mL single stranded salmon sperm DNA. Cells were resuspended in cell buffer+0.05% sodium azide prior to entry into emulsion analysis. 30,000 cells were used for emulsion sequencing.

Example 20—Identifying TCR Antigen Targets

In some cases, natively paired TCR chains are cloned into an expression vector encoding for the TCR chains and a DNA construct encoding a reporter gene, such as luciferase or a fluorescent protein that is expressed upon activation by an APC. T lymphocyte cell lines, such as Jurkat cells, engineered to not express endogenous TCR chains are transfected with the expression vector encoding the paired TCR chain of interest. The CD4 or CD8 co-receptor is expressed by T lymphocyte cell line. TCRs are initially screened by incubation with syngeneic APCs or tumor cells, which are primary cells or an MHC-matched cell line. TCR reactivity is determined by the reporter gene or measurement of cytokines, such as IFNγ by ELISPOT, and a candidate TCR of interest is identified.

A candidate natively paired TCR chain of interest, in some cases a natively paired TCR chain of interest identified using an initial screen as described above, is cloned into an expression vector. T lymphocyte cells are transfected with expression vectors encoding for the TCR of interest. In some cases, the T lymphocyte cells may lack endogenous TCR expression. Separately, artificial antigen presenting cells (aAPCs) are generated by transfecting an APC cell line that does not express endogenous MHC receptors, such as the K562 cell line, with MHC genes matching the organism from which the TCR chain is derived. aAPCs are also engineered with a reporter gene, such as luciferase or a fluorescent protein. A library of antigen-expressing vectors is transfected into antigen presenting cells. The sequence coding for the antigen can be the exact sequence of peptides of interest, a minigene construct or an entire cDNA coding sequence. Alternatively, APCs are directly pulsed with a library of peptides of interest.

T cells expressing the natively paired TCR chain of interest are co-cultured with aAPCs presenting a library of antigens. Engagement of T lymphocytes with aAPCs via binding of TCRs to MHC-peptide complexes results in activation of the T cells and activation of aAPC reporters. For example, TCR binding to an MHC-peptide complex leads to aAPCs expression of luciferase or a fluorescent protein. Activated aAPCs are isolated by sorting techniques, such as fluorescence activated cell sorting (FACS). Peptides are dissociated from MHC proteins by standard techniques such as treatment with a mild acid and reverse phase-HPLC (RP-HPLC). Mass spectrometry or sequence is performed to identify the antigen target of the natively paired TCR chain.

While preferred embodiments of the present invention have been shown and described herein, it will be apparent to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for determining a target antigen of a T-cell receptor (TCR) polypeptide comprising:
   (a) contacting one or more engineered cells to a plurality of antigen presenting cells (APCs) wherein the one or more engineered cells express a TCR polypeptide comprising at least one pair of natively paired TCR chains of a single immune cell from a subject, wherein the plurality of APCs presents different antigen polypeptides;
   (b) determining an antigen polypeptide presented by a selected APC of the plurality of APCs; and
   (c) determining the target antigen of the natively paired TCR chains, wherein the determined target antigen is the determined antigen polypeptide presented by the selected APC of the plurality of APCs.

2. The method of claim 1, further comprising, before (a):
   (a') expressing a TCR polypeptide in one or more engineered cells, wherein the TCR polypeptide comprises at least one pair of the natively paired TCR chains.

3. The method of claim 2, further comprising, before (a'):
   (a'') identifying a plurality of natively paired TCR chains from a biological sample from a subject using high-throughput parallel single-cell sequencing.

4. The method of claim 1, wherein the plurality of APCs of (a) are engineered APCs.

5. The method of claim 4, wherein the selected engineered APC of (b) is a reactive engineered APC that has reactivity to the engineered cell expressing the TCR polypeptide.

6. The method of claim 4, wherein the selected engineered APC of (b) is an activating engineered APC that activates the engineered cell expressing the TCR polypeptide.

7. The method of claim 5, further comprising, after (a):
   (b') assaying for reactivity of an APC of the plurality of APCs to an engineered cell of the one or more engineered cells expressing a TCR polypeptide.

8. The method of claim 6, further comprising, after (a):
   (b'') assaying for activation of an APC of the plurality of APCs to an engineered cell of the one or more engineered cells expressing a TCR polypeptide.

9. The method of claim 7, further comprising, after (b'), selecting an APC, wherein the selected APC has reactivity to the engineered cell of the one or more engineered cells expressing a TCR polypeptide.

10. The method of claim 8, further comprising, after (b''), selecting an APC, wherein the selected APC activates the engineered cell of the one or more engineered cells expressing a TCR polypeptide.

11. The method of claim 1, wherein the plurality of natively paired TCR chains is identified simultaneously or from a single reaction.

12. The method of claim 1, wherein the TCR polypeptide is expressed from an exogenous polynucleotide sequence that encodes a first TCR chain and a second TCR chain comprising the at least one pair of natively paired TCR chains.

13. The method of claim 4, wherein each engineered APC of the plurality of engineered APCs comprises an antigen polypeptide expressed from an exogenous polynucleotide sequence encoding a different antigen.

14. The method of claim 4, wherein the engineered APCs are engineered to express MHC genes matched to the subject.

15. The method of claim 4, wherein the engineered APC is derived from a K562 cell line and/or the engineered cell expressing the TCR polypeptide is derived from a Jurkat cell line.

16. The method of claim 4, wherein the method further comprises isolating the selected engineered APC by fluorescence activated cell sorting (FACS).

17. The method of claim 4, wherein the determining the antigen of the engineered APC comprises sequencing a sequence of the engineered APC encoding an antigen presented by the engineered APC.

18. The method of claim 4, wherein the engineered cell is an engineered T-cell that does not express an endogenous TCR polypeptide or is a TCR knockout cell.

19. The method of claim 4, wherein the engineered cell expresses CD4 or CD8.

20. The method of claim 4 wherein the engineered APC comprises an exogenous reporter gene, wherein the reporter gene encodes a fluorescent protein, a cell-surface protein, a luciferase reporter system, IL-6, IL-12, IFNα, IL-23, IL-1, TNF, IL-10, CD80, CD86, MHC I, MHC II, CD11c, CD11b, CD8α, OX40-L, ICOS-1 or CD40.

21. The method of claim 20, wherein the identification of a selected engineered APC comprises assaying for the expression of the reporter gene by cDNA array, mRNA detection, or protein detection, and wherein expression of the reporter gene indicates activation of the engineered cell by the APC or reactivity of the engineered cell to the APC.

22. The method of claim 20, wherein the reporter gene is activated in response to CD80/CD86 on the engineered APC binding to CD28 on the engineered cell.

23. The method of claim 20, wherein the reporter gene is activated downstream of NOTCH signaling activation, downstream of PI3K-AKT signaling activation, downstream of a NF-κB pathway, or downstream of a second receptor wherein the second receptor is activated after binding a ligand secreted by the engineered cell, wherein expression of the ligand is induced by binding of a synthetic NOTCH receptor on the engineered APC.

24. The method of claim 4, wherein the engineered APC does not express an endogenous MHC polypeptide.

25. The method of claim 1, wherein the natively paired TCR chains comprise a TCR-alpha chain and a TCR-beta chain, or a TCR-gamma chain and a TCR-delta chain.

26. A method of treatment, the method comprising administering to a subject in need thereof a therapeutic targeted against a protein comprising the antigen determined according to the method claim 1.

27. The method of claim 26, wherein the therapeutic is a small molecule, a peptide, a protein, an antibody or fragment thereof, a cell therapy, or an immunotherapy.

28. The method of claim 26, wherein the subject has cancer.

29. The method of claim 26, wherein the subject has a disease.

30. The method of claim 4, wherein the antigen polypeptide that is presented by the engineered APC is associated with a disease, cancer or viral infection.

31. The method of claim 4, wherein the plurality of engineered APCs expresses at least one MHC type that is similar to the MHC type of the subject comprising the single immune cell.

32. The method of claim 4, wherein the one or more engineered cells comprises a first plurality of engineered cells from a first subject and a second plurality of engineered cells from a second subject, and wherein the plurality of engineered APCs comprises a first plurality of engineered APCs and a second plurality of engineered APCs.

33. The method of claim 32, wherein the method comprises contacting the first plurality of engineered cells to the first plurality of APCs and contacting the second plurality of engineered cells to the second plurality of APCs.

34. The method of claim 32, wherein the first plurality of engineered APCs and the second plurality of engineered APCs present the same antigen polypeptide.

35. The method of claim 32, wherein the first plurality of engineered APCs expresses a first MHC-type and the second plurality of engineered APCs expresses a second MHC-type.

36. The method of claim 32, wherein the first plurality of engineered cells expresses a first TCR polypeptide specific for the first MHC-type expressed by the first plurality of engineered APCs and the second plurality of engineered cells expresses a second TCR polypeptide specific for the second MHC-type expressed by the second plurality of engineered APCs.

* * * * *

UNITED STATES PATENT AND TRADEMARK OFFICE
CERTIFICATE OF CORRECTION

PATENT NO. : 10,928,392 B2  
APPLICATION NO. : 15/762450  
DATED : February 23, 2021  
INVENTOR(S) : Francois Vigneault et al.

Page 1 of 1

It is certified that error appears in the above-identified patent and that said Letters Patent is hereby corrected as shown below:

On the Title Page

Item (71), Lines 1-6, "ABVITRO LLC, Boston, MA (US); Francois Vigneault, Seattle, WA (US); Adrian Wrangham Briggs, Seattle, WA (US); Stephen J. Goldfless, Seattle, WA (US); Brian J. Belmont, Seattle, WA (US)" should read --ABVITRO LLC, Seattle, WA (US)--.

Signed and Sealed this  
Twentieth Day of April, 2021

Drew Hirshfeld  
*Performing the Functions and Duties of the*  
*Under Secretary of Commerce for Intellectual Property and*  
*Director of the United States Patent and Trademark Office*